(12) United States Patent
Woo et al.

(10) Patent No.: US 8,846,737 B2
(45) Date of Patent: Sep. 30, 2014

(54) COMPOUND

(75) Inventors: Lok Wai Lawrence Woo, Slough (GB); Christian Bubert, Slough (GB); Paul Michael Wood, Slough (GB); Aurélien Putey, Genay (FR); Atul Purohit, Slough (GB); Barry Victor Lloyd Potter, Slough (GB)

(73) Assignee: Sterix Limited, Slough, Berkshire (GB)

( * ) Notice: Subject to any disclaimer, the term of this patent is extended or adjusted under 35 U.S.C. 154(b) by 0 days.

(21) Appl. No.: 13/392,206

(22) PCT Filed: Aug. 23, 2010

(86) PCT No.: PCT/GB2010/051391
§ 371 (c)(1),
(2), (4) Date: Jun. 6, 2012

(87) PCT Pub. No.: WO2011/023989
PCT Pub. Date: Mar. 3, 2011

(65) Prior Publication Data
US 2012/0238550 A1 Sep. 20, 2012

(30) Foreign Application Priority Data
Aug. 24, 2009 (GB) .................................. 0914767.9

(51) Int. Cl.
*C07D 249/08* (2006.01)
(52) U.S. Cl.
USPC ....................................... 514/383; 548/264.8
(58) Field of Classification Search
USPC .............................. 514/383; 548/264.8, 265.4
See application file for complete search history.

(56) References Cited

U.S. PATENT DOCUMENTS

| | | | |
|---|---|---|---|
| 5,227,393 A | 7/1993 | Lang et al. | |
| 5,674,886 A * | 10/1997 | Okada et al. | ................... 514/383 |
| 2002/0019527 A1 | 2/2002 | Wang et al. | |

FOREIGN PATENT DOCUMENTS

| | | |
|---|---|---|
| EP | 0371564 A2 | 6/1990 |
| EP | 0490816 A2 | 6/1993 |
| EP | 0641785 A1 | 3/1995 |
| EP | 1431292 A1 | 6/2004 |
| EP | 1544195 A1 | 6/2005 |
| GB | 2256137 A | 12/1992 |
| WO | WO-84/03564 A1 | 9/1984 |
| WO | WO-96/15257 | 5/1990 |
| WO | WO-91/13083 | 9/1991 |
| WO | WO-93/05063 | 3/1993 |
| WO | WO-93/05064 | 3/1993 |
| WO | WO-9805635 A | 2/1998 |
| WO | WO-9807859 A | 2/1998 |
| WO | WO 98/09985 A | 3/1998 |
| WO | WO-9808870 A | 3/1998 |
| WO | WO-98/13348 A1 | 4/1998 |
| WO | WO-99/17777 A1 | 4/1999 |
| WO | WO-99/50453 A1 | 10/1999 |
| WO | WO-99/52890 A1 | 10/1999 |
| WO | WO-2005/058842 A1 | 6/2005 |
| WO | WO-2005/115996 | 12/2005 |
| WO | WO-03/045925 | 6/2006 |

OTHER PUBLICATIONS

Okada, et al (Chemical and Pharmaceutical Bulletin, 1997, 45(2), pp. 333-337).*
Phillips, H.J., (eds. Knise, D.F. and Patterson, M.K.), Dye Exclusion Test or Cell Viability, Tissue culture and applications, 1973, pp. 406-408, chapter 5, Academic Press, New York.
Bradford, M., A Rapid and Sensitive Method for the Quanitation of Microgram Quantities of Protein Utilizing the Principle of Protein-Dye Binding, Analytical Biochemistry, 1976, 72, pp. 248-254.
Newtown, C.J. et al., Aromatse Activity and Concentrations of Cortisol, Progesterone and Testosterone in Breast and Abdominal Adipose Tissue, J. Steroid Biochem, 1986, 24, No. 5, pp. 1033-1039.
Gould, P.L., "Salt selection for basic drugs", Int. J. Pharm., 1986, 33, pp. 201-217.
Yen, P.H. et al., Cloning and Expression of Steroid Sulfates cDNA and the Frequent Occurrence of Deletions in STS Deficiency: Implications for X-Y Interchange, Cell, 1987, vol. 49, pp. 443-454.
Wouters, W. et al., R 76713, a new specific non-steroidal aromatase inhibitor, J. Steroid Biochem, 1989, 32, pp. 781-788.
Stein, C et al., Cloning and Expression of Human Steroidsulfatse, J. Biol. Chem., 1989, vol. 264, No. 23, pp. 13865-13872.
Bulman Page P.C. et al., Efficient Regioselective A-Ring Functionalization of Oestrogens, Tetrahedron, 1990, vol. 46, No. 6, pp. 2059-2068.
Sakura, N. et al., Allergic disease as an associative of steroid sulphate deficiency, Journal Inherited Metabolic Disease, Nov. 1997, 20(6), pp. 807-810.
Le Roy, I. et al., Genetic Correlation Between Steroid Sulfatase Concentration and Initiation of Attack Behavior in Mice, Behavior Genetics, Mar. 1999, 29(2), pp. 131-136.
Boivin, R.P. et al., Structure-activity Relationships of 17α-Derivatives of Estradiol as Inhibitors of Steroid Sulfatase, J. Med. Chem., 2000, 43, pp. 4465-4478.
Bhatnager, A.S. et al., Intracellular aromatase and its relevance to the pharmacological efficacy of aromatase inhibitors, Journal of Steroid Biochemical Molecular Biology, 2001, 76, pp. 199-202.
Tong, Y. et al., "Discovery of potent imidazole and cyanopheryl containing farnesytransferase inhibitors with improved oral bioavailability", Bioorganic & Medicinal Chemistry Letters, 2003, vol. 13, No. 9, pp. 1571-1574.
Lodish et al., Cell Division and the Cell Cycle, "Molecular Cell Biology", 3rd edition, pp. 177-181.
Steroid sulphatase E.C. 3.1.6.2., 1961.

* cited by examiner

*Primary Examiner* — Kamal Saeed
(74) *Attorney, Agent, or Firm* — Frommer Lawrence & Haug LLP; Sandra Kuzmich; Russell A. Garman

(57) ABSTRACT

There is provided a compound of formula I

Figure 1:
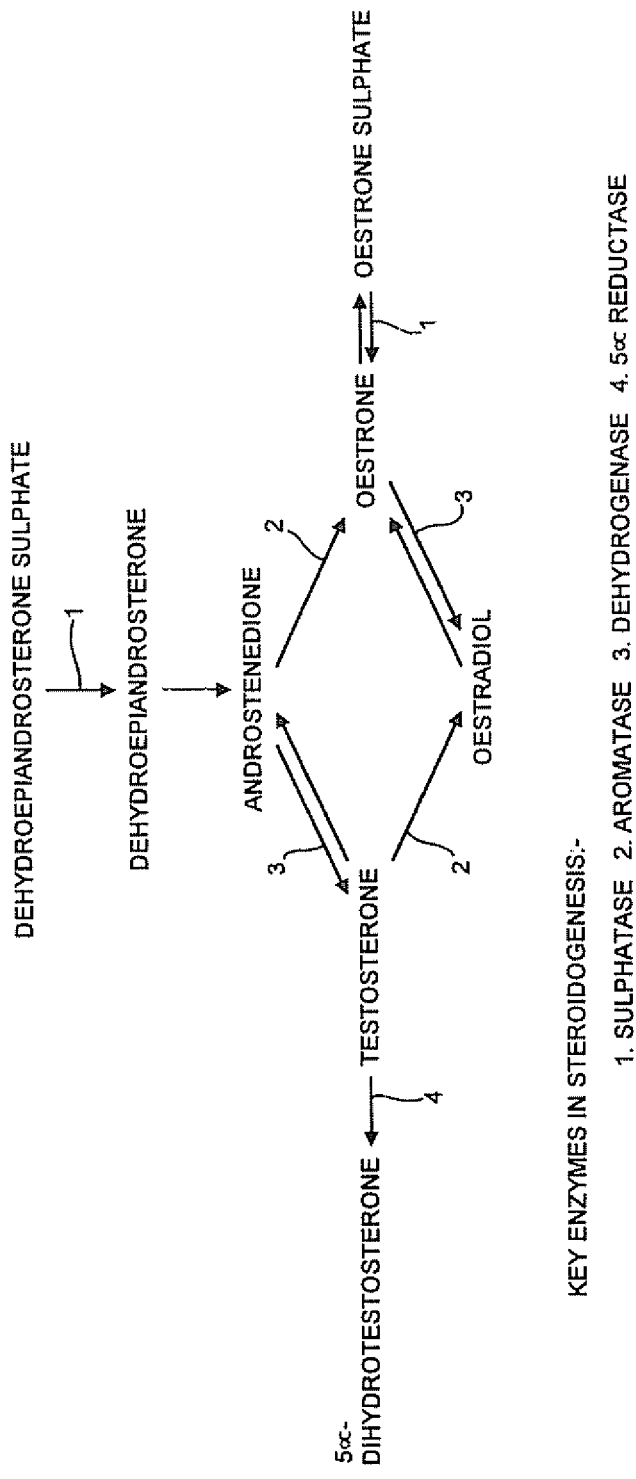

Formula I wherein Z is selected from N and $CR_{22}$, wherein $R_{22}$ is H or a bond with D;

wherein D is selected from a bond, C=O, and linear or branched hydrocarbon groups having a carbon chain of from 1 to 6 carbon atoms, wherein the carbon chain optionally contains an oxy group (=O), an ether (—O—) or thioether (—S—) link, wherein $R_1$ is selected from: triazolyl, imidazolyl, pyrimidinyl radical wherein each of $R_2$ to $R_6$ is independently selected from —H, $NO_2$, halo, —CN, —N[(C=O)$_{0-1}$$R_{12}$][(C=O)$_{0-1}$$R_{13}$] and —(CH$_2$)$_{0-1}$$R_{14}$, or two adjacent groups of $R_2$ to $R_6$, together with the carbon atoms to which they are attached, form a ring, wherein at least one of $R_2$ to $R_6$ is —CN, wherein
(i) at least one of $R_2$ to $R_6$ is —(CH$_2$)$_{0-1}$$R_{14}$, or
(ii) at least one of $R_2$ to $R_6$ is —N[(C=O)$_{0-1}$$R_{12}$][(C=O)$_{0-1}$$R_{13}$], or
(iii) at least two adjacent groups of $R_2$ to $R_6$ together with the carbon atoms to which they are attached, form a ring, or
(iv) at least one of $R_2$ to $R_6$ is —(CH$_2$)$_{0-1}$—O—R'$_{14}$, wherein $R_{12}$ and $R_{13}$ are independently selected from H, linear or branched hydrocarbon groups having a carbon chain of from 1 to 10 carbon atoms, or together with the atoms to which they are attached, may form a mono or bicyclic ring having from 5 to 14 ring members wherein $R_{14}$ is selected from:
aliphatic ring systems
unsubstituted or substituted monocyclic aliphatic heterocycles;
unsubstituted or substituted heteroaryl radical, and
unsubstituted or substituted phenyl group;
the group of formula

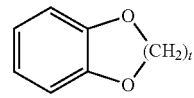

wherein t is 1 or 2 wherein R'$_{14}$ is a unsubstituted or substituted phenyl group;

wherein each of $R_7$ to $R_{11}$ is independently selected from —H, $NO_2$, halo, —O—($C_1$-$C_6$)haloalkyl, ($C_1$-$C_6$)haloalkyl, ($C_1$-$C_6$)alkyl, —CN, —OH, —OPh, —OBn, -Ph, —OSO$_2$NR$_{15}$R$_{16}$, —SO$_2$R$_{26}$, —SO$_2$NR$_{27}$R$_{28}$, —O—($C_1$-$C_6$)alkyl, —(C=O)$_{0-1}$NR$_{29}$R$_{30}$ and —CO(O)$_{0-1}$R$_{31}$;

wherein $R_{15}$ and $R_{16}$ are independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups wherein each of $R_{26}$ to $R_{31}$ is independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups;

or any pharmaceutically acceptable salts thereof.

18 Claims, 2 Drawing Sheets

COMPOUND

FIELD OF INVENTION

The present invention relates to a compound
In particular the present invention relates to a compound and to a pharmaceutical composition comprising the compound The present invention also relates to the use of the compound or composition in therapy applications

BACKGROUND TO THE INVENTION

Evidence suggests that oestrogens are the major mitogens involved in promoting the growth of tumours in endocrine-dependent tissues, such as the breast and endometrium. Although plasma oestrogen concentrations are similar in women with or without breast cancer, breast tumour oestrone and oestradiol levels are significantly higher than in normal breast tissue or blood. In situ synthesis of oestrogen is thought to make an important contribution to the high levels of oestrogens in tumours and therefore inhibitors, in particular specific inhibitors, of oestrogen biosynthesis are of potential value for the treatment of endocrine-dependent turnouts Over the past two decades, there has been considerable interest in the development of inhibitors of the aromatase pathway—which converts the androgen precursor androstenedione to oestrone. However, there is now evidence that the oestrone sulphatase (E1-STS) pathway, i.e. the hydrolysis of oestrone sulphate to oestrone (E1S to E1), and aromatase (i.e. conversion of androstenedione to oestrone) account for the production of oestrogens in breast tumours.

Figure 2:
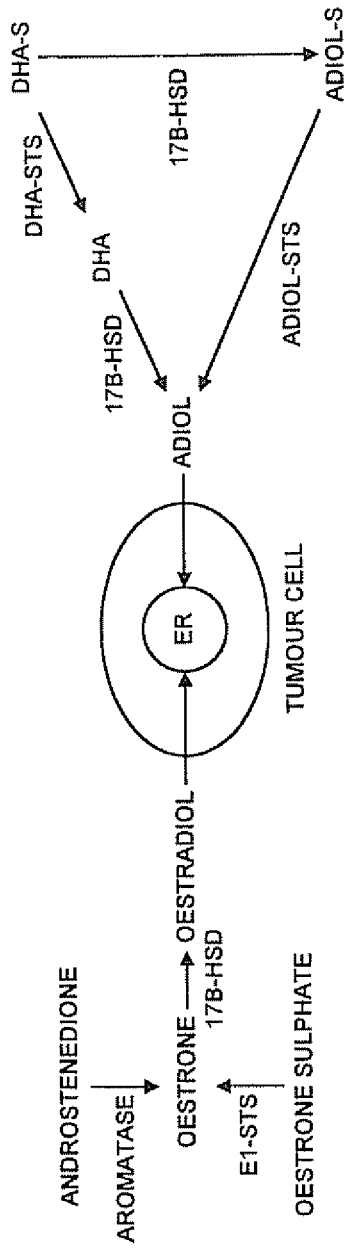

FIGS. 1 and 2 are schematic diagrams showing some of the enzymes involved in the in situ synthesis of oestrone from oestrone sulphate, oestradiol and androstenedione In FIG. 2, which schematically shows the origin of oestrogenic steroids in postmenopausal women, "ER" denotes Oestrogen Receptor, "DHA-S" denotes Dehydroepiandrosterone-Sulphate, "Adiol" denotes Androstenediol, "E1-STS" denotes Oestrone Sulphatase, "DHA-STS" denotes DHA-sulphatase, "Adiol-STS" denotes Adiol Sulphatase, and "17B-HSD" denotes Oestradiol 17B-hydroxysteroid dehydrogenase.

As can be seen, the main two enzymes that are involved in the peripheral synthesis of oestrogens are the aromatase enzyme and the enzyme oestrone sulphatase In short, the aromatase enzyme converts androstenedione, which is secreted in large amounts by the adrenal cortex, to oestrone Recent reports have suggested that some flavones could inhibit aromatase activity.

Much of the oestrone so formed, however, is converted to oestrone sulphate (E1S) and there is now a considerable body of evidence showing that E1S in plasma and tissue acts as a reservoir for the formation of oestrone by the action of oestrone sulphatase In this regard, it is now believed that the oestrone sulphatase (E1-STS) pathway—i.e. the hydrolysis of oestrone sulphate to oestrone (E1S to E1) is a major source of oestrogen in breast tumours This theory is supported by a modest reduction of plasma oestrogen concentration in postmenopausal women with breast cancer treated by aromatase inhibitors, such as aminoglutethimide and 4-hydroxyandrostenedione and also by the fact that plasma E1S concentration in these aromatase inhibitor-treated patients remains relatively high. The long half-life of E1S in blood (10-12 h) compared with the unconjugated oestrogens (20 min) and high levels of steroid sulphatase activity in liver and, normal and malignant breast tissues, also lend support to this theory Thus, oestrogen formation in malignant breast and endometrial tissues via the sulphatase pathway makes a major contribution to the high concentration of oestrogens which are present in these tumours. However, inhibition of both the aromatase and sulphatase pathways could offer considerable therapeutic benefit.

PCT/GB92/01587 teaches novel steroid sulphatase inhibitors and pharmaceutical compositions containing them for use in the treatment of oestrone dependent tumours, especially breast cancer. These steroid sulphatase inhibitors are sulphamate esters, such as N,N-dimethyl oestrone-3-sulphamate and, preferably, oestrone-3-sulphamate (otherwise known as "EMATE") EMATE has the following structure:

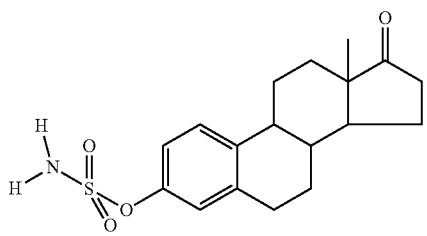 [SMILES: CC12CCC3c4ccc(OS(N)(=O)=O)cc4CCC3C1CCC2=O]

It is known that EMATE is a potent E1-STS inhibitor as it displays more than 99% inhibition of E1-STS activity in intact MCF-7 cells at 0.1 nM. EMATE also inhibits the E1-STS enzyme in a time and concentration-dependent manner, indicating that it acts as an active site-directed inactivator. Although EMATE was originally designed for the inhibition of E1-STS, it also inhibits dehydroepiandrosterone sulphatase (DHA-STS), which is an enzyme that is believed to have a pivotal role in regulating the biosynthesis of the oestrogenic steroid androstenediol Also, there is now evidence to suggest that androstenediol may be of even greater importance as a promoter of breast tumour growth EMATE is also active in vivo as almost complete inhibition of rat liver E1-STS (99%) and DHA-STS (99%) activities resulted when it is administered either orally or subcutaneously. In addition, EMATE has been shown to have a memory enhancing effect in rats. Studies in mice have suggested an association between DHA-STS activity and the regulation of part of the immune response. It is thought that this may also occur in humans. The bridging O-atom of the sulphamate moiety in EMATE is important for inhibitory activity. Thus, when the 3-O-atom is replaced by other heteroatoms as in oestrone-3-N-sulphamate and oestrone-3-S-sulphamate, these analogues are weaker non-time-dependent inactivators.

In addition to oestrone, the other major steroid with oestrogenic properties which is produced by postmenopausal women is androstenediol (see FIG. 2)

Androstenediol, although an androgen, can bind to the oestrogen receptor (ER) and can stimulate the growth of ER positive breast cancer cells and the growth of carcinogen-induced mammary tumours in the rat. Importantly, in postmenopausal women 90% of the androstenediol produced originates from the androgen dehydroepiandrosterone sulphate (DHA-S) which is secreted in large amounts by the adrenal cortex. DHA-S is converted to DHA by DHA sulphatase, which may be the same as, or different from, the enzyme, oestrone sulphatase, which is responsible for the hydrolysis of E1S.

During the last 10-15 years considerable research has also been carried out to develop potent aromatase inhibitors, some of which are now marketed. However, in three recent reports of postmenopausal women with breast cancer who received aromatase inhibitor therapy, plasma E1S concentrations remained between 400-1000 pg/ml.

In summation therefore in situ synthesis of oestrogen is thought to make an important contribution to the high levels of oestrogens in tumours and therefore specific inhibitors of oestrogen biosynthesis are of potential value for the treatment of endocrine-dependent tumours Moreover, even though oestrogen formation in malignant breast and endometrial tissues via the sulphatase pathway makes a major contribution to the high concentration of oestrogens, there are still other enzymatic pathways that contribute to in vivo synthesis of oestrogen.

The present invention seeks to provide novel compounds suitable for the inhibition of steroid sulphatase activity and aromatase activity.

SUMMARY ASPECTS OF THE PRESENT INVENTION

The present invention is based on the surprising finding that certain polycyclic compounds could be used as effective steroid sulphatase inhibitors and/or aromatase inhibitors and/or as agents that can influence cell cycling and/or as agents that can influence apoptosis In one aspect, the present invention is based on the surprising finding that certain polycyclic compounds could be used as effective steroid sulphatase inhibitors and/or aromatase inhibitors and/or as modulators of cell cycling and/or as modulators of apoptosis The polycyclic compounds comprise at least a central trivalent or tetravalent atom to which is attached either direct or indirectly via a linker at least three ring systems. At least one of the ring systems comprises a —CN as a substituent on the ring system The compounds of the present invention may comprise other substituents These other substituents may, for example, further increase the activity of the compounds of the present invention and/or increase stability (ex vivo and/or in vivo)

DETAILED ASPECTS OF THE PRESENT INVENTION

According to one aspect of the present invention, there is provided a compound of formula I

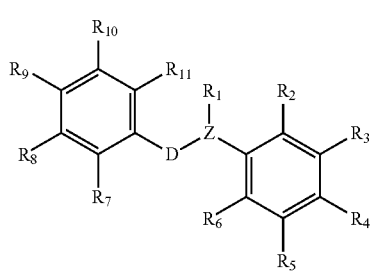

Formula I wherein Z is selected from N and $CR_{22}$, wherein $R_{22}$ is H or a bond with D;

wherein D is selected from a bond, C=O, and linear or branched hydrocarbon groups having a carbon chain of from 1 to 6 carbon atoms, wherein the carbon chain optionally contains an oxy group (=O), an ether (—O—) or thioether (—S—) link, wherein $R_1$ is selected from: triazolyl, imidazolyl, pyrimidinyl radical wherein each of $R_2$ to $R_6$ is independently selected from —H, —CN, $NO_2$, halo, —N[(C=O)$_{0-1}R_{12}$][(C=O)$_{0-1}R_{13}$] and —(CH$_2$)$_{0-1}R_{14}$, or two adjacent groups of $R_2$ to $R_6$, together with the carbon atoms to which they are attached, form a ring, wherein at least one of $R_2$ to $R_6$ is —CN, wherein (i) at least one of $R_2$ to $R_6$ is —(CH$_2$)$_{0-1}R_{14}$, or (ii) at least one of $R_2$ to $R_5$ is —N[(C=O)$_{0-1}R_{12}$][(C=O)$_{0-1}R_{13}$], or (iii) at least two adjacent groups of $R_2$ to $R_6$ together with the carbon atoms to which they are attached, form a ring, or (iv) at least one of $R_2$ to $R_6$ is —(CH$_2$)$_{0-1}R'_{14}$, wherein $R_{12}$ and $R_{13}$ are independently selected from H, linear or branched hydrocarbon groups having a carbon chain of from 1 to 10 carbon atoms, or together with the atoms to which they are attached, may form a mono or bicyclic ring having from 5 to 14 ring members wherein $R_{14}$ is selected from:

aliphatic ring systems unsubstituted or substituted monocyclic aliphatic heterocycles;

unsubstituted or substituted heteroaryl radical, and unsubstituted or substituted phenyl group;

the group of formula

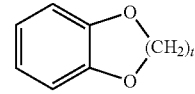

wherein t is 1 or 2 wherein $R'^{14}$ is a unsubstituted or substituted phenyl group;

wherein each of $R_7$ to $R_{11}$ is independently selected from —H, $NO_2$, halo, —O—(C$_1$-C$_5$)haloalkyl, (C$_1$-C$_6$)haloalkyl, (C$_1$-C$_6$)alkyl, —CN, —OH, —OPh, —OBn, -Ph, —OSO$_2$NR$_{15}$R$_{16}$, —SO$_2$R$_{26}$, —SO$_2$NR$_{27}$R$_{28}$, —(C=O)$_{0-1}$NR$_{29}$R$_{30}$ and —CO(O)$_{0-1}$R$_{31}$;

wherein $R_{15}$ and $R_{16}$ are independently selected from H, alkyl, cycloalkyl, alkenyl, to acyl and aryl, or combinations thereof, or together represent alkylene, wherein the or each alkyl or cycloalkyl or alkenyl optionally contain one or more hetero atoms or groups wherein each of $R_{26}$ to $R_{31}$ is independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups, or any pharmaceutically acceptable salts thereof and preferably a compound of formula I wherein Z is selected from N and $CR_{22}$, wherein $R_{22}$ is H or a bond with D;

wherein D is selected from a bond, C=O, and linear or branched hydrocarbon groups having a carbon chain of from 1 to 6 carbon atoms, wherein the carbon chain optionally contains an ether (—O—) or thioether (—S—) link, wherein $R_1$ is selected from: triazolyl, imidazolyl, pyrimidinyl radical wherein each of $R_2$ to $R_6$ is independently selected from —H, $NO_2$, halo, —CN, —N[(C=O)$_{0-1}R_{12}$][(C=O)$_{0-1}R_{13}$] and —(CH$_2$)$_{0-1}R_{14}$, or two adjacent groups of $R_2$ to $R_6$, together with the carbon atoms to which they are attached, form a ring, wherein at least one of $R_2$ to $R_6$ is —CN,
wherein
(i) at least one of $R_2$ to $R_6$ is —$(CH_2)_{0-1}R_{14}$, or
(ii) at least one of $R_2$ to $R_6$ is —$N[(C=O)_{0-1}R_{12})][(C=O)_{0-1}R_{13}]$, or
(iii) at least two adjacent groups of $R_2$ to $R_6$ together with the carbon atoms to which they are attached, form a ring, or wherein $R_{12}$ and $R_{13}$ are independently selected from H, linear or branched hydrocarbon groups having a carbon chain of from 1 to 10 carbon atoms,
or together with the atoms to which they are attached, may form a mono or bicyclic ring having from 5 to 14 ring members
  wherein $R_{14}$ is selected from:
  aliphatic ring systems
  unsubstituted or substituted monocyclic aliphatic heterocycles;
  unsubstituted or substituted heteroaryl radical, and
  unsubstituted or substituted phenyl group;
  wherein each of $R_7$ to $R_{11}$ is independently selected from —H, $NO_2$, halo, —O—$(C_1-C_6)$haloalkyl, $(C_1-C_6)$alkyl, —CN, —OH, —OPh, —OBn, -Ph, —$OSO_2NR_{15}R_{16}$, —$SO_2R_{26}$, —$SO_2NR_{27}R_{28}$, —O—$(C_1-C_6)$alkyl, —$(C=O)_{0-1}NR_{29}R_{30}$ and —$CO(O)_{0-1}R_{31}$;
  wherein $R_{15}$ and $R_{16}$ are independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups
  wherein each of $R_{26}$ to $R_{31}$ is independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups;
  or any pharmaceutically acceptable salts thereof.

According to the present invention, pharmaceutically acceptable salt means an addition salt with the pharmaceutically acceptable mineral or organic or inorganic acids of said product of the present invention As pharmaceutically acceptable inorganic acids, we can mention hydrochloride, hydrobromide, sulfate, phosphate, diphosphate and nitrate. As pharmaceutically acceptable organic acids, we can mention acetate, maleate, fumarate, tartrate, succinate, citrate, lactate, methanesulfonate, benzenesulfonate, p-toluenesulfonate, pamoate and stearate As other examples of pharmaceutically acceptable salts, we can refer to "Salt selection for basic drugs", *Int. J. Pharm.* (1986), 33, 201-217.

According to one aspect of the present invention, there is provided a pharmaceutical composition comprising the compound according to the present invention optionally admixed with a pharmaceutically acceptable carrier, diluent, excipient or adjuvant According to one aspect of the present invention, there is provided the use of a compound according to the present invention in the manufacture of a medicament for use in the therapy of a condition or disease associated with sulphatase (STS) and/or aromatase and/or cell cycling and/or apoptosis and/or cell growth.

According to one aspect of the present invention, there is provided the use of a compound according to the present invention in the manufacture of a medicament for use in the therapy of a condition or disease associated with adverse STS levels and/or adverse aromatase levels and/or cell cycling and/or apoptosis and/or cell growth According to one aspect of the present invention, there is provided the use of a compound according to the present invention in the manufacture of a medicament for inhibiting STS activity and/or inhibiting aromatase activity.

According to one aspect of the present invention, there is provided the use of a compound according to the present invention in the manufacture of a medicament for inhibiting STS activity and inhibiting aromatase activity According to one aspect of the present invention, there is provided the use of a compound in the manufacture of a medicament for use in the therapy of a condition or disease associated with aromatase and optionally associated with STS, wherein the compound is of formula I

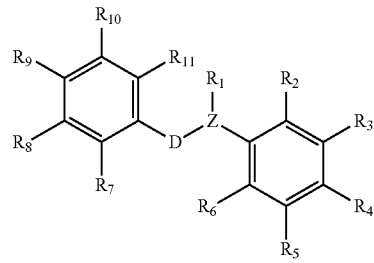

Formula I wherein Z is selected from N and $CR_{22}$, wherein $R_{22}$ is H or a bond with D;
wherein D is selected from a bond, C=O, and linear or branched hydrocarbon groups having a carbon chain of from 1 to 6 carbon atoms, wherein the carbon chain optionally contains an oxy group (=O), an ether (—O—) or thioether (—S—) link,
wherein $R_1$ is selected from: triazolyl, imidazolyl, pyrimidinyl radical
wherein each of $R_2$ to $R_6$ is independently selected from —H, —CN, $NO_2$, halo, —$N[(C=O)_{0-1}R_{12}][(C=O)_{0-1}R_{13}]$ and —$(CH_2)_{0-1}R_{14}$,
or two adjacent groups of $R_2$ to $R_6$, together with the carbon atoms to which they are attached, form a ring,
wherein at least one of $R_2$ to $R_6$ is —CN,
wherein
(i) at least one of $R_2$ to $R_6$ is —$(CH_2)_{0-1}R_{14}$, or
(ii) at least one of $R_2$ to $R_6$ is —$N[(C=O)_{0-1}R_{12}][C=O)_{0-1}R_{13}]$, or
(iii) at least two adjacent groups of $R_2$ to $R_6$ together with the carbon atoms to which they are attached, form a ring, or
(iv) at least one of $R_2$ to $R_6$ is —$(CH_2)_{0-1}R'_{14}$.
wherein $R_{12}$ and $R_{13}$ are independently selected from H, linear or branched hydrocarbon groups having a carbon chain of from 1 to 10 carbon atoms, or together with the atoms to which they are attached, may form a mono or bicyclic ring having from 5 to 14 ring members
  wherein $R_{14}$ is selected from:
  aliphatic ring systems
  unsubstituted or substituted monocyclic aliphatic heterocycles;
  unsubstituted or substituted heteroaryl radical, and
  unsubstituted or substituted phenyl group;
  the group of formula

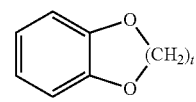

wherein t is 1 or 2
wherein $R'_{14}$ is a unsubstituted or substituted phenyl group;

wherein each of $R_7$ to $R_{11}$ is independently selected from —H, $NO_2$, halo, —O—$(C_1-C_6)$haloalkyl, $(C_1-C_6)$haloalkyl, $(C_1-C_6)$alkyl, —CN, —OH, —OPh, —OBn, -Ph, —$OSO_2NR_{15}R_{16}$, $SO_2R_{26}$, —$SO_2NR_{27}R_{20}$, —O—$(C_1-C_6)$alkyl, —$(C=O)_{0-1}NR_{29}R_{30}$ and —$CO(O)_{0-1}R_{31}$;

wherein $R_{15}$ and $R_{16}$ are independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups wherein each of $R_{26}$ to $R_{31}$ is independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups; or any pharmaceutically acceptable salts thereof, and preferably a compound of formula I wherein Z is selected from N and $CR_{22}$, wherein $R_{22}$ is H or a bond with D;

wherein D is selected from a bond, C=O, and linear or branched hydrocarbon groups having a carbon chain of from 1 to 6 carbon atoms, wherein the carbon chain optionally contains an ether (—O—) or thioether (—S—) link, wherein $R_1$ is selected from: triazolyl, imidazolyl, pyrimidinyl radical wherein each of $R_2$ to $R_5$ is independently selected from —H, $NO_2$, halo, —CN, —$N[(C=O)_{0-1}R_{12}][(C=O)_{0-1}R_{13}]$ and —$(CH_2)_{0-1}R_{14}$, or two adjacent groups of $R_2$ to $R_6$, together with the carbon atoms to which they are attached, form a ring, wherein at least one of $R_2$ to $R_6$ is —CN,
wherein
(i) at least one of $R_2$ to $R_5$ is —$(CH_2)_{0-1}R_{14}$, or
(ii) at least one of $R_2$ to $R_6$ is —$N[(C=O)_{0-1}R_{12}][(C=O)_{0-1}R_{13}]$, or
(iii) at least two adjacent groups of $R_2$ to $R_6$ together with the carbon atoms to which they are attached, form a ring,
or wherein $R_{12}$ and $R_{13}$ are independently selected from H, linear or branched hydrocarbon groups having a carbon chain of from 1 to 10 carbon atoms, or together with the atoms to which they are attached, may form a mono or bicyclic ring having from 5 to 14 ring members wherein $R_{14}$ is selected from:
aliphatic ring systems
unsubstituted or substituted monocyclic aliphatic heterocycles;
unsubstituted or substituted heteroaryl radical, and
unsubstituted or substituted phenyl group;

wherein each of $R_7$ to $R_{11}$ is independently selected from —H, $NO_2$, halo, —O—$(C_1-C_6)$haloalkyl, $(C_1-C_6)$haloalkyl, $(C_1-C_6)$alkyl, —CN, —OH, —OPh, —OBn, -Ph, —$OSO_2NR_{15}R_{16}$, —$SO_2R_{26}$, —$SO_2NR_{27}R_{28}$, —O—$(C_1-C_6)$alkyl, —$(C=O)_{0-1}NR_{29}R_{30}$ and —$CO(O)_{0-1}R_{31}$;

wherein $R_{15}$ and $R_{16}$ are independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups wherein each of $R_{26}$ to $R_{31}$ is independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups; or any pharmaceutically acceptable salts thereof.

According to one aspect of the present invention, there is provided the use of a compound in the manufacture of a medicament for use in the therapy of a condition or disease associated with adverse aromatase levels and optionally associated with adverse STS levels, wherein the compound is of formula I

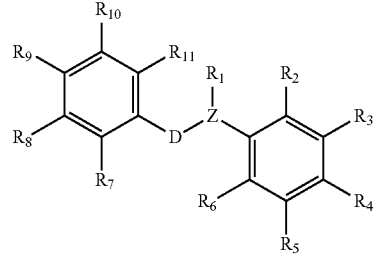

Formula I wherein Z is selected from N and $CR_{22}$, wherein $R_{22}$ is H or a bond with D, wherein D is selected from a bond, C=O and linear or branched hydrocarbon groups having a carbon chain of from 1 to 6 carbon atoms, wherein the carbon chain optionally contains an oxy group (=O), an ether (—O—) or thioether (—S—) link, wherein $R_1$ is selected from triazolyl, imidazolyl, pyrimidinyl radical wherein each of $R_2$ to $R_6$ is independently selected from —H, —CN, $NO_2$, halo, —$N[(C=O)_{0-1}R_{12}][(C=O)_{0-1}R_{13}]$ and —$(CH_2)_{0-1}R_{14}$, or two adjacent groups of $R_2$ to $R_6$, together with the carbon atoms to which they are attached, form a ring, wherein at least one of $R_2$ to $R_6$ is —CN,
wherein
(i) at least one of $R_2$ to $R_6$ is —$(CH_2)_{0-1}R_{14}$, or
(ii) at least one of $R_2$ to $R_6$ is —$N[(C=O)_{0-1}R_{12}][(C=O)_{0-1}R_{13}]$, or
(iii) at least two adjacent groups of $R_2$ to $R_6$ together with the carbon atoms to which they are attached, form a ring, or
(iv) at least one of $R_2$ to $R_6$ is —$(CH_2)_{0-1}$—O—$R_{14}$, wherein $R_{12}$ and $R_{13}$ are independently selected from H, linear or branched hydrocarbon groups having a carbon chain of from 1 to 10 carbon atoms, or together with the atoms to which they are attached, may form a mono or bicyclic ring having from 5 to 14 ring members wherein $R_{14}$ is selected from:
aliphatic ring systems
unsubstituted or substituted monocyclic aliphatic heterocycles;
unsubstituted or substituted heteroaryl radical, and
unsubstituted or substituted phenyl group;
the group of formula

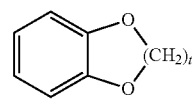

wherein t is 1 or 2
wherein $R'_{14}$ is a unsubstituted or substituted phenyl group;
wherein each of $R_7$ to $R_{11}$ is independently selected from —H, $NO_2$, halo, —O—$(C_1-C_6)$haloalkyl, $(C_1-C_6)$haloalkyl, $(C_1-C_6)$alkyl, —CN, —OH, —OPh, —OBn, -Ph, —OSO$_2$NR$_{15}$R$_{16}$, SO$_2$R$_{26}$, —SO$_2$NR$_{27}$R$_{28}$, —O—(C$_1$-C$_6$)alkyl, —(C=O)$_{0-1}$NR$_{29}$R$_{30}$ and —CO(O)$_{0-1}$R$_{31}$;

wherein R$_{15}$ and R$_{16}$ are independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups wherein each of R$_{26}$ to R$_{31}$ is independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups; or any pharmaceutically acceptable salts thereof, and preferably a compound of formula I wherein Z is selected from N and CR$_{22}$, wherein R$_{22}$ is H or a bond with D;

wherein D is selected from a bond, C=O, and linear or branched hydrocarbon groups having a carbon chain of from 1 to 6 carbon atoms, wherein the carbon chain optionally contains an ether (—O—) or thioether (—S—)

wherein R$_1$ is selected from: triazolyl, imidazolyl, pyrimidinyl radical wherein each of R$_2$ to R$_6$ is independently selected from —H, NO$_2$, halo, —CN, N[(C=O)$_{0-1}$R$_{12}$][(C=O)$_{0-1}$R$_{13}$] and —(CH$_2$)$_{0-1}$R$_{14}$) or two adjacent groups of R$_2$ to R$_6$, together with the carbon atoms to which they are attached, form a ring, wherein at least one of R$_2$ to R$_6$ is —CN, wherein (i) at least one of R$_2$ to R$_6$ is —(CH$_2$)$_{0-1}$R$_{14}$, or (ii) at least one of R$_2$ to R$_6$ is —N[(C=O)$_{0-1}$R$_{12}$][(C=O)$_{0-1}$R$_{13}$], or (iii) at least two adjacent groups of R$_2$ to R$_6$ together with the carbon atoms to which they are attached, form a ring, or wherein R$_{12}$ and R$_{13}$ are independently selected from H, linear or branched hydrocarbon groups having a carbon chain of from 1 to 10 carbon atoms, or together with the atoms to which they are attached, may form a mono or bicyclic ring having from 5 to 14 ring members wherein R$_{14}$ is selected from aliphatic ring systems unsubstituted or substituted monocyclic aliphatic heterocycles;

unsubstituted or substituted heteroaryl radical, and unsubstituted or substituted phenyl group;

wherein each of R$_7$ to R$_{11}$ is independently selected from —H, NO$_2$, halo, —O—(C$_1$-C$_5$)haloalkyl, (C$_1$-C$_6$)haloalkyl, (C$_1$-C$_6$)alkyl, —CN, —OH, —OPh, —OBn, -Ph, —OSO$_2$NR$_{15}$R$_{16}$, —SO$_2$R$_{26}$, —SO$_2$NR$_{27}$R$_{28}$, —O—(C$_1$-C$_6$)alkyl, —(C=O)$_{0-1}$NR$_{29}$R$_{30}$ and —CO(O)$_{0-1}$R$_{31}$;

wherein R$_{15}$ and R$_{16}$ are independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups wherein each of R$_{26}$ to R$_{31}$ is independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups; or any pharmaceutically acceptable salts thereof.

According to one aspect of the present invention, there is provided the use of a compound in the manufacture of a medicament for inhibiting aromatase activity and optionally for inhibiting STS activity, wherein the compound is of formula

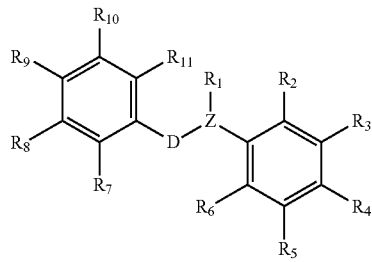

Formula I wherein Z is selected from N and CR$_{22}$, wherein R$_{22}$ is H or a bond with D;

wherein D is selected from a bond, C=O, and linear or branched hydrocarbon groups having a carbon chain of from 1 to 6 carbon atoms, wherein the carbon chain optionally contains an oxy group (=O), an ether (—O—) or thioether (—S—) link, wherein R$_1$ is selected from: triazolyl, imidazolyl, pyrimidinyl radical wherein each of R$_2$ to R$_6$ is independently selected from —H, —CN, NO$_2$, halo, —N[(C=O)$_{0-1}$R$_{12}$][(C=O)$_{0-1}$R$_{13}$] and —(CH$_2$)$_{0-1}$R$_{14}$, or two adjacent groups of R$_2$ to R$_6$, together with the carbon atoms to which they are attached, form a ring, wherein at least one of R$_2$ to R$_6$ is —CN, wherein (i) at least one of R$_2$ to R$_6$ is —(CH$_2$)$_{0-1}$R$_{14}$, or (ii) at least one of R$_2$ to R$_6$ is —N[(C=O)$_{0-1}$R$_{12}$][(C=O)$_{0-1}$R$_{13}$], or (iii) at least two adjacent groups of R$_2$ to R$_6$ together with the carbon atoms to which they are attached, form a ring, or (iv) at least one of R$_2$ to R$_6$ is —(CH$_2$)$_{0-1}$—O—R'$_{14}$, wherein R$_{12}$ and R$_{13}$ are independently selected from H, linear or branched hydrocarbon groups having a carbon chain of from 1 to 10 carbon atoms, or together with the atoms to which they are attached, may form a mono or bicyclic ring having from 5 to 14 ring members wherein R$_{14}$ is selected from:

aliphatic ring systems unsubstituted or substituted monocyclic aliphatic heterocycles;

unsubstituted or substituted heteroaryl radical, and unsubstituted or substituted phenyl group;

the group of formula

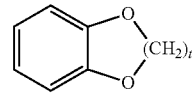

wherein t is 1 or 2 wherein R'$_{14}$ is a unsubstituted or substituted phenyl group;

wherein each of R$_7$ to R$_{11}$ is independently selected from —H, NO$_2$, halo, —O—(C$_1$-C$_6$)haloalkyl, (C$_1$-C$_6$)haloalkyl, (C$_1$-C$_6$)alkyl, —CN, —OH, —OPh, —OBn, -Ph, —OSO$_2$NR$_{15}$R$_{16}$, —SO$_2$R$_{26}$, —SO$_2$NR$_{27}$R$_{28}$, —O—(C$_1$-C$_6$)alkyl, —(C=O)$_{0-1}$NR$_{29}$R$_{30}$ and —CO(O)$_{0-1}$R$_{31}$;

wherein $R_{15}$ and $R_{16}$ are independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups wherein each of $R_{26}$ to $R_{31}$ is independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups; or any pharmaceutically acceptable salts thereof, and prefer ably a compound of formula I wherein Z is selected from N and $CR_{22}$, wherein $R_{22}$ is H or a bond with D;

wherein ID is selected from a bond, C=O, and linear or branched hydrocarbon groups having a carbon chain of from 1 to 6 carbon atoms, wherein the carbon chain optionally contains an ether (—O—) or thioether (—S—) link, wherein $R_1$ is selected from: triazolyl, imidazolyl, pyrimidinyl radical wherein each of $R_2$ to $R_6$ is independently selected from —H, $NO_2$, halo, —CN, —N[(C=O)$_{0-1}R_{12}$][(C=O)$R_{13}$] and —(CH$_2$)$_{0-1}R_{14}$, or two adjacent groups of $R_2$ to $R_6$, together with the carbon atoms to which they are attached, form a ring, wherein at least one of $R_2$ to $R_6$ is —CN, wherein (i) at least one of $R_2$ to $R_6$ is —(CH$_2$)$_{0-1}R_{14}$, or (ii) at least one of $R_2$ to $R_6$ is —N[(C=O)$_{0-1}R_{12}$][(C=O)$_{0-1}R_{13}$], or (iii) at least two adjacent groups of $R_2$ to $R_6$ together with the carbon atoms to which they are attached, form a ring, or wherein $R_{12}$ and $R_{13}$ are independently selected from H, linear or branched hydrocarbon groups having a carbon chain of from 1 to 10 carbon atoms, or together with the atoms to which they are attached, may form a mono or bicyclic ring having from 5 to 14 ring members wherein $R_{14}$ is selected from aliphatic ring systems unsubstituted or substituted monocyclic aliphatic heterocycles;

unsubstituted or substituted heteroaryl radical, and unsubstituted or substituted phenyl group;

wherein each of $R_7$ to $R_{11}$ is independently selected from —H, $NO_2$, halo, —O—(C$_1$-C$_6$)haloalkyl, (C$_1$-C$_6$)haloalkyl, (C$_1$-C$_6$)alkyl, —CN, —OH, —OPh, —OBn, -Ph, —OSO$_2NR_{15}R_{16}$, —SO$_2R_{26}$, —SO$_2NR_{27}R_{28}$, —O—(C$_1$-C$_6$)alkyl, —(C=O)$_{0-1}NR_{29}R_{30}$ and —CO(O)$_{0-1}R_{31}$, wherein $R_{15}$ and $R_{16}$ are independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups wherein each of $R_{26}$ to $R_{31}$ is independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups; or any pharmaceutically acceptable salts thereof.

The present invention also encompasses the novel compounds of the present invention (such as those presented herein), as well as processes for making same (such as the processes presented herein) as well as novel intermediates (such as those presented herein) for use in those processes.

For ease of reference, these and further aspects of the present invention are now discussed under appropriate section headings However, the teachings under each section are not necessarily limited to each particular section Some Advantages One key advantage of the present invention is that the compounds of the present invention can act as STS inhibitors One key advantage of the present invention is that the compounds of the present invention can act as aromatase inhibitors One key advantage of the present invention is that the compounds of the present invention can act as STS inhibitors and aromatase inhibitors Another advantage of the compounds of the present invention is that they may be potent in vivo Some of the compounds of the present invention may be non-oestrogenic compounds Here, the term "non-oestrogenic" means exhibiting no or substantially no oestrogenic activity, such as that determined by Protocol 4.

Another advantage is that some of the compounds may not be capable of being metabolised to compounds which display or induce hormonal activity.

Same of the compounds of the present invention are also advantageous in that they may be orally active.

Some of the compounds of the present invention may be useful for the prevention and/or treatment of cancer, such as breast cancer, as well as (or in the alternative) non-malignant conditions, such as the prevention and/or treatment of inflammatory conditions—such as conditions associated with any one or more of: autoimmunity, including for example, rheumatoid arthritis, type I and II diabetes, systemic lupus erythematosus, multiple sclerosis, myasthenia gravis, thyroiditis, vasculitis, ulcerative colitis and Crohn's disease, skin disorders a g acne, psoriasis and contact dermatitis; graft versus host disease; eczema; asthma and organ rejection following transplantation. The compounds of the present invention are useful particularly when pharmaceuticals may need to be administered from an early age.

Thus, some of the compounds of the present invention are also believed to have therapeutic uses other than for the treatment of endocrine-dependent cancers, such as the treatment of autoimmune diseases The compounds of the present invention may also be useful as an inducer of apoptosis.

The compounds of the present invention may also be useful as cell growth inhibitors Preferable Aspects As discussed herein the compound of formula I is

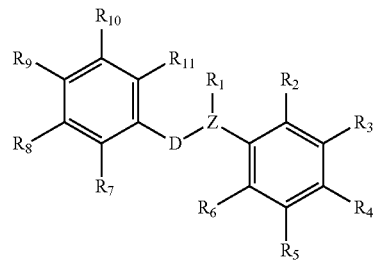

Formula I wherein Z is selected from N and $CR_{22}$, wherein $R_{22}$ is H or a bond with D;

wherein D is selected from a bond, C=O, and linear or branched hydrocarbon groups having a carbon chain of from 1 to 6 carbon atoms, wherein the carbon chain optionally contains an oxy group (=O), an ether (—O—) or thioether (—S—) link, wherein $R_1$ is selected from: triazolyl, imidazolyl, pyrimidinyl radical wherein each of $R_2$ to $R_6$ is independently selected from —H, —CN, $NO_2$, halo, —N[(C=O)$_{0-1}R_{12}$][(C=O)$_{0-1}R_{13}$] and —(CH$_2$)$_{0-1}R_{14}$, or two adjacent groups of $R_2$ to $R_6$, together with the carbon atoms to which they are attached, form a ring, wherein at least one of $R_2$ to $R_8$ is —CN, wherein (i) at least one of $R_2$ to $R_5$ is —(CH$_2$)$_{0-1}R_{14}$, or (ii) at least one of $R_2$ to $R_6$ is —N[(C=O)$_{0-1}R_{12}$][(C=O)$_{0-1}R_{13}$], or (iii) at least two adjacent groups of $R_2$ to $R_6$ together with the carbon atoms to which they are attached, form a ring, or (iv) at least one of $R_2$ to $R_5$ is —(CH$_2$)$_{0-1}$—O—R'$_{14}$, wherein $R_{12}$ and $R_{13}$ are independently selected from H, linear or branched hydrocarbon groups having a carbon chain of from 1 to 10 carbon atoms, together with the atoms to which they are attached, may form a mono or bicyclic ring having from 5 to 14 ring members wherein $R_{14}$ is selected from aliphatic ring systems unsubstituted or substituted monocyclic aliphatic heterocycles;

unsubstituted or substituted heteroaryl radical, and unsubstituted or substituted phenyl group;

the group of formula

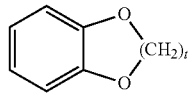

wherein t is 1 or 2 wherein R'$_{14}$ is a unsubstituted or substituted phenyl group;

wherein each of $R_7$ to $R_{11}$ is independently selected from —H, $NO_2$, halo, —O—(C$_1$-C$_6$)haloalkyl, (C$_1$-C$_6$)haloalkyl, (C$_1$-C$_8$)alkyl, —CN, —OH, —OPh, —OBn, -Ph, —OSO$_2$NR$_{15}R_{16}$, —SO$_2R_{26}$, —SO$_2$NR$_{27}R_{28}$, —O—(C$_1$-C$_6$)alkyl, —(C=O)$_{0-1}$NR$_{29}R_{30}$ and —CO(O)$_{0-1}R_{31}$;

wherein $R_{15}$ and $R_{16}$ are independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups wherein each of $R_{26}$ to $R_{31}$ is independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups or any pharmaceutically acceptable salts thereof, and preferably a compound of formula I wherein Z is selected from N and CR$_{22}$, wherein $R_{22}$ is H or a bond with D;

wherein D is selected from a bond, C=O and linear or branched hydrocarbon groups having a carbon chain of from 1 to 6 carbon atoms, wherein the carbon chain optionally contains an ether (—O—) or thioether (—S—) link, wherein $R_1$ is selected from triazolyl, imidazolyl, pyrimidinyl radical wherein each of $R_2$ to $R_6$ is independently selected from —H, $NO_2$, halo, —CN, —N[(C=O)$_{0-1}R_{12}$][(C=O)$_{0-1}R_{13}$] and —(CH$_2$)$_{0-1}R_{14}$, or two adjacent groups of $R_2$ to $R_6$, together with the carbon atoms to which they are attached, form a ring, wherein at least one of $R_2$ to $R_6$ is —CN, wherein (i) at least one of $R_2$ to $R_8$ is —(CH$_2$)$_{0-1}R_{14}$, or (ii) at least one of $R_2$ to $R_6$ is —N[(C=O)$_{0-1}R_{12}$][(C=O)$_{0-1}R_{13}$], or (iii) at least two adjacent groups of $R_2$ to $R_6$ together with the carbon atoms to which they are attached, form a ring, or wherein $R_{12}$ and $R_{13}$ are independently selected from H, linear or branched hydrocarbon groups having a carbon chain of from 1 to 10 carbon atoms, or together with the atoms to which they are attached, may form a mono or bicyclic ring having from 5 to 14 ring members wherein $R_{14}$ is selected from:

aliphatic ring systems unsubstituted or substituted monocyclic aliphatic heterocycles;

unsubstituted or substituted heteroaryl radical, and unsubstituted or substituted phenyl group;

wherein each of $R_7$ to $R_{11}$ is independently selected from —H, $NO_2$, halo, —O—(C$_1$-C$_6$)haloalkyl, (C$_1$-C$_6$)haloalkyl, (C$_1$-C$_6$)alkyl, —CN, —OH, —OPh, —OBn, -Ph, —OSO$_2$NR$_{15}R_{16}$, —SO$_2R_{26}$, —SO$_2$NR$_{27}R_{28}$, —O—(C$_1$-C$_6$)alkyl, —(C=O)$_{0-1}$NR$_{29}R_{30}$ and —CO(O)$_{0-1}R_{31}$;

wherein $R_{15}$ and $R_{16}$ are independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups wherein each of $R_{26}$ to $R_{31}$ is independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups; or any pharmaceutically acceptable salts thereof.

It will be understood by one skilled in the art that when D is a bond, Z is directly attached to the adjacent ring. Thus, in this aspect the compound is of the formula

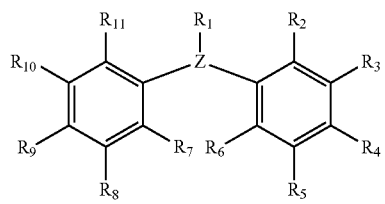

It will be appreciated that when Z is N the compound is of formula Ia

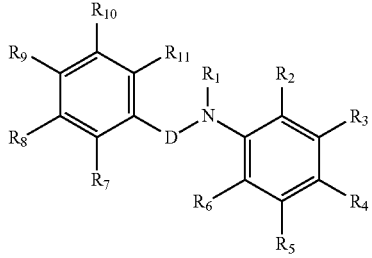

Formula Ia

It will be appreciated that when Z is CH the compound is of formula Ib

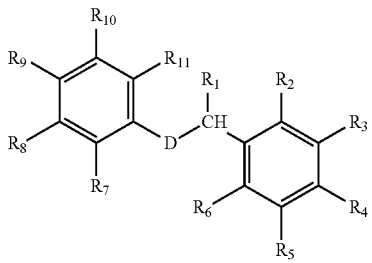

Formula Ib

It will be appreciated that when Z is $CR_{22}$ and $R_{22}$ a bond with D, wherein D is selected from linear or branched hydrocarbon groups having a carbon chain of from 1 to 6 carbon atoms, wherein the carbon chain optionally contains an oxy group (═O), an ether (—O—) or thioether (—S—) link, the compound is of formula Ic

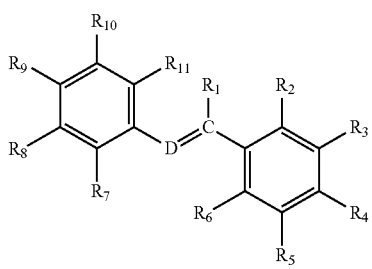

Formula Ic

It will be understood by one skilled in the art when $R_{22}$ is a bond with D, D must be selected from linear or branched hydrocarbon groups having a carbon chain of from 1 to 6 carbon atoms, wherein the carbon chain optionally contains an oxy group (═O), an ether (—O—) or thioether (—S—) link When $R_{22}$ is a bond with D, D itself cannot be a bond or be C═O The carbon chain containing an oxy group (═O) may be illustrated by the following radicals: —C(O)—CH$_2$—, —CH$_2$—C(O)—CH$_2$—, —C(O)—CH$_2$—CH$_2$—

In one preferred aspect D is selected from a bond and linear hydrocarbon groups having a carbon chain of from 1 to 6 carbon atoms.

Preferably, D is selected from a bond, C═O, and —(CH$_2$)$_n$— wherein n is from 1 to 6, wherein —(CH$_2$)$_n$— may contain an oxy group (═O), an ether (—O—) or thioether (—S—) link. Preferably, D is selected from a bond, C═O, and —(CH$_2$)$_n$— wherein n is from 1 to 6, wherein —(CH$_2$)$_n$— may contain an ether (—O—) or thioether (—S—) link. Preferably, D is selected from a bond, C═O, and —(CH$_2$)$_n$— wherein n is from 1 to 6, wherein —(CH$_2$)$_n$— may contain an oxy group (═O). More preferably, D is selected from a bond, C═O, and —(CH$_2$)$_n$— wherein n is 1, 2 or 3, wherein —(CH$_2$)$_n$— may contain an ether (—O—) or thioether (—S—) link. More preferably, D is selected from —(CH$_2$)$_n$— wherein n is 1, 2 or 3, wherein —(CH$_2$)$_n$— may contain an oxy group (═O) More preferably D is —(CH$_2$)$_n$— wherein n is 1, 2 or 3 More preferably, D is selected from a bond, C═O, and —(CH$_2$)$_n$— wherein n is 1 or 2, wherein —(CH$_2$)$_n$— may contain an ether (—O—) or thioether (—S—) link. More preferably D is —(CH$_2$)$_n$— wherein n is 1 or 2

Preferably, D is selected from a bond, C═O, and —CH$_2$— Preferably, D is selected from —C(O)—CF$_2$—CH$_2$—, —CH$_2$—CH$_2$— and —CH$_2$—. More preferably D is —CH$_2$—, As discussed herein, in Formula I and each of the other formulae described herein, $R_1$ is preferably selected from

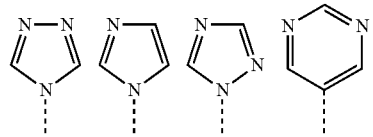

wherein - - - denotes the point of attachment.

As discussed herein, in Formula I and each of the other formulae described herein, $R_1$ is more preferably selected from

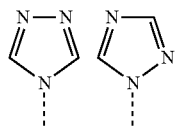

wherein - - - denotes the point of attachment

As discussed herein, in Formula I and each of the other formulae described herein, $R_1$ is to more preferably

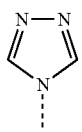

wherein - - - denotes the point of attachment.

Thus in these aspects there is provided compounds of the formulae

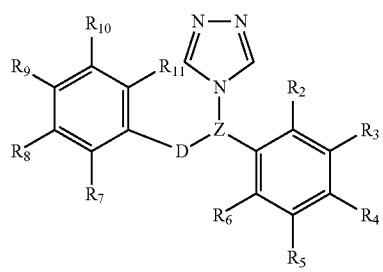

-continued

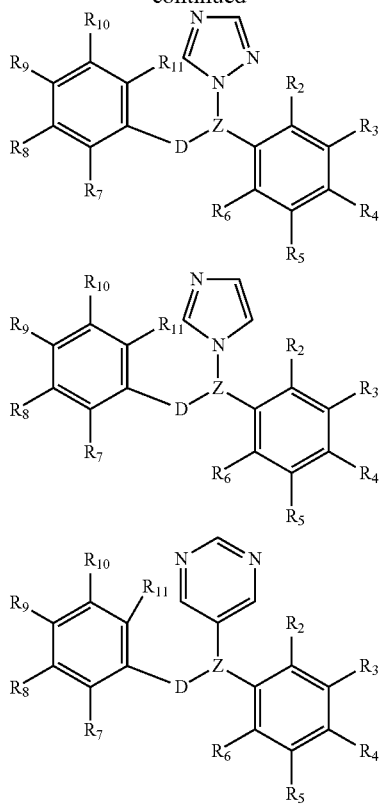

In a preferred aspect, the compound is of formula II or formula III

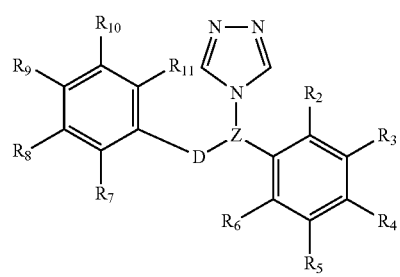

Formula II

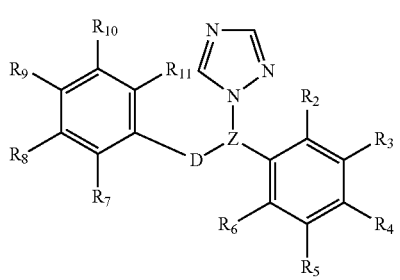

Formula III and preferably of formula II

In another aspect, preferred compounds are of formula V

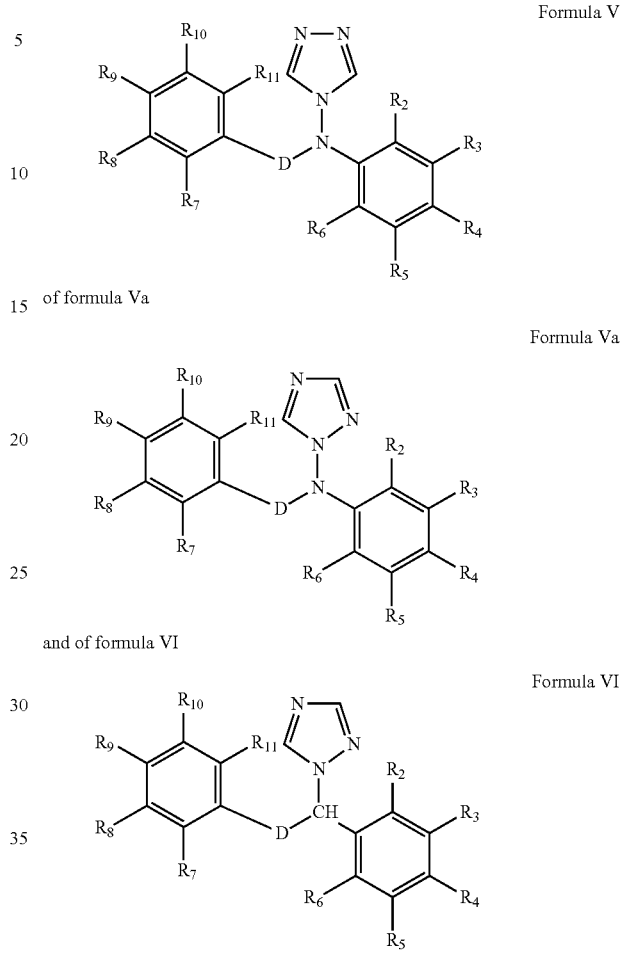

Formula V of formula Va

Formula Va and of formula VI

Formula VI

As discussed herein each of $R_2$ to $R_5$ is independently selected from —H, —CN, $NO_2$, halo, —N[(C=O)$_{0-1}R_{12}$][(C=O)$_{0-1}R_{13}$] and —(CH$_2$)$_{0-1}R_{14}$, or two adjacent groups of $R_2$ to $R_6$, together with the carbon atoms to which they are attached, form a ring, wherein at least one of $R_2$ to $R_6$ is —CN. In one preferred aspect each of $R_2$ to $R_6$ is independently selected from —H, $NO_2$, —Cl, —CN, —N[(C=O)$_{0-1}R_{12}$][(—CO)$_{0-1}R_{13}$] and —(CH$_2$)$_{0-1}R_{14}$. In a further preferred aspect each of $R_2$ to $R_5$ is independently selected from —H, —CN, —N[(C=O)$_{0-1}R_{12}$][(C=O)$_{0-1}R_{13}$] and —(CH$_2$)$_{0-1}R_{14}$. In one aspect at least one of $R_2$ to $R_6$ is —N[(C=O)$_{0-1}R_{12}$][(C=O)$_{0-1}R_{13}$]. In one aspect at least one of $R_2$ to $R_6$ is —(CH$_2$)$_{0-1}R_{14}$. In one aspect at least two adjacent groups of $R_2$ to $R_6$, together with the carbon atoms to which they are attached, form a ring In the aspect that two adjacent groups of $R_2$ to $R_6$, together with the carbon atoms to which they are attached, form a ring, preferably the said ring is fused to the phenyl ring and comprises from 5 to 6 ring members and wherein the additional ring members, that is the ring members which do not belong to the phenyl ring, are selected from: =C($R_{32}$)—, —C$R_{33}R_{34}$—, —C(O)—, —O—, —S—, —N($R_{35}$)—, and =N—, wherein each of $R_{32}$ to $R_{35}$ independently represents H or $C_1$-$C_6$ alkyl.

Any of $R_2$ to $R_6$ may be the required —CN. In one aspect $R_2$ is —CN. In one aspect $R_3$ is —CN. In one aspect $R_4$ is —CN. In one aspect $R_5$ is —CN. In one aspect $R_6$ is —CN Preferably $R_4$ is —CN.

In this aspect preferably each of $R_2$ to $R_6$ is independently selected from —H, —CN, $NO_2$, halo, —N[(C=O)$_{0-1}R_{12}$][(C=O)$_{0-1}R_{13}$] and —(CH$_2$)$_{0-1}R_{14}$, or two adjacent groups of $R_2$ to $R_6$, together with the carbon atoms to which they are attached, form a ring, wherein the ring system formed by two adjacent groups of $R_2$ to $R_6$, together with the carbon atoms to which they are attached is selected from 5 or 6 membered rings, wherein the ring contains carbon and optionally one or more of O, N and S.

More preferably each of $R_2$ to $R_6$ is independently selected from —H, —CN, $NO_2$, halo, —N[(C=O)$_{0-1}R_{12}$][(C=O)$_{0-1}R_{13}$], —(CH$_2$)$_{0-1}R_{14}$ and ring systems formed by two adjacent groups of $R_2$ to $R_6$, together with the carbon atoms to which they are attached, wherein the ring system formed by two adjacent groups of $R_2$ to $R_6$ together with the carbon atoms to which they are attached is selected from

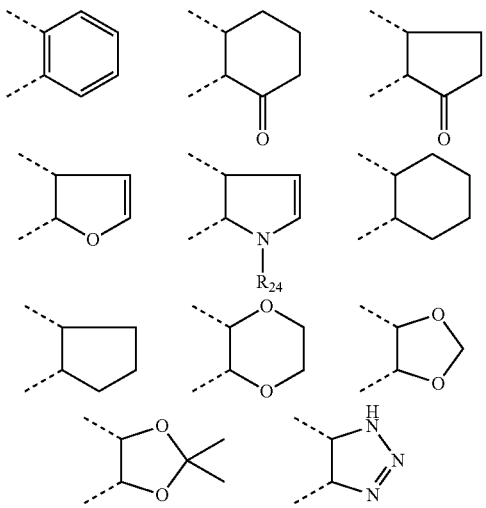

wherein - - - denotes the points of attachment to the two of $R_2$ to $R_6$ and $R_{24}$ is selected from H and linear or branched hydrocarbon groups having a carbon chain of from 1 to 6 carbon atoms. Yet more preferably each of $R_2$ to $R_6$ is independently selected from —H, —CN, $NO_2$, halo, —$NR_{12}R_{13}$, —(CH$_2$)$_{0-1}R_{14}$ and ring systems formed by two of $R_2$ to $R_6$, wherein the two of $R_2$ to $R_6$ together with phenyl ring to which they are fused form a group selected from naphthyl, benzofuranyl and benzotriazolyl In another preferred aspect, $R_2$ to $R_6$ is independently selected from —H, —CN, $NO_2$, halo, —N[(C=O)$_{0-1}R_{12}$][(C=O)$_{0-1}R_{13}$] and —(CH$_2$)$_{0-1}R_{14}$, and more preferably, each of $R_2$ to $R_6$ is independently selected from —H, —CN, $NO_2$, halo, —$NR_{12}R_{13}$, —(CH$_2$)$_{0-1}R_{14}$ Any of $R_2$ to $R_6$ may be a —(CH$_2$)$_{0-1}R_{14}$ group. In one aspect $R_2$ is a —(CH$_2$)$_{0-1}R_{14}$ group. In one aspect $R_3$ is a —(CH$_2$)$_{0-1}R_{14}$ group. In one aspect $R_4$ is a —(CH$_2$)$_{0-1}R_{14}$ group In one aspect $R_5$ is a —(CH$_2$)$_{0-1}R_{14}$ group. In one aspect $R_6$ is a —(CH$_2$)$_{0-1}R_{14}$ group. Preferably $R_3$ is a —(CH$_2$)$_{0-1}R_{14}$ group.

The —(CH$_2$)$_{0-1}R_{14}$ group may contain or may not contain the CH$_2$ moiety. Thus in one aspect the group is —$R_{14}$. In a further aspect, the group is —CH$_2R_{14}$. In one preferred aspect the CH$_2$ moiety is only present when $R_{14}$ is an unsubstituted phenyl or a monocyclic aliphatic heterocycles selected from heterocycles containing at least nitrogen atom and 4 to 6 ring members. In one preferred aspect the CH$_2$ moiety is only present when $R_{14}$ is selected from substituted or unsubstituted phenyl, cyclic amine, piperazine, morpholine, lactam, pyrrolidinedione, azetidine, 1,3-diazetidine, 1,3-oxazetidine, 1,3-piperazine, 1,3-oxazinane and piperidinedione groups. In one preferred aspect the CH$_2$ moiety is only present when $R_{14}$ is selected from

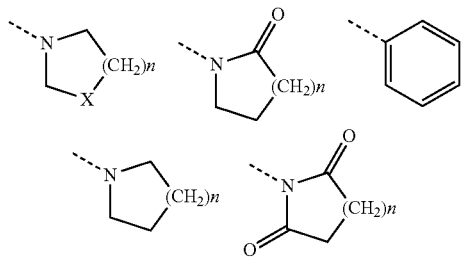

X = O, N wherein n is 1, 2 or 3

In one preferred aspect the CH$_2$ moiety is only present when $R_{14}$ is a phenyl group. In this aspect, the group CH$_2R_{14}$ provides a benzyl group (which may be substituted or unsubstituted)

In one preferred aspect $R_3$ is a —(CH$_2$)$_{0-1}R_{14}$ group and $R_4$ is —CN In another preferred aspect, $R_3$ is —N[(C=O)$_{0-1}R_{12}$][(C=O)$_{0-1}R_{13}$] and $R_4$ is —CN.

In one preferred aspect, $R_2$ to $R_6$ is independently selected from —H, —CN, —(CH$_2$)$_{0-1}R_{14}$ In one preferred aspect, $R_2$ and $R_5$ are H In another one preferred aspect, $R_2$, $R_5$ and $R_6$ are H.

In one preferred aspect, $R_2$, $R_5$ and $R_6$ are H and $R_4$ is —CN

The $R_{14}$ group is selected from aliphatic ring systems, unsubstituted or substituted monocyclic aliphatic heterocycles, unsubstituted or substituted heteroaryl radical, and unsubstituted or substituted phenyl group; In one aspect $R_{14}$ is an aliphatic ring system The $R_{14}$ aliphatic ring system includes $C_3$-$C_{12}$ cycloalkyl such as cyclopropyl, cyclopentyl, cyclohexyl, cycloheptyl, cyclooctyl, or cycloalkenyl such as cyclohexenyl. In one aspect $R_{14}$ is an unsubstituted or substituted monocyclic aliphatic heterocycle. The $R_{14}$ aliphatic heterocycle includes aliphatic cycle, saturated or unsaturated, and comprising at least one heteroatom selected from N, O and S, such as pyrrolidine, imidazolidine, pyrrazolidine, isothiazolidine, thiazolidine, isoxazolidine, oxazolidine, piperidine, piperazine, morpholine, dihydrooxazole, dihydroimidazole, dihydrofurane, dihydrothiophene. In one aspect $R_{14}$ is an unsubstituted or substituted heteroaryl radical. The $R_{14}$ heteroaryl radical designates an aromatic radical, constituted by a condensed ring or rings, with at least one ring containing one or more identical or different heteroatoms chosen from sulphur, nitrogen or oxygen. As examples of heteroaryl radicals, the following radicals can be mentioned: pyrrolyl, imidazolyl, pyrazolyl, isothiazolyl, thiazolyl, isoxazolyl, oxazolyl, oxadiazolyl, triazolyl, thiadiazolyl, pyridyl, pyrazinyl, pyrimidyl, pyridazinyl, quinolyl, isoquinolyl, quinoxalinyl, indolyl, benzotriazolyl, benzothiazolyl, benzoxadiazoyl, carbazolyl, phenoxazinyl, thieno pyridinyl, thienopyrazinyl, thienyl, benzothienyl, furyl, benzofuryl, dihydrobenzofuryl, thioxanthenyl, pyranyl, benzopyranyl, dibenzopyrazinyl, acridinyl In one preferred aspect the CH$_2$ moiety is only present when $R_{14}$ is selected from substituted or unsubstituted phenyl, cyclic amine, piperazine, morpholine, lactam, pyrrolidinedione and piperidinedine groups. In one aspect $R_{14}$ is a group selected from

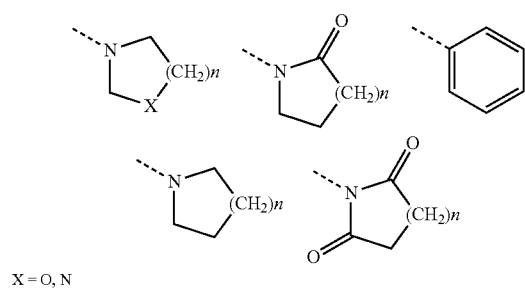

X = O, N which may be unsubstituted or substituted
and wherein n is 1, 2 or 3

In a preferred aspect $R_{14}$ is an unsubstituted or substituted phenyl group. The phenyl group may substituted by one or more identical or different substituent selected from; —CN, $NO_2$, halo, $(C_1\text{-}C_6)$haloalkyl, $(C_1\text{-}C_6)$alkyl, —OH, —$OSO_2NR_{15}R_{16}$, —$SO_2NR_{27}R_{28}$, aryl, aryloxy, arylalkyloxy, —$O(C_1\text{-}C_6)$alkyl, —O—$(C_1\text{-}C_6)$haloalkyl, —C(O)—O—$R_{31}$, —$NR_{41}R_{42}$, —$SO_2$—$R_{26}$ and —$(C=O)_{0-1}NR_{29}R_{30}$, each of $R_{31}$, $R_{41}$ and $R_{42}$ is independently selected from H and $(C_1\text{-}C_6)$alkyl, $R_{26}$ is selected from a hydrocarbon radical or a radical of formula —$NR_{41}R_{42}$. A preferred unsubstituted or substituted phenyl group for $R_{14}$ is

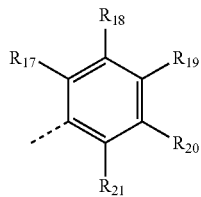

wherein - - - denotes the point of attachment and each of $R_{17}$ to $R_{21}$ is independently selected from —H, $NO_2$, halo, —O—$(C_1\text{-}C_6)$haloalkyl, $(C_1\text{-}C_6)$haloalkyl, $(C_1\text{-}C_6)$alkyl, —CN, —OH, —OPh, —OBn, -Ph, —$OSO_2NR_{15}R_{16}$, —$SO_2R_{26}$, —$SO_2NR_{27}R_{28}$, —$O(C_1\text{-}C_6)$alkyl, —$(C=O)_{0-1}NR_{29}R_{30}$ and —$CO(O)_{0-1}R_{31}$;

wherein $R_{15}$ and $R_{16}$ are independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups wherein each of $R_{26}$ to $R_{31}$ is independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups The $R'_{14}$ group is unsubstituted or substituted phenyl group $R'_{14}$ group may be unsubstituted or phenyl group substituted by one or more substituents selected from —H, $NO_2$, halo, —O—$(C_1\text{-}C_6)$haloalkyl, $(C_1\text{-}C_6)$haloalkyl, $(C_1\text{-}C_6)$alkyl, —CN, —OH, —$O(C_1\text{-}C_6)$alkyl, and more preferably by —$O(C_1\text{-}C_6)$alkyl. In a preferred aspect, —$(CH_2)_{0-1}$—O—$R'_{14}$, is —O—$R'_{14}$.

The term "hydrocarbon" as used herein means any one of an alkyl group, an alkenyl group, an alkynyl group, an acyl group, which groups may be linear, branched or cyclic, or an aryl group The term hydrocarbon also includes those groups but wherein they have been optionally substituted if the hydrocarbon is a branched structure having substituent(s) thereon, then the substitution may be on either the hydrocarbon backbone or on the branch, alternatively the substitutions may be on the hydrocarbon backbone and on the branch.

In one preferred embodiment, the hydrocarbon group is an oxyhydrocarbon group.

Here the term "oxyhydrocarbon" means any one of an alkoxy group, an oxyalkenyl group, an oxyalkynyl group, which groups may be linear, branched or cyclic, or an oxyaryl group. The term oxyhydrocarbon also includes those groups but wherein they have been optionally substituted. If the oxyhydrocarbon is a branched structure having substituent(s) thereon, then the substitution may be on either the hydrocarbon backbone or on the branch; alternatively the substitutions may be on the hydrocarbon backbone and on the branch Preferably the oxyhydrocarbon group is an alkoxy group Preferably the oxyhydrocarbon group is of the formula —O—$(C_1\text{-}C_6)$alkyl, such as —O—$(C_1\text{-}C_3)$alkyl Preferably the hydrocarbon group is an alkyl group, especially $(C_1\text{-}C_6)$alkyl, e.g. methyl, ethyl, n-propyl, isopropyl, n-butyl, sec-butyl, tert-butyl, n-pentyl and other pentyl isomers, and n-hexyl and other hexyl isomers Preferably the alkyl group is $(C_1\text{-}C_3)$alkyl. Preferably the alkyl group is methyl or ethyl, in particular methyl.

In one preferred aspect each of $R_{26}$ to $R_{31}$ is independently selected from H, $(C_1\text{-}C_6)$alkyl, $(C_1\text{-}C_6)$cycloalkyl, $(C_1\text{-}C_6)$alkenyl, $(C_1\text{-}C_6)$ acyl and $(C_1\text{-}C_6)$ aryl, or combinations thereof, or together represent alkylene, wherein the or each alkyl or cycloalkyl or alkenyl optionally contain one or more hetero atoms or groups.

In a preferred aspect the group —O—$(C_1\text{-}C_6)$haloalkyl, is selected from —$OCF_3$ and —$OCF_2CF_3$ A preferred aliphatic ring system for $R_{14}$ is an aliphatic ring containing from 3 to 11 carbons. These rings may be optionally substituted with one or more of $NO_2$, halo, —O—$(C_1\text{-}C_6)$haloalkyl, $(C_1\text{-}C_6)$haloalkyl, $(C_1\text{-}C_6)$alkyl, —CN, —OH, —OPh, —OBn, -Ph, —$OSO_2NR_{15}R_{16}$, —$SO_2R_{26}$, —$SO_2NR_{27}R_{28}$, —O—$(C_1\text{-}C_6)$alkyl, —$(C=O)_{0-1}NR_{29}R_{30}$ and —$CO(O)_{0-1}R_{31}$;

wherein $R_{15}$ and $R_{16}$ are independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups wherein each of $R_{26}$ to $R_{31}$ is independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups Preferably these rings may be optionally substituted with one or more of —$NO_2$, $(CH_2)_{0-6}CF_3$, $(C_1\text{-}C_6)$alkyl, —CN, —OH, —F, —Cl, —Br, —I and —O—$(C_1\text{-}C_6)$alkyl Highly preferred groups are

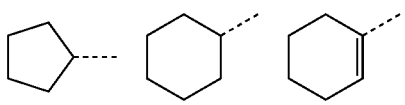

wherein - - - denotes the point of attachment and optionally substituted with one or more of $NO_2$, halo, —O—$(C_1\text{-}C_6)$ haloalkyl, $(C_1\text{-}C_6)$haloalkyl, $(C_1\text{-}C_6)$alkyl, —CN, —OH, —OPh, —OBn, -Ph, —$OSO_2NR_{15}R_{16}$, —$SO_2R_{26}$, —$SO_2NR_{27}R_{28}$, —O—$(C_1\text{-}C_6)$alkyl, —$(C=O)_{0-1}NR_{29}R_{30}$ and —$CO(O)_{0-1}R_{31}$;

wherein $R_{15}$ and $R_{16}$ are independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups wherein each of $R_{26}$ to $R_{31}$ is independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups Preferably these rings may be optionally substituted with one or more of —$NO_2$, $(CH_2)_{0-6}CF_3$, $(C_1$-$C_6)$alkyl, —CN, —OH, —F, —Cl, —Br, —I and —O—$(C_1$-$C_6)$alkyl A more preferred aliphatic ring system for $R_{14}$ is a cycloalkyl group containing from 3 to 6 carbons Highly preferred cycloalkyl groups are

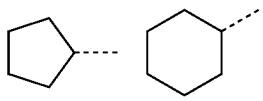

wherein - - - denotes the point of attachment and optionally substituted with one or more of $NO_2$, halo, —O—$(C_1$-$C_6)$ haloalkyl, $(C_1$-$C_6)$haloalkyl, $(C_1$-$C_6)$alkyl, —CN, —OH, —OPh, —OBn, -Ph, —$OSO_2NR_{15}R_{16}$, —$SO_2R_{26}$, —$SO_2NR_{27}R_{28}$, —O—$(C_1$-$C_6)$alkyl, —$(C=O)_{0-1}NR_{29}R_{30}$ and —$CO(O)_{0-1}R_{31}$;

wherein $R_{15}$ and $R_{16}$ are independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups wherein each of $R_{26}$ to $R_{31}$ is independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups. Preferably these rings may be optionally substituted with one or more of —$NO_2$, $(CH_2)_{0-6}CF_3$, $(C_1$-$C_6)$alkyl, —CN, —OH, —F, —Cl, —Br, and —O—$(C_1$-$C_6)$alkyl.

A preferred monocyclic aliphatic heterocycle for $R_{14}$ is a ring comprising 5 or 6 members and containing carbon and one of S, O and N The ring may be optionally substituted with $NO_2$, oxo, halo, —O—$(C_1$-$C_6)$haloalkyl, $(C_1$-$C_6)$haloalkyl, $(C_1$-$C_6)$alkyl, —CN, —OH, —OPh, —OBn, -Ph, —$OSO_2NR_{15}R_{16}$, —$SO_2R_{26}$, —$SO_2NR_{27}R_{28}$, —$(C=O)_{0-1}NR_{29}R_{30}$ and —$CO(O)_{0-1}R_{31}$;

wherein $R_{15}$ and $R_{16}$ are independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups wherein each of $R_{26}$ to $R_{31}$ is independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups. Preferably these rings may be optionally substituted with one or more of —$NO_2$, $(CH_2)_{0-6}CF_3$, $(C_1$-$C_6)$alkyl, —CN, —OH, —F, —Cl, —Br, —I and —O—$(C_1$-$C_6)$alkyl A preferred monocyclic aliphatic heterocycle for $R_{14}$ is selected from

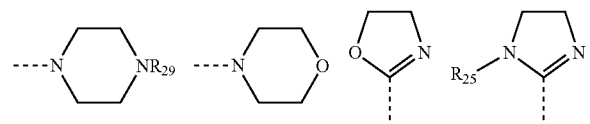

optionally substituted with one or more of $NO_2$, halo, —O—$(C_1$-$C_6)$haloalkyl, $(C_1$-$C_6)$haloalkyl, $(C_1$-$C_6)$alkyl, —CN, —OH, —OPh, —OBn, -Ph, —$OSO_2NR_{15}R_{16}$, —$SO_2R_{26}$, —$SO_2NR_{27}R_{28}$, —O—$(C_1$-$C_6)$alkyl, —$(C=O)_{0-1}NR_{29}R_{30}$ and —$CO(O)_{0-1}R_{31}$;

wherein $R_{15}$ and $R_{16}$ are independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups wherein each of $R_{26}$ to $R_{31}$ is independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups. Preferably these rings may be optionally substituted with one or more of —$NO_2$, $(CH_2)_{0-6}CF_3$, $(C_1$-$C_6)$alkyl, —CN, —OH, —F, —Cl, —Br, —I and —O—$(C_1$-$C_6)$alkyl, wherein $R_{25}$ is selected from H and linear or branched hydrocarbon groups having a carbon chain of from 1 to 6 carbon atoms, wherein $R_{29}$ is selected from H, alkyl, cycloalkyl, alkenyl, acyl and aryl, or combinations thereof, wherein the or each alkyl or cycloalkyl or alkenyl optionally contain one or more hetero atoms or groups. A preferred monocyclic aliphatic heterocycle for $R_{14}$ is selected from piperazine, morpholine, dihydrooxazole and dihydroimidazole, each being optionally substituted. A highly preferred monocyclic aliphatic heterocycle for $R_{14}$ is selected from

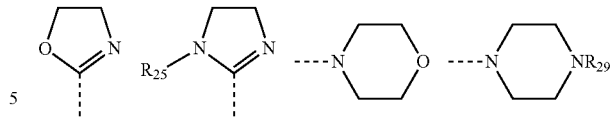

Preferably $R_{29}$ is H. When $R_{29}$ is alkyl, the preferred values are those where $R_{29}$ is independently selected from lower alkyl groups containing from 1 to 6 carbon atoms, that is to say methyl, ethyl, propyl etc. $R_{29}$ may be methyl. When $R_{29}$ is aryl, typical values are phenyl, naphthyl and tolyl, such as m-tolyl, p-tolyl or o-tolyl Where $R_{29}$ represent cycloalkyl, typical values are cyclopropyl, cyclopentyl, cyclohexyl etc. Within the values alkyl, cycloalkyl, alkenyl, acyl and aryl, substituted groups are included containing as substituents therein one or more groups which do not interfere with the sulphatase inhibitory activity of the compound in question Exemplary non-interfering substituents include hydroxy, amino, halo, alkoxy, alkyl and aryl. A preferred heteroaryl for $R_{14}$ is selected from furane, benzofurane, thiophene, oxazole and pyridine. A preferred heteroaryl for $R_{14}$ is selected from

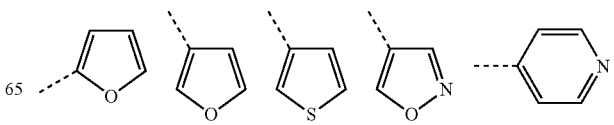

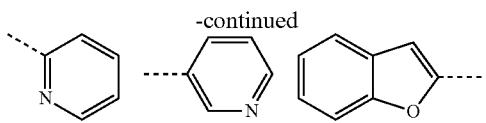

A highly preferred heteroaryl for $R_{14}$ is selected from

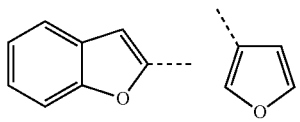

These rings may be substituted with one or more of $NO_2$, halo, $-O-(C_1-C_6)$haloalkyl, $(C_1-C_6)$haloalkyl, $(C_1-C_6)$alkyl, $-CN$, $-OH$, $-OPh$, $-OBn$, -Ph, $-OSO_2NR_{15}R_{16}$, $-SO_2R_{26}$, $-SO_2NR_{27}R_{28}$, $-O-(C_1-C_6)$alkyl, $-(C=O)_{0-1}NR_{29}R_{30}$ and $-CO(O)_{0-1}R_{31}$;

wherein $R_{15}$ and $R_{16}$ are independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups wherein each of $R_{26}$ to $R_{31}$ is independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups. Preferably these rings may be optionally substituted with one or more of $-NO_2$, $(CH_2)_{0-6}CF_3$, $(C_1-C_6)$alkyl, $-CN$, $-OH$, $-Cl$, $-Br$, $-I$ and $-O-(C_1-C_6)$alkyl, wherein $R_{25}$ is selected from H and linear or branched hydrocarbon groups having a carbon chain of from 1 to 6 carbon atoms, wherein $R_{29}$ is selected from H, alkyl, cycloalkyl, alkenyl, acyl and aryl, or combinations thereof, wherein the or each alkyl or cycloalkyl or alkenyl optionally contain one or more hetero atoms or groups A preferred heteroaryl for $R_{14}$ is one of the monocyclic heterocycles described herein having fused thereto a phenyl ring A highly preferred heteroaryl for $R_{14}$ is

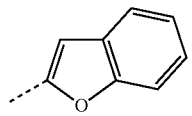

optionally substituted with one or more of $NO_2$, halo, $-O-(C_1-C_6)$haloalkyl, $(C_1-C_6)$haloalkyl, $(C_1-C_6)$alkyl, $-CN$, $-OH$, $-OPh$, $-OBn$, -Ph, $-OSO_2NR_{15}R_{16}$, $-SO_2R_{26}$, $-SO_2NR_{27}R_{28}$, $-O-(C_1-C_6)$alkyl, $-(C=O)_{0-1}NR_{29}R_{30}$ and $-CO(O)_{0-1}R_{31}$;

wherein $R_{15}$ and $R_{16}$ are independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups wherein each of $R_{26}$ to $R_{31}$ is independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups. Preferably optionally substituted with one or more of $-NO_2$, $(CH_2)_{0-6}CF_3$, $(C_1-C_6)$alkyl, $-CN$, $-OH$, $-F$, $-Cl$, $-Br$, $-I$ and $-O-(C_1-C_6)$alkyl As will be understood from these teachings, in a preferred aspect $R_{14}$ group is selected from
(i) group

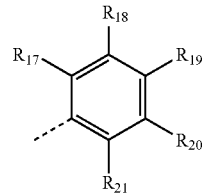

wherein each of $R_{17}$ to $R_{21}$ is independently selected from $-H$, $NO_2$, halo, $-O-(C_1-C_6)$haloalkyl, $(C_1-C_6)$haloalkyl, $(C_1-C_6)$alkyl, $-CN$, $-OH$, $-OPh$, $-OBn$, -Ph, $-OSO_2NR_{15}R_{16}$, $-SO_2R_{26}$, $-SO_2NR_{27}R_{28}$, $-O-(C_1-C_6)$alkyl, $-(C=O)_{0-1}NR_{29}R_{30}$ and $-CO(O)_{0-1}R_{31}$;

wherein $R_{15}$ and $R_{16}$ are independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups wherein each of $R_{26}$ to $R_{31}$ is independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups.

(ii) groups

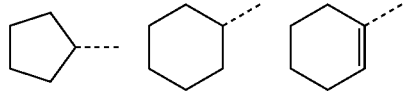

wherein - - - denotes the point of attachment optionally substituted with one or more of $NO_2$, halo, $-O-(C_1-C_6)$haloalkyl, $(C_1-C_6)$haloalkyl, $(C_1-C_6)$alkyl, $-CN$, $-OH$, $-OPh$, $-OBn$, -Ph, $-OSO_2NR_{15}R_{16}$, $-SO_2R_{26}$, $-SO_2NR_{27}R_{28}$, $-O-(C_1-C_6)$alkyl, $-(C=O)_{0-1}NR_{29}R_{30}$ and $CO(O)_{0-1}R_{31}$;

wherein $R_{15}$ and $R_{16}$ are independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups wherein each of $R_{26}$ to $R_{31}$ is independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups.

(iii) groups

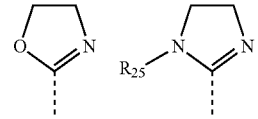

optionally substituted with one or more of $NO_2$, halo, $-O-(C_1-C_6)$haloalkyl, $(C_1-C_6)$haloalkyl, $(C_1-C_6)$alkyl, $-CN$, $-OH$, $-OPh$, $-OBn$, -Ph, $-OSO_2NR_{15}R_{16}$, $-SO_2R_{26}$, $-SO_2NR_{27}R_{28}$, $-O-(C_1-C_6)$alkyl, $-(C=O)_{0-1}NR_{29}R_{30}$ and $-CO(O)_{0-1}R_{31}$;

wherein R$_{15}$ and R$_{16}$ are independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups wherein each of R$_{26}$ to R$_{31}$ is independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups (iv) group

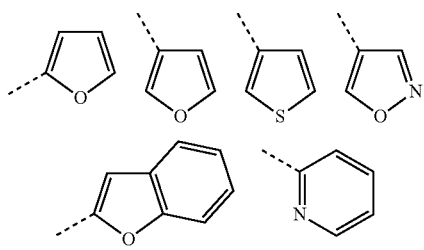

optionally substituted with one or more of from NO$_2$, halo, —O—(C$_1$-C$_6$)haloalkyl, (C$_1$-C$_6$)haloalkyl, (C$_1$-C$_6$)alkyl, —CN, —OH, —OPh, —OBn, -Ph, —OSO$_2$NR$_{15}$R$_{16}$, —SO$_2$R$_{26}$, —SO$_2$NR$_{27}$R$_{28}$, —O—(C$_1$-C$_6$)alkyl, —(C═O)$_{0-1}$NR$_{29}$R$_{30}$ and —CO(O)$_{0-1}$R$_{31}$;

wherein R$_{15}$ and R$_{16}$ are independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups wherein each of R$_{26}$ to R$_{31}$ is independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups In a preferred aspect R$_{14}$ group is

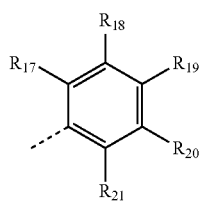

wherein each of R$_{17}$ to R$_{21}$ is independently selected from —H, NO$_2$, halo, (C$_1$-C$_6$)haloalkyl, (C$_1$-C$_6$)alkyl, —CN, —OH, —OSO$_2$NR$_{15}$R$_{16}$, —SO$_2$R$_{26}$, —SO$_2$NR$_{27}$R$_{28}$, and —O—(C$_1$-C$_6$)alkyl; wherein R$_{25}$, R$_{27}$ and R$_{28}$ are independently selected from H, alkyl, cycloalkyl, alkenyl, acyl and aryl, and more preferably wherein each of R$_{17}$ to R$_{21}$ is independently selected from —H, NO$_2$, halo, (C$_1$-C$_6$)haloalkyl, (C$_1$-C$_6$)alkyl, —CN, —OH, —OSO$_2$NR$_{15}$R$_{16}$, —SO$_2$R$_{26}$, —SO$_2$NR$_{27}$R$_{28}$, and —O—(C$_1$-C$_6$)alkyl, and R$_{26}$, R$_{27}$ and R$_{28}$ are independently selected from H and alkyl.

In a more preferred aspect R$_{14}$ group is

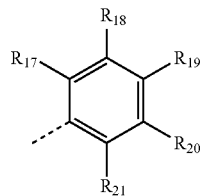

wherein each of R$_{17}$, R$_{18}$, R$_{20}$ and R$_{21}$ are —H and R$_{19}$ is selected from -O—(C$_1$-C$_6$)alkyl, benzyloxy, —OH, —CN, —F, —(CH$_2$)$_{0-5}$CF$_3$ and OSO$_2$NH$_2$ As discussed herein R$_{12}$ and R$_{13}$ are independently selected from H, linear or branched hydrocarbon groups having a carbon chain of from 1 to 10 carbon atoms, or together with the atoms to which they are attached, may form a mono or bicyclic ring having from 5 to 14 ring members; Preferably R$_{12}$ and R$_{13}$ are independently selected from H, linear or branched hydrocarbon groups having a carbon chain of from 1 to 6 carbon atoms, or together with the atoms to which they are attached, may form a mono or bicyclic ring having from 5 to 10 ring members. Preferably R$_{12}$ and R$_{13}$ are independently selected from H, linear or branched hydrocarbon groups having a carbon chain of from 1 to 6 carbon atoms, or together with the atoms to which they are attached, may form a mono or bicyclic ring having 5 or 6 ring members.

In the aspect that R$_{12}$ and R$_{13}$ together with the atoms to which they are attached form a mono or bicyclic ring having from 5 to 14 ring members, preferably the ring members of the mono or bicyclic ring are selected from: ═C(R$_{36}$)—, —CR$_{37}$R$_{38}$—, —O—, ═N—, —N(R$_{39}$)— and

wherein each of R$_{36}$ to R$_{39}$ independently represents H or C$_1$-C$_6$ alkyl In one aspect R$_{12}$ and R$_{13}$ are independently selected from H, linear or branched hydrocarbon groups having a carbon chain of from 1 to 10 carbon atoms, or together with the atoms to which they are attached, may form a mono or bicyclic ring having from 5 to 14 ring members, or R$_{12}$ and R$_{13}$ are independently selected from H, linear or branched hydrocarbon groups having a carbon chain of from 1 to 6 carbon atoms, or together with the atoms to which they are attached, may form a mono or bicyclic ring having from 5 to 10 ring members, or R$_{12}$ and R$_{13}$ are independently selected from H, linear or branched hydrocarbon groups having a carbon chain of from 1 to 6 carbon atoms, or together with the atoms to which they are attached, may form a mono or bicyclic ring having 5 or 6 ring members, or R$_{12}$ and R$_{13}$ together with the atoms to which they are attached, may form a mono or bicyclic ring having 5 or 6 ring members.

It will be understood by one skilled in the art that when R$_{12}$ and R$_{13}$ together with the atoms to which they are attached, may form a mono or bicyclic ring, the group —N[(C═O)$_{0-1}$R$_{12}$][(C═O)$_{0-1}$R$_{13}$] is incorporated into a ring. Thus in this aspect when R$_{12}$ and R$_{13}$ together with the atoms to which they are attached, may form a mono or bicyclic ring the ring may be any ring incorporating the —N[(C=O)$_{0-1}$R$_{12}$][(C=O)$_{0-1}$R$_{13}$] functionality. In this preferred aspect R$_{12}$ and R$_{13}$ together with the atoms to which they are attached may provide (ii) groups

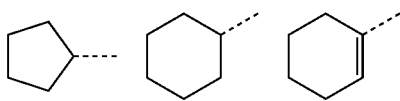

wherein - - - denotes the point of attachment optionally substituted with one or more of NO$_2$, halo, —O—(C$_1$-C$_6$)haloalkyl, (C$_1$-C$_8$)haloalkyl, (C$_1$-C$_6$)alkyl, —CN, —OH, —OPh, —OBn, —Ph, —OSO$_2$NR$_{15}$R$_{16}$, —SO$_2$R$_{26}$, —SO$_2$NR$_{27}$R$_{28}$, —O—(C$_1$-C$_6$)alkyl, —(C=O)$_{0-1}$NR$_{29}$R$_{30}$ and —CO(O)$_{0-1}$R$_{31}$;

wherein R$_{15}$ and R$_{16}$ are independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups wherein each of R$_{26}$ to R$_{31}$ is independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups (iii) groups

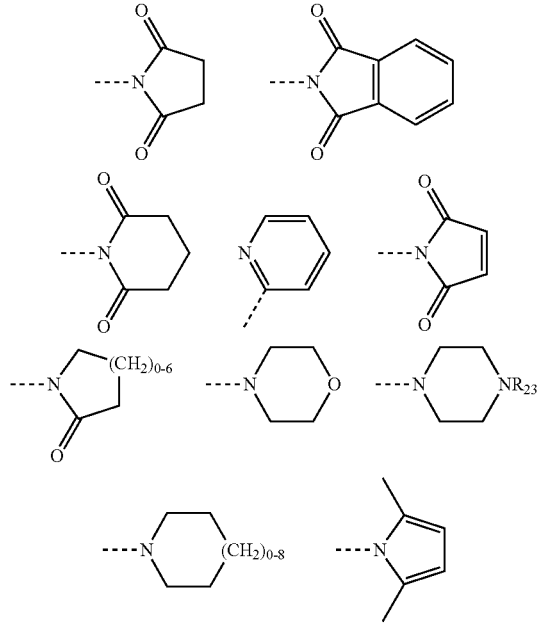

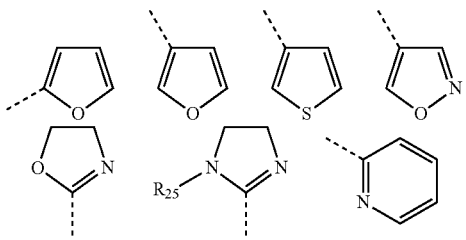

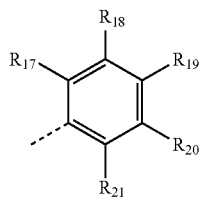

wherein - - - denotes the point of attachment and R$_{23}$ is selected from H and linear or branched hydrocarbon groups having a carbon chain of from 1 to 6 carbon atoms.

in a highly preferred aspect R$_3$ is selected from (i) group optionally substituted with one or more of NO$_2$, halo, —O—(C$_1$-C$_6$)haloalkyl, (C$_1$-C$_6$)haloalkyl, (C$_1$-C$_6$)alkyl, —CM, —OH, —OPh, —OBn, -Ph, —OSO$_2$NR$_{15}$R$_{16}$, —SO$_2$R$_{26}$, —SO$_2$NR$_{27}$R$_{28}$, —O—(C$_1$-C$_6$)alkyl, —(C=O)$_{0-1}$NR$_{29}$R$_{30}$ and —CO(O)$_{0-1}$R$_{31}$;

wherein R$_{15}$ and R$_{16}$ are independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups wherein each of R$_{26}$ to R$_{31}$ is independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups; and (iv) group

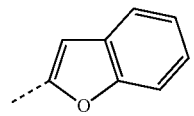

wherein each of R$_{17}$ to R$_{21}$ is independently selected from —H, NO$_2$, halo, —O—(C$_1$-C$_6$)haloalkyl, (C$_1$-C$_6$)haloalkyl, (C$_1$-C$_6$)alkyl, —CN, —OH, —OPh, —OBn, -Ph, —OSO$_2$NR$_{15}$R$_{16}$, —SO$_2$R$_{26}$, —SO$_2$NR$_{27}$R$_{28}$, —O—(C$_1$-C$_6$)alkyl, —(C=O)$_{0-1}$NR$_{29}$R$_{30}$ and —CO(O)$_{0-1}$R$_{31}$;

wherein R$_{15}$ and R$_{16}$ are independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups wherein each of R$_{26}$ to R$_{31}$ is independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups.

optionally substituted with one or more of NO$_2$, halo, —O—(C$_1$-C$_6$)haloalkyl, (C$_1$-C$_6$)haloalkyl, (C$_1$-C$_6$)alkyl, —CN, —OH, —OPh, —OBn, -Ph, —OSO$_2$NR$_{15}$R$_{16}$, —SO$_2$R$_{26}$, —SO$_2$NR$_{27}$R$_{28}$, —O—(C$_1$-C$_6$)alkyl, —(C=O)$_{0-1}$NR$_{29}$R$_{30}$ and —CO(O)$_{0-1}$R$_{31}$;

wherein R$_{15}$ and R$_{16}$ are independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups
wherein each of $R_{26}$ to $R_{31}$ is independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups In a preferred aspect, $R_3$ is

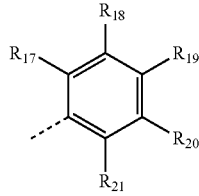

wherein each of $R_{17}$ to $R_{21}$ is independently selected from —H, $NO_2$, halo, $(C_1-C_6)$haloalkyl, $(C_1-C_6)$alkyl, —CN, —OH, —$OSO_2NR_{15}R_{16}$, —$SO_2R_{26}$, —$SO_2NR_{27}R_{28}$, and —O—$(C_1-C_6)$alkyl;
wherein $R_{26}$, $R_{27}$ and $R_{28}$ are independently selected from H, alkyl, cycloalkyl, alkenyl, acyl and aryl In a yet more preferred aspect $R_3$ is

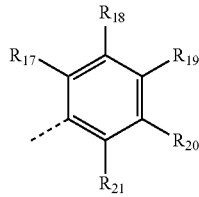

wherein each of $R_{17}$ to $R_{21}$ is independently selected from —H, $NO_2$, $(CH_2)_{0-6}CF_3$, $(C_1-C_6)$alkyl, —CN, —OH, —$OSO_2NR_{15}R_{16}$, —$SO_2R_{26}$, —$SO_2NR_{27}R_{28}$, —F, —Cl, —Br, and —O—$(C_1-C_6)$alkyl In a preferred aspect, $R_3$ is

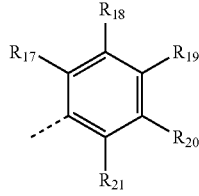

wherein each of $R_{17}$ to $R_{21}$ is independently selected from —H, halo, $(C_1-C_6)$haloalkyl, —$OSO_2NH_2$ and —O—$(C_1-C_6)$alkyl In one preferred aspect, $R_3$ is

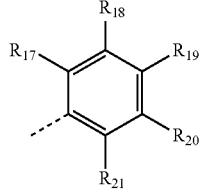

wherein each of $R_{17}$ to $R_{21}$ is —H

In one preferred aspect, $R_{14}$ is an unsubstituted heteroaryl group, and more preferably an heteroaryl selected from furyl, thienyl and benzofuryl.

In one preferred aspect, $R_{14}$ is a monocyclic aliphatic heterocycle, and more preferably a monocyclic aliphatic heterocycle selected from pyrrolidine, piperidine, piperazine, morpholine or azepane, each being optionally substituted by axe or $(C_1-C_6)$alkyl.

In one preferred aspect, $R'_{14}$ group is a unsubstituted phenyl group In another preferred aspect, $R'_{14}$ is a phenyl group substituted by one or more substituents selected from —H, $NO_2$, halo, —O—$(C_1-C_6)$haloalkyl, $(C_1-C_6)$haloalkyl, $(C_1-C_6)$alkyl, —CN, —OH, —$O(C_1-C_6)$alkyl, and more preferably by —$O(C_1-C_6)$alkyl. In a preferred aspect, —$(CH_2)_{0-1}$—O—$R'_{14}$, is —O—$R'_{14}$ In one preferred aspect, $R_{14}$ is

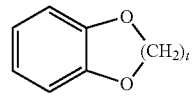

wherein t is 1 or 2 Preferably t is 1

As discussed herein each of $R_7$ to $R_{11}$ is independently selected from —H, $NO_2$, halo, —O—$(C_1-C_6)$haloalkyl, $(C_1-C_6)$haloalkyl, $(C_1-C_6)$alkyl, —CN, —OH, —OPh, —OBn, -Ph, —$OSO_2NR_{15}R_{16}$, —$SO_2R_{26}$, —$SO_2NR_{27}R_{28}$, —O—$(C_1-C_6)$alkyl, —$(C=O)_{0-1}NR_{29}R_{30}$ and —$CO(O)_{0-1}R_{31}$,
wherein $R_{15}$ and $R_{16}$ are independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups
wherein each of $R_{26}$ to $R_{31}$ is independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups. Preferably each of $R_7$ to $R_{11}$ is independently selected from —H, $(C_1-C_6)$alkyl, OH, —$OSO_2NR_{15}R_{16}$, —F, —Cl, —Br and —I. Preferably at least one of $R_7$ to $R_{11}$ is selected from —F, —Cl, —Br and —I. Preferably at least one of $R_7$ to $R_{11}$ is $C_{1-3}$ alkyl. Preferably at least one of $R_7$ to $R_{11}$ is —$OSO_2NR_{15}R_{16}$. In one highly preferred aspect at least one of $R_7$ to $R_{11}$ is selected from —F, —Cl, —Br and —I and at least one of $R_7$ to $R_{11}$ is —$OSO_2NR_{15}R_{16}$.

In one preferred aspect, $R_7$ and $R_{11}$ are —F In another preferred aspect $R_8$ is selected from —F, —Cl, —Br and —I In another preferred aspect, $R_9$ is —OH, —$OSO_2NH_2$ or —Br. In another preferred aspect, $R_9$ is —OH or —$OSO_2NH_2$, and preferably $R_9$ is —$OSO_2NH_2$.

In respect of the group —$OSO_2NR_{15}R_{16}$, $R_{15}$ and $R_{16}$ are independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups Preferably at least one of $R_{15}$ and $R_{16}$ is H. Preferably $R_{15}$ is H and $R_{16}$ is H It will be understood that by 'combinations' of H, alkyl, cycloalkyl, alkenyl, acyl and aryl, it is meant two or more of the groups combined An example of such a combination is an arylalkyl group.

The term "acyl" as used herein includes any group of the formula —(C=O)-alkyl. Preferred acyl groups are —(C=O)—$(C_1-C_{20})$alkyl, —(C=O)—$(C_1-C_{10})$alkyl, —(C=O)—$(C_1-C_6)$alkyl, —(C=O)—$(C_1-C_3)$alkyl and —(C=O)—$CH_3$. These preferred aspects apply to each instance of acyl used herein and in particular, $R_{15}$, $R_{16}$ and each of $R_{26}$ to $R_{31}$.

In respect of the group —$SO_2R_{26}$, $R_{26}$ is selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups. Preferably $R_{26}$ is H. When $R_{26}$ is alkyl, the preferred values are those where $R_{26}$ is independently selected from lower alkyl groups containing from 1 to 6 carbon atoms, that is to say methyl, ethyl, propyl etc $R_{26}$ may be methyl. When $R_{26}$ is aryl, typical values are phenyl, naphthyl and tolyl, such as m-tolyl, p-tolyl or o-tolyl. Where $R_{26}$ represent cycloalkyl, typical values are cyclopropyl, cyclopentyl, cyclohexyl etc Within the values alkyl, cycloalkyl, alkenyl, acyl and aryl, substituted groups are included containing as substituents therein one or more groups which do not interfere with the sulphatase inhibitory activity of the compound in question. Exemplary non-interfering substituents include hydroxy, amino, halo, alkoxy, alkyl and aryl In respect of the group —$SO_2NR_{27}R_{28}$, $R_{27}$ and $R_{28}$ are independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups. Preferably at least one of $R_{27}$ and $R_{28}$ is H. Preferably $R_{27}$ is H and $R_{28}$ is H. When substituted, the N-substituted compounds of this invention may contain one or two N-alkyl, N-alkenyl, N-cycloalkyl or N-aryl substituents, preferably containing or each containing a maximum of 10 carbon atoms. When $R_{27}$ and/or $R_{28}$ is alkyl, the preferred values are those where $R_{27}$ and $R_{28}$ are each independently selected from lower alkyl groups containing from 1 to 6 carbon atoms, preferably lower branched or linear alkyl groups containing from 1 to 6 carbon atoms, that is to say methyl, ethyl, propyl, isopropyl etc $R_{27}$ and $R_{28}$ may both be methyl When $R_{27}$ and/or $R_{28}$ is aryl, typical values are phenyl and tolyl, such as m-tolyl, p-tolyl or o-tolyl. Where $R_{27}$ and $R_{28}$ represent cycloalkyl, typical values are cyclopropyl, cyclopentyl, cyclohexyl etc. When joined together $R_{27}$ and $R_{28}$ typically represent an alkylene group providing a chain of 4 to 6 carbon atoms, optionally interrupted by one or more hetero atoms or groups, e g to provide a 5 membered heterocycle, e.g. morpholino, pyrrolidino or piperidino. Within the values alkyl, cycloalkyl, alkenyl, acyl and aryl substituted groups are included containing as substituents therein one or more groups which do not interfere with the sulphatase inhibitory activity of the compound in question. Exemplary non-interfering substituents include hydroxy, amino, halo, alkoxy, alkyl and aryl.

In one highly preferred aspect $R_9$ is —$OSO_2NR_{15}R_{16}$. Preferably $R_{15}$ and $R_{16}$ are independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups The term "sulphamate" as used herein includes an ester of sulphamic acid, or an ester of an N-substituted derivative of sulphamic acid, or a salt thereof.

If a sulphamate group is present on the compound then the compound of the present invention is referred to as a sulphamate compound.

When substituted, the N-substituted compounds of this invention may contain one or two N-alkyl, N-alkenyl, N-cycloalkyl or N-aryl substituents, preferably containing or each containing a maximum of 10 carbon atoms. When $R_{15}$ and/or $R_{16}$ is alkyl, the preferred values are those where $R_{15}$ and $R_{16}$ are each independently selected from lower alkyl groups containing from 1 to 6 carbon atoms, that is to say methyl, ethyl, propyl etc $R_{15}$ and $R_{16}$ may both be methyl. When $R_{15}$ and/or $R_{16}$ is aryl, typical values are phenyl and tolyl, such as m-tolyl, p-tolyl or o-tolyl Where $R_{15}$ and $R_{16}$ represent cycloalkyl, typical values are cyclopropyl, cyclopentyl, cyclohexyl etc When joined together $R_{15}$ and $R_{16}$ typically represent an alkylene group providing a chain of 4 to 6 carbon atoms, optionally interrupted by one or more hetero atoms or groups, e.g. to provide a 5 membered heterocycle, e.g. morpholino, pyrrolidino or piperidino.

Within the values alkyl, cycloalkyl, alkenyl, acyl and aryl substituted groups are included containing as substituents therein one or more groups which do not interfere with the sulphatase inhibitory activity of the compound in question. Exemplary non-interfering substituents include hydroxy, amino, halo, alkoxy, alkyl and aryl.

In some preferred embodiments, at least one of $R_{15}$ and $R_{16}$ is H

In some further preferred embodiments, each of $R_{15}$ and $R_{16}$ is H

In one highly preferred aspect the compound is formula VII

Formula VII

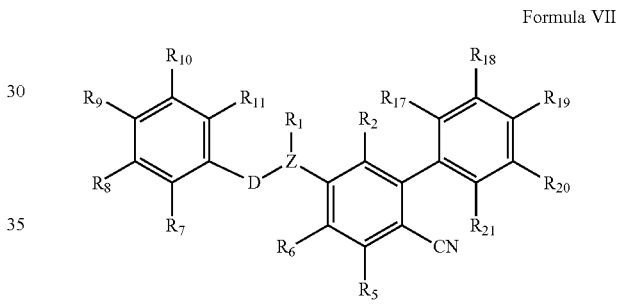

wherein each of $R_{17}$ to $R_{21}$ is independently selected from —H, —CN, —OH, —$OSO_2NR_{15}R_{16}$, —$SO_2R_{26}$, —$SO_2NR_{27}R_{28}$, —F, —Cl, —Br, —I and —O—($C_1$-$C_6$) alkyl.

In one highly preferred aspect the compound is formula VIII

Formula VIII

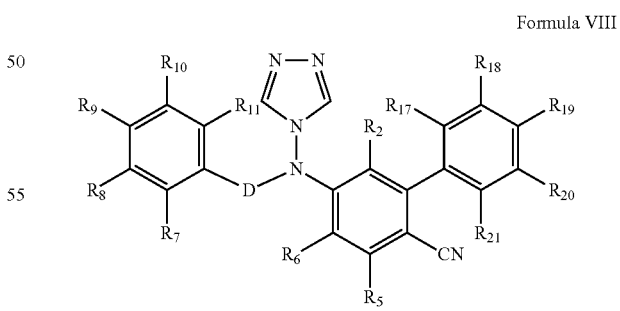

wherein each of $R_{17}$ to $R_{21}$ is independently selected from —H, —CN, —OH, —$OSO_2NR_{15}R_{16}$, —$SO_2R_{26}$, —$SO_2NR_{27}R_{28}$, —F, —Cl, —Br, —I and —O—($C_1$-$C_6$) alkyl.

In a highly preferred aspect, the compound is selected from compounds of the formulae:

35
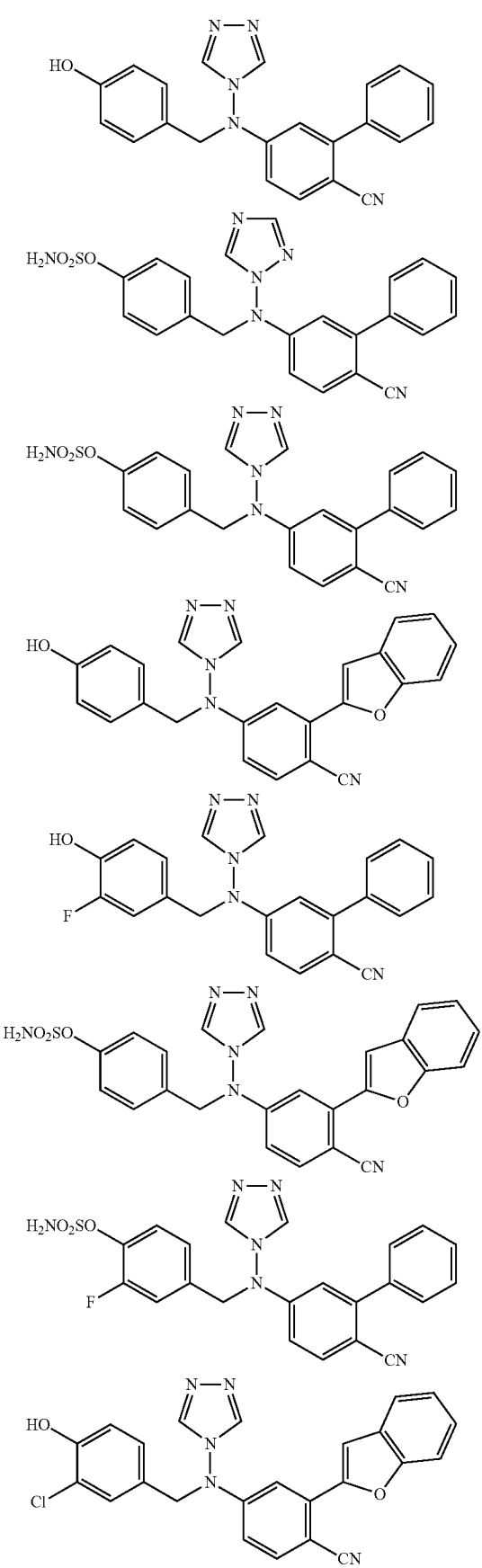
36
-continued
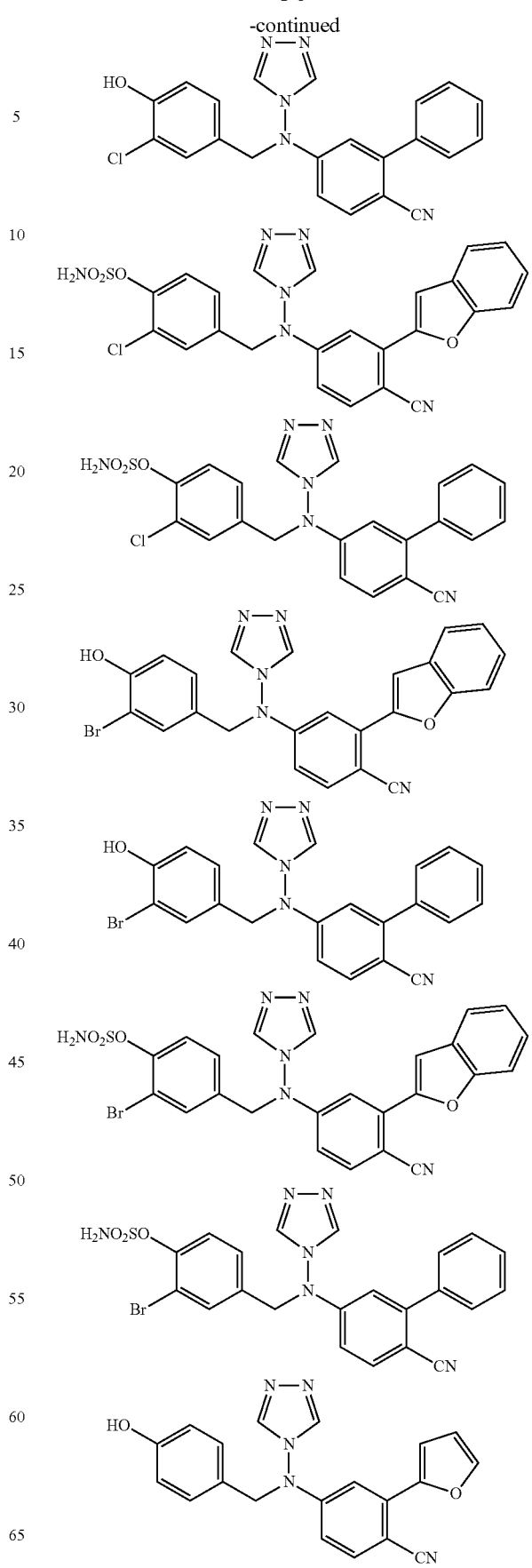

37
-continued
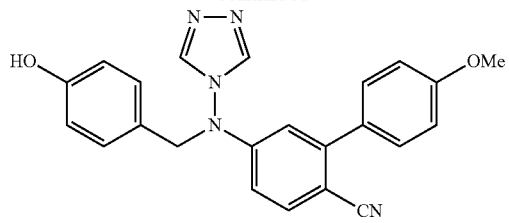
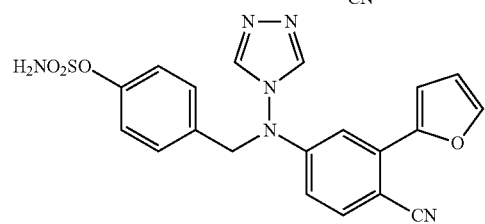
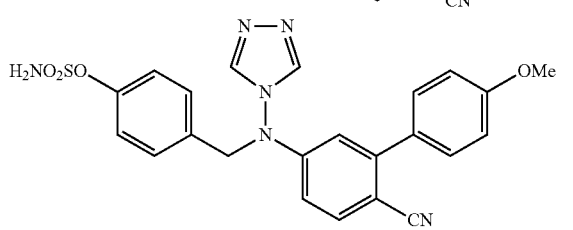
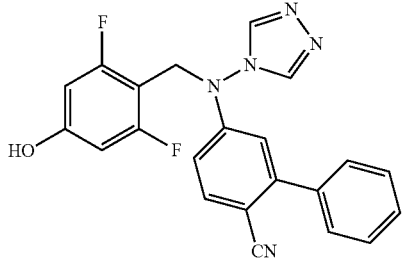
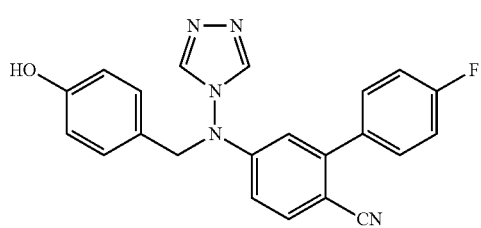
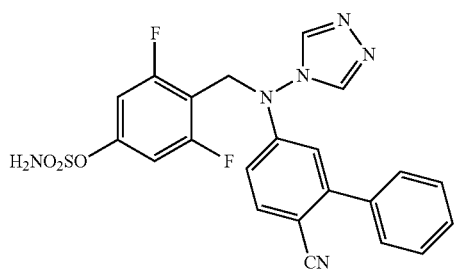
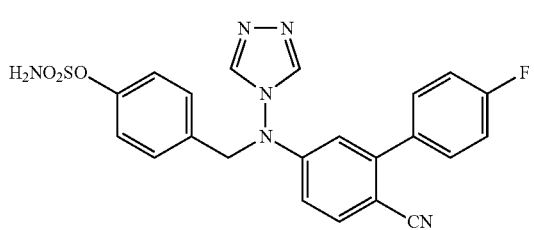
38
-continued
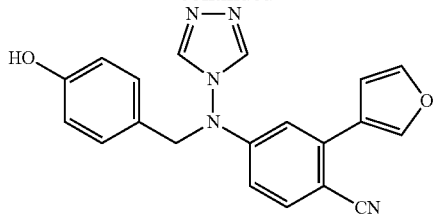
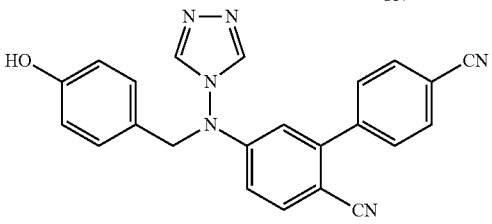
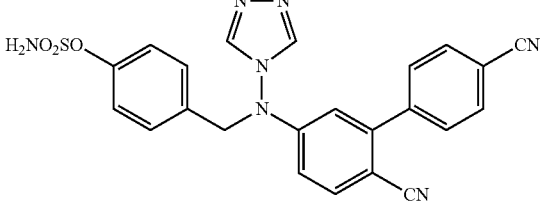
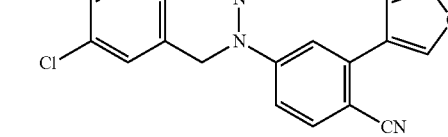
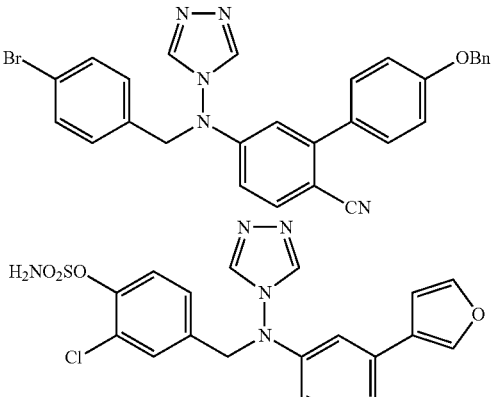
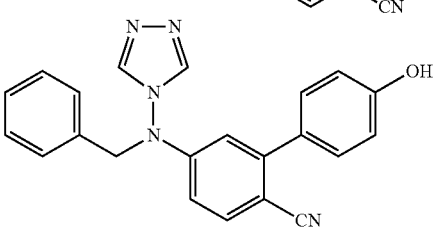

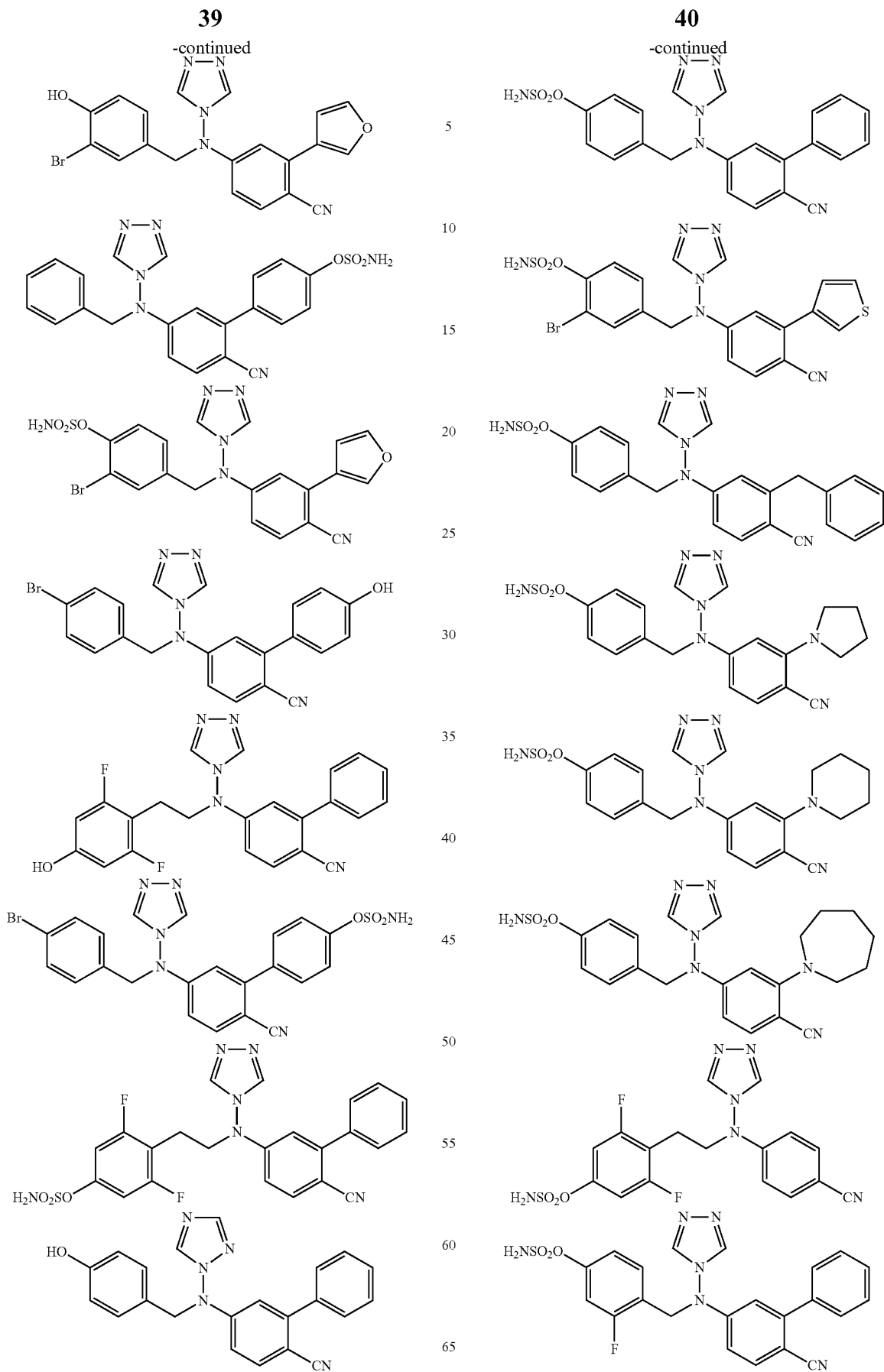

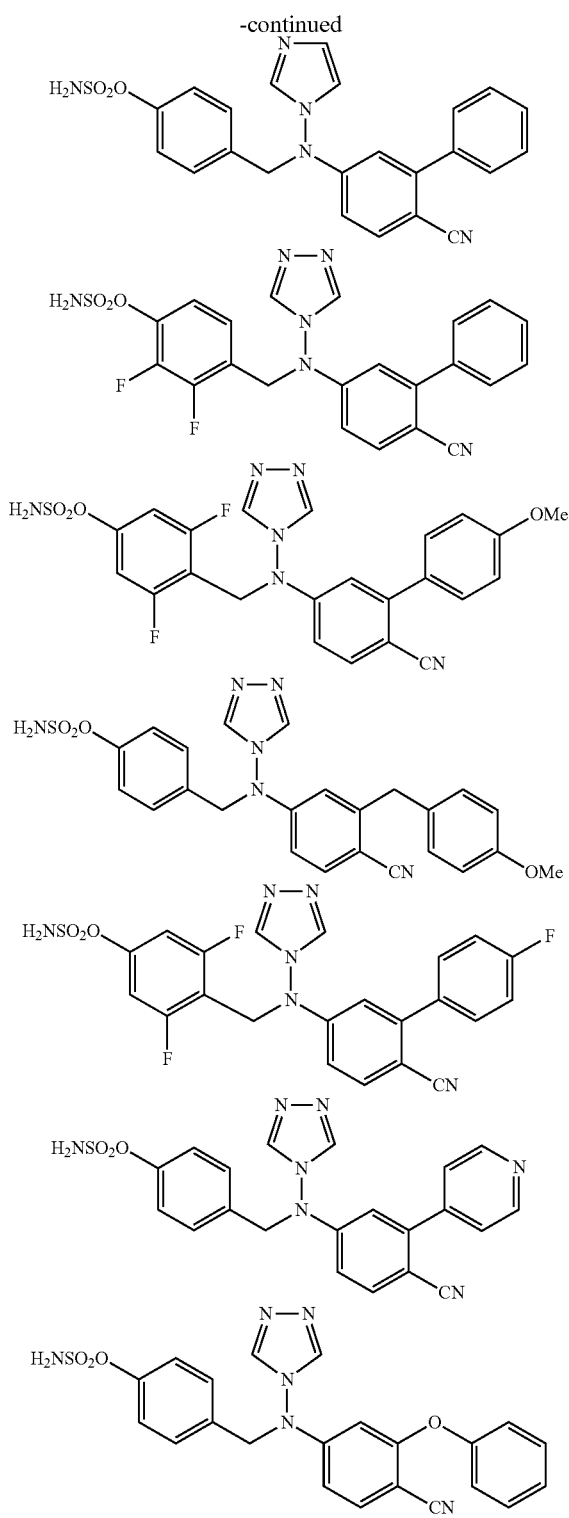

Further Aspects

The present invention also covers novel intermediates that are useful to prepare the compounds of the present invention For example, the present invention covers novel alcohol precursors for the compounds. By way of further example, the present invention covers bis protected precursors for the compounds Examples of each of these precursors are presented herein The present invention also encompasses a process comprising each or both of those precursors for the synthesis of the compounds of the present invention.

The present invention further provides

A compound as described herein for use in medicine.

A pharmaceutical composition comprising the compound as described herein optionally admixed with a pharmaceutically acceptable carrier, diluent, excipient or adjuvant.

A compound as described herein for use in the therapy of a condition or disease associated with STS and aromatase.

A compound as described herein for use in the therapy of a condition or disease associated with adverse STS levels and adverse aromatase levels.

A compound as described herein for inhibiting STS activity and/or inhibiting aromatase activity A compound as described herein for inhibiting aromatase activity.

A compound as described herein for inhibiting STS activity

A compound as described herein for inhibiting STS activity and inhibiting aromatase activity.

A compound as described herein for treating cancer.

Use of a compound as described herein in the manufacture of a medicament for use in the therapy of a condition or disease associated with STS and aromatase.

Use of a compound as described herein in the manufacture of a medicament for use in the therapy of a condition or disease associated with adverse STS levels and adverse aromatase levels.

Use of a compound as described herein in the manufacture of a medicament for inhibiting STS activity and/or inhibiting aromatase activity Use of a compound as described herein in the manufacture of a medicament for inhibiting aromatase activity.

Use of a compound as described herein in the manufacture of a medicament for inhibiting STS activity.

Use of a compound as described herein in the manufacture of a medicament for inhibiting STS activity and inhibiting aromatase activity.

Use of a compound as described herein in the manufacture of a medicament for treating cancer.

Use of a compound as described herein in the manufacture of a medicament for use in the therapy of a condition or disease associated with STS and/or aromatase and/or cell cycling and/or apoptosis and/or cell growth Use of a compound as described herein in the manufacture of a medicament for use in the therapy of a condition or disease associated with adverse STS levels and/or adverse aromatase levels and/or cell cycling and/or apoptosis and/or cell growth.

Steroid Sulphatase

Steroid sulphatase—which is sometimes referred to as steroid sulphatase or steryl sulphatase or "STS" for short—hydrolyses several sulphated steroids, such as oestrone sulphate, dehydroepiandrosterone sulphate and cholesterol sulphate. STS has been allocated the enzyme number EC 3.1.6.2.

STS has been cloned and expressed. For example see Stein et al (J Biol. Chem 264:13865-13872 (1989)) and Yen et al (Cell 49:443-454 (1987)).

STS is an enzyme that has been implicated in a number of disease conditions.

By way of example, workers have found that a total deficiency in STS produces ichthyosis. According to some workers, STS deficiency is fairly prevalent in Japan. The same workers (Sakura at al, J Inherit Metab Dis 1997 November; 20 (6):807-10) have also reported that allergic diseases—such as bronchial asthma, allergic rhinitis, or atopic dermatitis—may be associated with a steroid sulphatase deficiency In addition to disease states being brought on through a total lack of STS activity, an increased level of STS activity may also bring about disease conditions By way of example, and as indicated above, there is strong evidence to support a role of STS in breast cancer growth and metastasis.

STS has also been implicated in other disease conditions. By way of example, Le Roy at al (Behav Genet. 1999 March; 29 (2):131-6) have determined that there may be a genetic correlation between steroid sulphatase concentration and initiation of attack behaviour in mice. The authors conclude that sulphatation of steroids may be the prime mover of a complex network, including genes shown to be implicated in aggression by mutagenesis STS Inhibition It is believed that some disease conditions associated with STS activity are due to conversion of a nonactive, sulphated oestrone to an active, nonsulphated oestrone. In disease conditions associated with STS activity, it would be desirable to inhibit STS activity.

Here, the term "inhibit" includes reduce and/or eliminate and/or mask and/or prevent the detrimental action of STS STS Inhibitor In some aspects of the present invention, the compound may act as an STS inhibitor.

Here, the term "inhibitor" as used herein with respect to the compound of the present invention means a compound that can inhibit STS activity—such as reduce and/or eliminate and/or mask and/or prevent the detrimental action of STS. The STS inhibitor may act as an antagonist.

The ability of compounds to inhibit oestrone sulphatase activity can be assessed using either intact JEG3 choriocarcinoma cells or placental microsomes In addition, an animal model may be used. Details on suitable Assay Protocols are presented in following sections it is to be noted that other assays could be used to determine STS activity and thus STS inhibition For example, reference may also be made to the in teachings of WO-A-99/50453

In one aspect, for some applications, the compound is further characterised by the feature that if the sulphamate group were to be substituted by a sulphate group to form a sulphate derivative, then the sulphate derivative would be hydrolysable by an enzyme having steroid sulphatase (E.C 3.1.6.2) activity—i e when incubated with steroid sulphatase EC 3.1.6.2 at pH 7 4 and 37° C.

In one preferred embodiment, if the sulphamate group of the compound were to be replaced with a sulphate group to form a sulphate compound then that sulphate compound would be hydrolysable by an enzyme having steroid sulphatase (EC 3.1.6.2) activity and would yield a Km value of less than 200 mmolar, preferably less than 150 mmolar, preferably less than 100 mmolar, preferably less than 75 mmolar, preferably less than 50 mmolar, when incubated with steroid sulphatase EC 3.1.6.2 at pH 7.4 and 37° C.

In a preferred embodiment, the compound of the present invention is not hydrolysable by an enzyme having steroid sulphatase (EC. 3.1.6.2) activity.

For some applications, preferably the compound of the present invention has at least about a 100 fold selectivity to a desired target (e.g. STS and/or aromatase), preferably at least about a 150 fold selectivity to the desired target, preferably at least about a 200 fold selectivity to the desired target, preferably at least about a 250 fold selectivity to the desired target, preferably at least about a 300 fold selectivity to the desired target, preferably at least about a 350 fold selectivity to the desired target.

It is to be noted that the compound of the present invention may have other beneficial properties in addition to or in the alternative to its ability to inhibit STS and/or aromatase activity Other Substituents The compound of the present invention may have substituents other than those of formula I By way of example, these other substituents may be one or more of: one or more sulphamate group(s), one or more phosphonate group(s), one or more thiophosphonate group(s), one or more sulphonate group(s), one or more sulphonamide group(s), one or more halo groups, one or more O groups, one or more hydroxy groups, one or more amino groups, one or more sulphur containing group(s), one or more hydrocarbyl group(s)—such as an oxyhydrocarbyl group Assay for Determining STS Activity Using Cancer Cells Protocol 1

Inhibition of Steroid Sulphatase Activity in JEG3 Cells

Steroid sulphatase activity is measured in vitro using intact JEG3 choriocarcinoma cells. This cell line may be used to study the control of human breast cancer cell growth It possesses significant steroid sulphatase activity (Boivin et al, J. Med. Chem., 2000, 43: 4465-4478) and is available in from the American Type Culture Collection (ATCC).

Cells are maintained in Minimal Essential Medium (MEM) containing 20 mM HEPES, 5% foetal bovine serum, 2 mM glutamine, non-essential amino acids and 0.075% sodium bicarbonate. Up to 30 replicate 25 $cm^2$ tissue culture flasks are seeded with approximately $1\times10^5$ cells/flask using the above medium Cells are grown to 80% confluency and the medium is changed every third day.

Intact monolayers of JEG3 cells in triplicate 25 $cm^2$ tissue culture flasks are washed with Earle's Balanced Salt Solution (EBSS) and incubated for 3-4 hours at 37° C. with 5 pmol ($7\times10^5$ dpm) [6, 7-3H]oestrone-3-sulphate (specific activity 60 Ci/mmol) in serum-free MEM (2.5 ml) together with oestrone-3-sulphamate (11 concentrations: 0; 1fM; 0.01 pM; 0.1 pM, 1 pM; 0.01 nM; 0.1 nM; 0.01 mM; 0.1 mM; 1 mM). After incubation each flask is cooled and the medium (1 ml) is pipetted into separate tubes containing [14C]oestrone ($7\times103$ dpm) (specific activity 97 Ci/mmol). The mixture is shaken thoroughly for 30 seconds with toluene (5 ml) Experiments have shown that >90% [14C]oestrone and <0 1% [3H] oestrone-3-sulphate is removed from the aqueous phase by this treatment A portion (2 ml) of the organic phase is removed, evaporated and the 3H and 14C content of the residue determined by scintillation spectrometry The mass of oestrone-3-sulphate hydrolysed was calculated from the 3H counts obtained (corrected for the volumes of the medium and organic phase used, and for recovery of [14C] oestrone added) and the specific activity of the substrate Each batch of experiments includes incubations of microsomes prepared from a sulphatase-positive human placenta (positive control) and flasks without cells (to assess apparent non-enzymatic hydrolysis of the substrate). The number of cell nuclei per flask is determined using a Coulter Counter after treating the cell monolayers with Zaponin One flask in each batch is used to assess cell membrane status and viability using the Trypan Blue exclusion method (Phillips, H J. (1973) In: Tissue culture and applications, [eds: Kruse, D. F. & Patterson, M. K]; pp 406-408; Academic Press, New York)

Results for steroid sulphatase activity are expressed as the mean±1S.D. of the total product (oestrone+oestradiol)

formed during the incubation period (3-4 hours) calculated for 106 cells and, for values showing statistical significance, as a percentage reduction (inhibition) over incubations containing no oestrone-3-sulphamate. Unpaired Student's t-test was used to test the statistical significance of results Assay for Determining STS Activity Using Placental Microsomes Protocol 2

Inhibition of Steroid Sulphatase Activity in Placental Microsomes

Sulphatase-positive human placenta from normal term pregnancies are thoroughly minced with scissors and washed once with cold phosphate buffer (pH 7 4, 50 mM) then re-suspended in cold phosphate buffer (5 ml/g tissue). Homogenisation is accomplished with a homogeniser, using three 10 second bursts separated by 2 minute cooling periods in ice. Nuclei and cell debris are removed by centrifuging (4° C.) at 2000 g for 30 minutes and portions (2 ml) of the supernatant are stored at 20° C. The protein concentration of the supernatants is determined by the method of Bradford (Anal. Biochem, 72, 248-254 (1976)).

Incubations (1 ml) are carried out using a protein concentration of 100 mg/ml, substrate concentration of 20 mM [6, 7-3]oestrone-3-sulphate (specific activity 60 Ci/mmol) and an incubation time of 20 minutes at 37° C. If necessary eight concentrations of compounds are employed: 0 (i e control); 0.05 mM; 0.1 mM; 0.2 mM; 0.4 mM; 0.6 mM; 0.8 mM; 1.0 mM. After incubation each sample is cooled and the medium (1 ml) was pipetted into separate tubes containing [14C] oestrone (7×103 dpm) (specific activity 97 Ci/mmol) The mixture is shaken thoroughly for 30 seconds with toluene (5 ml). Experiments have shown that >90% [14C]oestrone and <0.1% [3H]oestrone-3-sulphate is removed from the aqueous phase by this treatment A portion (2 ml) of the organic phase was removed, evaporated and the 3H and 14C content of the residue determined by scintillation spectrometry. The mass of oestrone-3-sulphate hydrolysed is calculated from the 3H counts obtained (corrected for the volumes of the medium and organic phase used, and for recovery of [14C]oestrone added) and the specific activity of the substrate.

Animal Assay Model for Determining STS Activity

Protocol 3

Inhibition of Oestrone Sulphatase Activity In Vivo

The compounds of the present invention may be studied using an animal model, in particular in ovariectomised rats. In this model compounds which are oestrogenic stimulate uterine growth.

The compound (0 1 mg/Kg/day for five days) is administered orally to rats with another group of animals receiving vehicle only (propylene glycol) At the end of the study samples of liver tissue were obtained and oestrone sulphatase activity assayed using 3H oestrone sulphate as the substrate as previously described (see PCT/GB95/02638).

Animal Assay Model for Determining Oestrogenic Activity

Protocol 4

The compounds of the present invention may be studied using an animal model, in particular in ovariectomised rats. In this model, compounds which are oestrogenic stimulate uterine growth.

The compound (0 1 mg/Kg/day for five days) was administered orally to rats with another group of animals receiving vehicle only (propylene glycol) At the end of the study uteri were obtained and weighed with the results being expressed as uterine weight/whole body weight×100.

Compounds having no significant effect on uterine growth are not oestrogenic

Biotechnological Assays for Determining STS Activity

Protocol 5

The ability of compounds to inhibit oestrone sulphatase activity can also be assessed using amino acid sequences or nucleotide sequences encoding STS, or active fragments, derivatives, homologues or variants thereof in, for example, high-through put screens.

Any one or more of appropriate targets—such as an amino acid sequence and/or nucleotide sequence—may be used for identifying an agent capable of modulating STS in any of a variety of drug screening techniques. The target employed in such a test may be free in solution, affixed to a solid support, borne on a cell surface, or located intracellularly. The abolition of target activity or the formation of binding complexes between the target and the agent being tested may be measured The assay of the present invention may be a screen, whereby a number of agents are tested In one aspect, the assay method of the present invention is a high throughput screen.

Techniques for drug screening may be based on the method described in Geysen, European Patent Application 84/03564, published on Sep. 13, 1984. In summary, large numbers of different small peptide test compounds are synthesised on a solid substrate, such as plastic pins or some other surface. The peptide test compounds are reacted with a suitable target or fragment thereof and washed Bound entities are then detected—such as by appropriately adapting methods well known in the art A purified target can also be coated directly onto plates for use in a drug screening techniques. Alternatively, non-neutralising antibodies can be used to capture the peptide and immobilise it on a solid support This invention also contemplates the use of competitive drug screening assays in which neutralising antibodies capable of binding a target specifically compete with a test compound for binding to a target Another technique for screening provides for high throughput screening (HTS) of agents having suitable binding affinity to the substances and is based upon the method described in detail in WO 84/03564

It is expected that the assay methods of the present invention will be suitable for both small and large-scale screening of test compounds as well as in quantitative assays In one preferred aspect, the present invention relates to a method of identifying agents that selectively modulate STS, which compounds have the formula (I)

Assay for Determining Aromatase Activity Using JEG3 Cells

Protocol 6

Aromatase activity is measured in JEG3 choriocarcinoma cells, obtained from the ATCC. This cell line possesses significant aromatase activity and is widely used to study the control of human aromatase activity (Bhatnager et al, J Steroid Biochem Molec. Biol 2001, 76: 199-202). Cells are maintained in Minimal Essential Medium (MEM) containing 20 mM HEPES, 10% foetal bovine serum, 2 mM glutamine, non-essential amino acids and 0.075% sodium bicarbonate Intact monolayers of JEG3 cells ($2.5 \times 10^6$ cells) in triplicate 25 cm$^2$ tissue culture flasks are washed with Earle's Balanced salt solution (EBSS) and incubated with [1β-$^3$H]androstenedione (2-5 nM, 26 Ci/mmol) for 30 min with inhibitors over the range of 10 pm-10 μM. During the aromatase reaction, $^3$H$_2$O is liberated which can be quantified using a liquid scintillation spectrometer. This $^3$H$_2$O-release method has been widely used to measure aromatase activity (Newton at al., J. Steroid Biochem 1986, 24: 1033-1039). The number of cell nuclei per flask is determined using a Coulter Counter after treating the cell monolayers with Zaponin.

Results for aromatase activity are expressed as the mean±1S D. of the product formed during the incubation period (30 min) calculated for 10$^6$ cells and, for values showing a statistical significance, as a percentage reduction (inhibition) over incubations containing no aromatase inhibitor. Unpaired Student's t test was used to test the statistical significance of results IC$_{50}$ values were calculated as the concentration of inhibitor required to obtain a 50% inhibition of aromatase activity.

Animal Assays for Determining Aromatase Activity

Protocol 7

(i) Inhibition of PMSG-Induced Oestrogen Synthesis

The ability of compounds to inhibit aromatase activity in vivo was tested using a pregnant mare serum gonadotrophin (PMSG)-induced oestrogen synthesis assay. For this, female rats (250 g) were injected with PMSG (200 IU, s c. After 72 h rats were administered vehicle (propylene glycol) or various doses of test compounds orally At 2 h after dosing blood samples were obtained by cardiac puncture (under anaesthesia). Plasma oestradiol levels were measured in control groups and groups receiving drugs The efficacy of aromatase inhibition was determined by measurement of plasma oestradiol concentrations by radioimmunoassay. This method has been widely used to determine the effectiveness of aromatase inhibitors in vivo (Wouters et al, J Steroid Biochem., 1989, 32: 781-788)

(ii) Inhibition of Androstenedione Stimulated Uterine Growth in Ovariectomised Rats Female rats (250 g) were ovariectomised and used to determine the effectiveness of aromatase inhibition on androstenedione stimulated uterine growth. Administration of androstenedione (30 mg/kg/d) for a 2-week period results in a significant increase in uterine growth in ovariectomised animals. This increase in uterine growth is stimulated by oestrogen which is derived from the administered androstenedione as a result of the action of the aromatase enzyme. By co-administration of compounds with androstenedione the extent of aromatase inhibition can be determined by measurements of uterine weights in treated and untreated animals Therapy The compounds of the present invention may be used as therapeutic agents—i.e in therapy applications.

The term "therapy" includes curative effects, alleviation effects, and prophylactic effects The therapy may be on humans or animals, preferably female animals Pharmaceutical Compositions In one aspect, the present invention provides a pharmaceutical composition, which comprises a compound according to the present invention and optionally a pharmaceutically acceptable carrier, diluent or excipient (including combinations thereof).

The pharmaceutical compositions may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co (A. R Gennaro edit. 1985) The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Preservatives, stabilisers, dyes and even flavouring agents may be provided in the pharmaceutical composition Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition of the present invention may be formulated to be delivered using a mini-pump or by a mucosal route, for example, as a nasal spray or aerosol for inhalation or ingestable solution, or parenterally in which the composition is formulated by an injectable form, for delivery, by, for example, an intravenous, intramuscular or subcutaneous route Alternatively, the formulation may be designed to be delivered by both routes.

Where the agent is to be delivered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner Combination Pharmaceutical The compound of the present invention may be used in combination with one or more other active agents, such as one or more other pharmaceutically active agents By way of example, the compounds of the present invention may be used in combination with other STS inhibitors and/or other inhibitors such as an aromatase inhibitor (such as for example, 4-hydroxyandrostenedione (4-DHA)) and/or steroids—such as the naturally occurring neurosteroids dehydroepiandrosterone sulfate (DHEAS) and pregnenolone sulfate (PS) and/or other structurally similar organic compounds. Examples of other STS inhibitors may be found in the above references In addition, or in the alternative, the compound of the present invention may be used in combination with a biological response modifier The term biological response modifier ("BRM") includes cytokines, immune modulators, growth factors, haematopoiesis regulating factors, colony stimulating factors, chemotactic, haemolytic and thrombolytic factors, cell surface receptors, ligands, leukocyte adhesion molecules, monoclonal antibodies, preventative and therapeutic vaccines, hormones, extracellular matrix components, fibronectin, etc For some applications, preferably, the biological response modifier is a cytokine. Examples of cytokines include: interleukins (IL)—such as IL-1, IL-2, IL-3, IL-4, IL-5, IL-6, IL-7, IL-8, IL-9, IL-10, IL-11, IL-12, IL-19, Tumour Necrosis Factor (TNF)—such as TNF-α; Interferon alpha, beta and gamma; TGF-β. For some applications, preferably the cytokine is tumour necrosis factor (TNF) For some applications, the TNF may be any type of TNF—such as TNF-α, TNF-β, including derivatives or mixtures thereof. More preferably the cytokine is TNF-α. Teachings on TNF may be found in the art—such as WO-A-98/08870 and WO-A-98/13348

Administration

Typically, a physician will determine the actual dosage which will be most suitable for an individual subject and it will vary with the age, weight and response of the particular patient. The dosages below are exemplary of the average case. There can, of course, be individual instances where higher or lower dosage ranges are merited.

The compositions of the present invention may be administered by direct injection. The composition may be formulated for parenteral, mucosal, intramuscular, intravenous, subcutaneous, intraocular or transdermal administration. Depending upon the need, the agent may be administered at a dose of from 0.01 to 30 mg/kg body weight, such as from 0.1 to 10 mg/kg, more preferably from 0.1 to 1 mg/kg body weight.

By way of further example, the agents of the present invention may be administered in accordance with a regimen of 1 to 4 times per day, preferably once or twice per day. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Aside from the typical modes of delivery—indicated above—the term "administered" also includes delivery by techniques such as lipid mediated transfection, liposomes, immunoliposomes, lipofectin, cationic facial amphiphiles (CFAs) and combinations thereof. The routes for such delivery mechanisms include but are not limited to mucosal, nasal, oral, parenteral, gastrointestinal, topical, or sublingual routes The term "administered" includes but is not limited to delivery by a mucosal route, for example, as a nasal spray or aerosol for inhalation or as an ingestable solution; a parenteral route where delivery is by an injectable form, such as, for example, an intravenous, intramuscular or subcutaneous route Thus, for pharmaceutical administration, the STS inhibitors of the present invention can be formulated in any suitable manner utilising conventional pharmaceutical formulating techniques and pharmaceutical carriers, adjuvants, excipients, diluents etc and usually for parenteral administration Approximate effective dose rates may be in the range from 1 to 1000 mg/day, such as from 10 to 900 mg/day or even from 100 to 800 mg/day depending on the individual activities of the compounds in question and for a patient of average (70 Kg) bodyweight. More usual dosage rates for the preferred and more active compounds will be in the range 200 to 800 mg/day, more preferably, 200 to 500 mg/day, most preferably from 200 to 250 mg/day. They may be given in single dose regimes, split dose regimes and/or in multiple dose regimes lasting over several days. For oral administration they may be formulated in tablets, capsules, solution or suspension containing from 100 to 500 mg of compound per unit dose. Alternatively and preferably the compounds will be formulated for parenteral administration in a suitable parenterally administrable carrier and providing single daily dosage rates in the range 200 to 800 mg, preferably 200 to 500, more preferably 200 to 250 mg. Such effective daily doses will, however, vary depending on inherent activity of the active ingredient and on the bodyweight of the patient, such variations being within the skill and judgement of the physician.

Cell Cycling

The compounds of the present invention may be useful in the method of treatment of a cell cycling disorder As discussed in "Molecular Cell Biology" 3rd Ed Lodish of al. pages 177-181 different eukaryotic cells can grow and divide at quite different rates Yeast cells, for example, can divide every 120 min and the first divisions of fertilised eggs in the embryonic cells of sea urchins and insects take only 1530 min because one large pre-existing cell is subdivided. However, most growing plant and animal cells take 10-20 hours to double in number, and some duplicate at a much slower rate. Many cells in adults, such as nerve cells and striated muscle cells, do not divide at all; others, like the fibroblasts that assist in healing wounds, grow on demand but are otherwise quiescent.

Still, every eukaryotic cell that divides must be ready to donate equal genetic material to two daughter cells. DNA synthesis in eukaryotes does not occur throughout the cell division cycle but is restricted to a part of it before cell division.

The relationship between eukaryotic DNA synthesis and cell division has been thoroughly analysed in cultures of mammalian cells that were all capable of growth and division. In contrast to bacteria, it was found, eukaryotic cells spend only a part of their time in DNA synthesis, and it is completed hours before cell division (mitosis). Thus a gap of time occurs after DNA synthesis and before cell division; another gap was found to occur after division and before the next round of DNA synthesis. This analysis led to the conclusion that the eukaryotic cell cycle consists of an M (mitotic) phase, a $G_1$ phase (the first gap), the S (DNA synthesis) phase, a $G_2$ phase (the second gap), and back to M. The phases between mitoses ($G_1$, S, and $G_2$) are known collectively as the interphase.

Many nondividing cells in tissues (for example, all quiescent fibroblasts) suspend the cycle after mitosis and just prior to DNA synthesis; such "resting" cells are said to have exited from the cell cycle and to be in the $G_0$ state.

It is possible to identify cells when they are in one of the three interphase stages of the cell cycle, by using a fluorescence-activated cell sorter (FACS) to measure their relative DNA content: a cell that is in $G_1$ (before DNA synthesis) has a defined amount x of DNA, during S (DNA replication), it has between x and 2x; and when in $G_2$ (or M), it has 2x of DNA.

The stages of mitosis and cytokinesis in an animal cell are as follows (a) Interphase The $G_2$ stage of interphase immediately precedes the beginning of mitosis. Chromosomal DNA has been replicated and bound to protein during the S phase, but chromosomes are not yet seen as distinct structures. The nucleolus is the only nuclear substructure that is visible under light microscope In a diploid cell before DNA replication there are two morphologic chromosomes of each type, and the cell is said to be 2n. In $G_2$, after DNA replication, the cell is 4n. There are four copies of each chromosomal DNA. Since the sister chromosomes have not yet separated from each other, they are called sister chromatids.

b) Early prophase Centrioles, each with a newly formed daughter centriole, begin moving toward opposite poles of the cell, the chromosomes can be seen as long threads The nuclear membrane begins to disaggregate into small vesicles.

(c) Middle and late prophase. Chromosome condensation is completed; each visible chromosome structure is composed of two chromatids held together at their centromeres Each chromatid contains one of the two newly replicated daughter DNA molecules The microtubular spindle begins to radiate from the regions just adjacent to the centrioles, which are moving closer to their poles Some spindle fibres reach from pole to pole, most go to chromatids and attach at kinetochores.

(d) Metaphase. The chromosomes move toward the equator of the cell, where they become aligned in the equatorial plane. The sister chromatids have not yet separated (e) Anaphase. The two sister chromatids separate into independent chromosomes. Each contains a centromere that is linked by a spindle fibre to one pole, to which it moves. Thus one copy of each chromosome is donated to each daughter cell Simultaneously, the cell elongates, as do the pole-to-pole spindles. Cytokinesis begins as the cleavage furrow starts to form.

(f) Telophase New membranes form around the daughter nuclei; the chromosomes uncoil and become less distinct, the nucleolus becomes visible again, and the nuclear membrane forms around each daughter nucleus. Cytokinesis is nearly complete, and the spindle disappears as the microtubules and other fibres depolymerise. Throughout mitosis the "daughter" centriole at each pole grows until it is full-length. At telophase the duplication of each of the original centrioles is completed, and new daughter centrioles will be generated during the next interphase (g) Interphase. Upon the completion of cytokinesis, the cell enters the $G_1$ phase of the cell cycle and proceeds again around the cycle.

It will be appreciated that cell cycling is an extremely important cell process. Deviations from normal cell cycling can result in a number of medical disorders. Increased and/or unrestricted cell cycling may result in cancer Reduced cell cycling may result in degenerative conditions Use of the compound of the present invention may provide a means to treat such disorders and conditions Thus, the compound of the present invention may be suitable for use in the treatment of cell cycling disorders such as cancers, including hormone dependent and hormone independent cancers In addition, the compound of the present invention may be suitable for the treatment of cancers such as breast cancer, ovarian cancer, endometrial cancer, sarcomas, melanomas, prostate cancer, pancreatic cancer etc and other solid tumours.

For some applications, cell cycling is inhibited and/or prevented and/or arrested, preferably wherein cell cycling is prevented and/or arrested. In one aspect cell cycling may be inhibited and/or prevented and/or arrested in the $G_2$/M phase. In one aspect cell cycling may be irreversibly prevented and/or inhibited and/or arrested, preferably wherein cell cycling is irreversibly prevented and/or arrested.

By the term "irreversibly prevented and/Dr inhibited and/or arrested" it is meant after application of a compound of the present invention, on removal of the compound the effects of the compound, namely prevention and/or inhibition and/or arrest of cell cycling, are still observable. More particularly by the term "irreversibly prevented and/or inhibited and/or arrested" it is meant that when assayed in accordance with the cell cycling assay protocol presented herein, cells treated with a compound of interest show less growth after Stage 2 of Protocol 7 than control cells. Details of this protocol are presented below.

Thus, the present invention provides compounds which: cause inhibition of growth of oestrogen receptor positive (ER+) and ER negative (ER−) breast cancer cells in vitro by preventing and/or inhibiting and/or arresting cell cycling; and/or cause regression of nitroso-methyl urea (NMU)-Induced mammary tumours in intact animals (i.e. not ovariectomised), and/or prevent and/or inhibit and/or arrest cell cycling in cancer cells; and/or act in vivo by preventing and/or inhibiting and/or arresting cell cycling and/or act as a cell cycling agonist.

Cell Cycling Assay

Protocol 7

Procedure

Stage 1

MCF-7 breast cancer cells are seeded into multi-well culture plates at a density of 105 cells/well. Cells were allowed to attach and grown until about 30% confluent when they are treated as follows.

Control—No Treatment

Compound of Interest (COI) 20 µM

Cells are grown for 6 days in growth medium containing the COI with changes of medium/COI every 3 days At the end of this period cell numbers were counted using a Coulter cell counter.

Stage 2

After treatment of cells for a 6-day period with the COI cells are re-seeded at a density of $10^4$ cells/well No further treatments are added. Cells are allowed to continue to grow for a further 6 days in the presence of growth medium. At the end of this period cell numbers are again counted.

Cancer

As indicated, the compounds of the present invention may be useful in the treatment of a cell cycling disorder. A particular cell cycling disorder is cancer.

Cancer remains a major cause of mortality in most Western countries Cancer therapies developed so far have Included blocking the action or synthesis of hormones to inhibit the growth of hormone-dependent tumours. However, more aggressive chemotherapy is currently employed for the treatment of hormone-independent tumours Hence, the development of a pharmaceutical for anti-cancer treatment of hormone dependent and/or hormone independent tumours, yet lacking some or all of the side-effects associated with chemotherapy, would represent a major therapeutic advance.

It is known that oestrogens undergo a number of hydroxylation and conjugation reactions after their synthesis. Until recently it was thought that such reactions were part of a metabolic process that ultimately rendered oestrogens water soluble and enhanced their elimination from the body. It is now evident that some hydroxy metabolites (e.g. 2-hydroxy and 16alpha-hydroxy) and conjugates (e.g. oestrone sulphate, E1S) are important in determining some of the complex actions that oestrogens have in the body.

Workers have investigated the formation of 2- and 16 hydroxylated oestrogens in relation to conditions that alter the risk of breast cancer. There is now evidence that to factors which increase 2-hydroxylase activity are associated with a reduced cancer risk, while those increasing 16alpha-hydroxylation may enhance the risk of breast cancer Further interest in the biological role of estrogen metabolites has been stimulated by the growing body of evidence that 2-methoxyoestradiol is an endogenous metabolite with anti-mitotic properties. 2-MeOE2 is formed from 2-hydroxy estradiol (2-OHE2) by catechol estrogen methyl transferase, an enzyme that is widely distributed throughout the body.

Workers have shown that in vivo 2-MeOE2 inhibits the growth of tumours arising from the subcutaneous injection of Meth A sarcoma, B16 melanoma or MDA-MB-435 estrogen receptor negative (ER−) breast cancer cells. It also inhibits endothelial cell proliferation and migration, and in vitro angiogenesis. It was suggested that the ability of 2-MeOE2 to inhibit tumour growth in vivo may be due to its ability to inhibit tumour-induced angiogenesis rather than direct inhibition of the proliferation of tumour cells.

The mechanism by which 2-MeOE2 exerts its potent anti-mitogenic and anti-angiogenic effects is still being elucidated. There is evidence that at high concentrations it can inhibit microtubule polymerisation and act as a weak inhibitor of colchicine binding to tubulin. Recently, however, at concentrations that block mitosis, tubulin filaments in cells were not found to be depolymerised but to have an identical morphology to that seen after taxol treatment. It is possible, therefore, that like taxol, a drug that is used for breast and ovarian breast cancer therapy, 2-MeOE2 acts by stabilising microtubule dynamics.

While the identification of 2-MeOE2 as a new therapy for cancer represents an important advance, the bioavailability of orally administered oestrogens is poor. Furthermore, they can undergo extensive metabolism during their first pass through the liver. As part of a research programme to develop a steroid sulphatase inhibitor for breast cancer therapy, oestrone-3-O-sulphamate (EMATE) was identified as a potent active site-directed inhibitor. Unexpectedly, EMATE proved to possess potent oestrogenic properties with its oral uterotrophic activity in rats being 100-times higher than that of estradiol. Its enhanced oestrogenicity is thought to result from its absorption by red blood cells (rbcs) which protects it from inactivation during its passage through the liver and which act as a reservoir for its slow release for a prolonged period of time. A number of A-ring modified analogues were synthesised and tested, including 2-methoxyoestrone-3-O-sulphamate While this compound was equipotent with EMATE as a steroid sulphatase inhibitor, it was devoid of oestrogenicity.

The compound of the present invention may provide a means for the treatment of cancers and, especially, breast cancer In addition or in the alternative the compound of the present invention may be useful in the blocking the growth of cancers including leukaemias and solid tumours such as breast, endometrium, prostate, ovary and pancreatic tumours Therapy Concerning Oestrogen Some of the compounds of the present invention may be useful in the control of oestrogen levels in the body—in particular in females. Thus, some of the compounds may be useful as providing a means of fertility control—such as an oral contraceptive tablet, pill, solution or lozenge. Alternatively, the compound could be in the form of an implant or as a patch.

Thus, the compounds of the present invention may be useful in treating hormonal conditions associated with oestrogen.

In addition or in the alternative the compound of the present invention may be useful in treating hormonal conditions in addition to those associated with oestrogen. Hence, the compound of the present invention may also be capable of affecting hormonal activity and may also be capable of affecting an immune response.

Neurodegenerative Diseases

The compounds of the present invention may be useful in the treatment of neurodenerative diseases, and similar conditions By way of example, it is believed that STS inhibitors may be useful in the enhancing the memory function of patients suffering from illnesses such as amnesia, head injuries, Alzheimer's disease, epileptic dementia, presenile dementia, post traumatic dementia, senile dementia, vascular dementia and post-stroke dementia or individuals otherwise seeking memory enhancement.

TH1

Some of the compounds of the present invention may be useful in TH1 implications By way of example, it is believed that the presence of STS inhibitors within the macrophage or other antigen presenting cells may lead to a decreased ability of sensitised T cells to mount a TH1 (high IL-2, IFNγ low IL-4) response. The normal regulatory influence of other steroids such as glucocorticoids would therefore predominate.

Inflamatory Conditions

Some of the compounds of the present invention may be useful in treating inflammatory conditions—such as conditions associated with any one or more of: autoimmunity, including for example, rheumatoid arthritis, type I and II diabetes, systemic lupus erythematosus, multiple sclerosis, myasthenia gravis, thyroiditis, vasculitis, ulcerative colitis and Crohn's disease, skin disorders e.g. psoriasis and contact dermatitis; graft versus host disease; eczema; asthma and organ rejection following transplantation By way of example, it is believed that STS inhibitors may prevent the normal physiological effect of DHEA or related steroids on immune and/or inflammatory responses The compounds of the present invention may be useful in the manufacture of a medicament for revealing an endogenous glucocorticoid-like effect.

Other Therapies

It is also to be understood that the compound/composition of the present invention may have other important medical indications.

For example, the compound or composition of the present invention may be useful in the treatment of the disorders listed in WO-A-99/52890-viz:

In addition, or in the alternative, the compound or composition of the present invention may be useful in the treatment of the disorders listed in WO-A-98/05635. For ease of reference, part of that list is now provided: cancer, inflammation or inflammatory disease, dermatological disorders, fever, cardiovascular effects, haemorrhage, coagulation and acute phase response, cachexia, anorexia, acute infection, HIV infection, shock states, graft-versus-host reactions, autoimmune disease, reperfusion injury, meningitis, migraine and aspirin-dependent anti-thrombosis; tumour growth, invasion and spread, angiogenesis, metastases, malignant, ascites and malignant pleural effusion; cerebral ischaemia, ischaemic heart disease, osteoarthritis, rheumatoid arthritis, osteoporosis, asthma, multiple sclerosis, neurodegeneration, Alzheimer's disease, atherosclerosis, stroke, vasculitis, Crohn's disease and ulcerative colitis; periodontitis, gingivitis; psoriasis, atopic dermatitis, chronic ulcers, epidermolysis bullosa; corneal ulceration, retinopathy and surgical wound healing; rhinitis, allergic conjunctivitis, eczema, anaphylaxis; restenosis, congestive heart failure, endometriosis, atherosclerosis or endosclerosis.

In addition, or in the alternative, the compound or composition of the present invention may be useful in the treatment of disorders listed in WO-A-98/07859. For ease of reference, part of that list is now provided: cytokine and cell proliferation/differentiation activity; immunosuppressant or immunostimulant activity (e.g. for treating immune deficiency, including infection with human immune deficiency virus; regulation of lymphocyte growth, treating cancer and many autoimmune diseases, and to prevent transplant rejection or induce tumour immunity); regulation of haematopoiesis, e.g. treatment of myeloid or lymphoid diseases; promoting growth of bone, cartilage, tendon, ligament and nerve tissue, e.g. for healing wounds, treatment of burns, ulcers and periodontal disease and neurodegeneration; inhibition or activation of follicle-stimulating hormone (modulation of fertility); chemotactic/chemokinetic activity (e.g. for mobilising specific cell types to sites of injury or infection); haemostatic and thrombolytic activity (e.g. for treating haemophilia and stroke); antiinflammatory activity (for treating e.g. septic shock or Crohn's disease); as antimicrobials, modulators of e.g. metabolism or behaviour; as analgesics; treating specific deficiency disorders; in treatment of e.g. psoriasis, in human or veterinary medicine.

In addition, or in the alternative, the composition of the present invention may be useful in the treatment of disorders listed in WO-A-98/09985. For ease of reference, part of that list is now provided: macrophage inhibitory and/or T cell inhibitory activity and thus, anti-inflammatory activity, anti-immune activity, i.e. inhibitory effects against a cellular and/or humoral immune response, including a response not associated with inflammation; inhibit the ability of macrophages and T cells to adhere to extracellular matrix components and fibronectin, as well as up-regulated fas receptor expression in T cells; inhibit unwanted immune reaction and inflammation including arthritis, including rheumatoid arthritis, inflammation associated with hypersensitivity, allergic reactions, asthma, systemic lupus erythematosus, collagen diseases and other autoimmune diseases, inflammation associated with atherosclerosis, arteriosclerosis, atherosclerotic heart disease, reperfusion injury, cardiac arrest, myocardial infarction, vascular inflammatory disorders, respiratory distress syndrome or other cardiopulmonary diseases, inflammation associated with peptic ulcer, ulcerative colitis and other diseases of the gastrointestinal tract, hepatic fibrosis, liver cirrhosis or other hepatic diseases, thyroiditis or other glandular diseases, glomerulonephritis or other renal and urologic diseases, otitis or other oto-rhino-laryngological diseases, dermatitis or other dermal diseases, periodontal diseases or other dental diseases, orchitis or epididimo-orchitis, infertility, orchidal trauma or other immune-related testicular diseases, placental dysfunction, placental insufficiency, habitual abortion, eclampsia, pre-eclampsia and other immune and/or inflammatory-related gynaecological diseases, posterior uveitis, intermediate uveitis, anterior uveitis, conjunctivitis, chorioretinitis, uveoretinitis, optic neuritis, intraocular inflammation, e.g. retinitis or cystoid macular oedema, sympathetic ophthalmia, scleritis, retinitis pigmentosa, immune and inflammatory components of degenerative fondus disease, inflammatory components of ocular trauma, ocular inflammation caused by infection, proliferative vitreo-retinopathies, acute ischaemic optic neuropathy, excessive scarring, e.g. following glaucoma filtration operation, immune and/or inflammation reaction against ocular implants and other immune and inflammatory-related ophthalmic diseases, inflammation associated with autoimmune diseases or conditions or disorders where, both in the central nervous system (CNS) or in any other organ, immune and/or inflammation suppression would be beneficial, Parkinson's disease, complication and/or side effects from treatment of Parkinson's disease, AIDS-related dementia complex HIV-related encephalopathy, Devic's disease, Sydenham chorea, Alzheimer's disease and other degenerative diseases, conditions or disorders of the CNS, inflammatory components of stokes, post-polio syndrome, immune and inflammatory components of psychiatric disorders, myelitis, encephalitis, subacute sclerosing pan-encephalitis, encephalomyelitis, acute neuropathy, subacute neuropathy, chronic neuropathy, Guillaim-Barre syndrome, Sydenham chore, myasthenia gravis, pseudo-tumour cerebri, Down's Syndrome, Huntington's disease, amyotrophic lateral sclerosis, inflammatory components of CNS compression or CNS trauma or infections of the CNS, inflammatory components of muscular atrophies and dystrophies, and immune and inflammatory related diseases, conditions or disorders of the central and peripheral nervous systems, post-traumatic inflammation, septic shock, infectious diseases, inflammatory complications or side effects of surgery, bone marrow transplantation or other transplantation complications and/or side effects, inflammatory and/or immune complications and side effects of gene therapy, e.g. due to infection with a viral carrier, or inflammation associated with AIDS, to suppress or inhibit a humoral and/or cellular immune response, to treat or ameliorate monocyte or leukocyte proliferative diseases, e.g. leukaemia, by reducing the amount of monocytes or lymphocytes, for the prevention and/or treatment of graft rejection in cases of transplantation of natural or artificial cells, tissue and organs such as cornea, bone marrow, organs, lenses, pacemakers, natural or artificial skin tissue Compound Preparation The compounds of the present invention may be prepared by reacting an appropriate alcohol with a suitable chloride.

By way of example, the sulphamate compounds of the present invention may be prepared by reacting an appropriate alcohol with a suitable sulfamoyl chloride, of the formula $R^{15}R^{16}NSO_2Cl$.

Typical conditions for carrying out the reaction are as follows.

Sodium hydride and a sulfamoyl chloride are added to a stirred solution of the alcohol in anhydrous dimethyl formamide at 0° C. Subsequently, the reaction is allowed to warm to room temperature whereupon stirring is continued for a further 24 hours. The reaction mixture is poured onto a cold saturated solution of sodium bicarbonate and the resulting aqueous phase is extracted with dichloromethane. The combined organic extracts are dried over anhydrous $MgSO_4$. Filtration followed by solvent evaporation in vacuo and co-evaporated with toluene affords a crude residue which is further purified by flash chromatography.

Preferably, the alcohol is derivatised, as appropriate, prior to reaction with the sulfamoyl chloride Where necessary, functional groups in the alcohol may be protected in known manners and the protecting group or groups removed at the end of the reaction Preferably, the sulphamate compounds are prepared according to the teachings of Page at al (1990 Tetrahedron 46; 2059-2068).

The phosphonate compounds may be prepared by suitably combining the teachings of Page et al (1990 Tetrahedron 46; 2059-2068) and PCT/GB92/01586.

The sulphonate compounds may be prepared by suitably adapting the teachings of Page at al (1990 Tetrahedron 46; 2059-2068) and PCT/GB92/01586.

The thiophosphonate compounds may be prepared by suitably adapting the teachings of Page at al (1990 Tetrahedron 46; 2059-2068) and PCT/GB91/00270.

Preferred preparations are also presented in the following text.

SUMMARY in summation, the present invention provides novel compounds for use as steroid sulphatase inhibitors and/or aromatase inhibitors and/or modulators of apoptosis and/or modulators of cell cycling and/or cell growth, and pharmaceutical compositions containing them.

The compounds of the present invention may be prepared in accordance with the general synthetic schemes given below and in accordance with the examples of compounds of the present invention described thereafter.

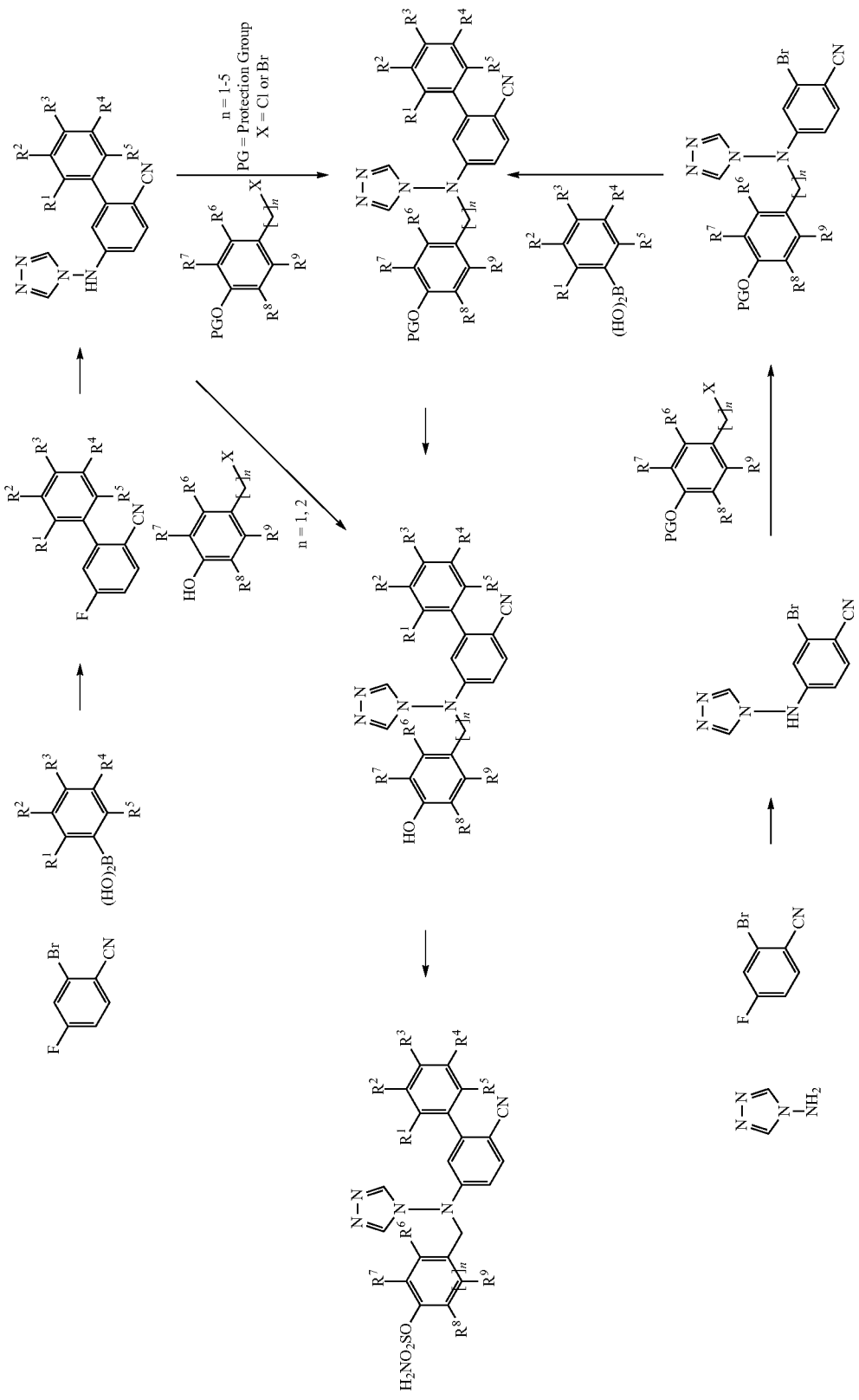
Scheme 1 General synthetic route for preparing derivatives with substituted biphenyls.

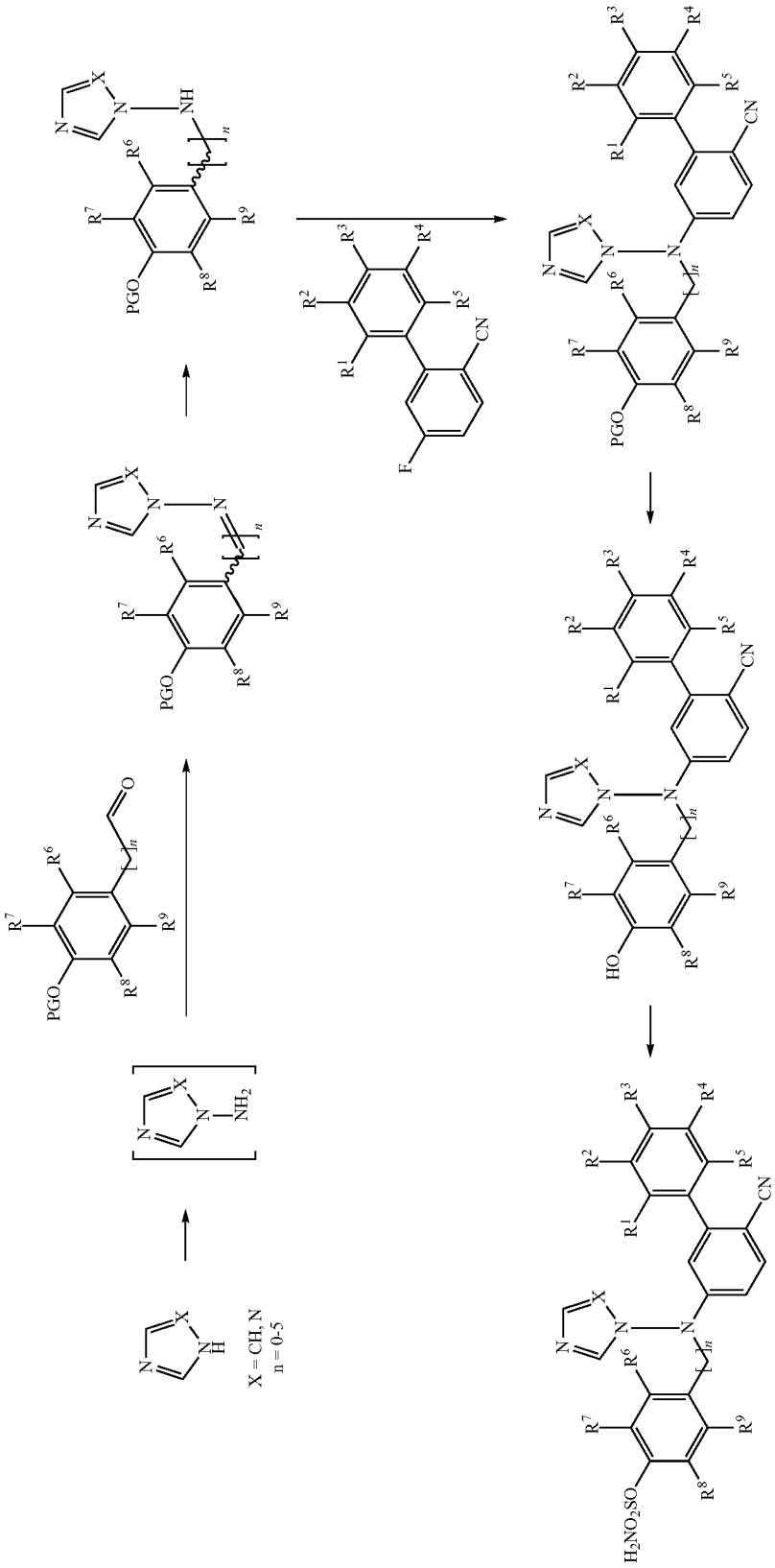

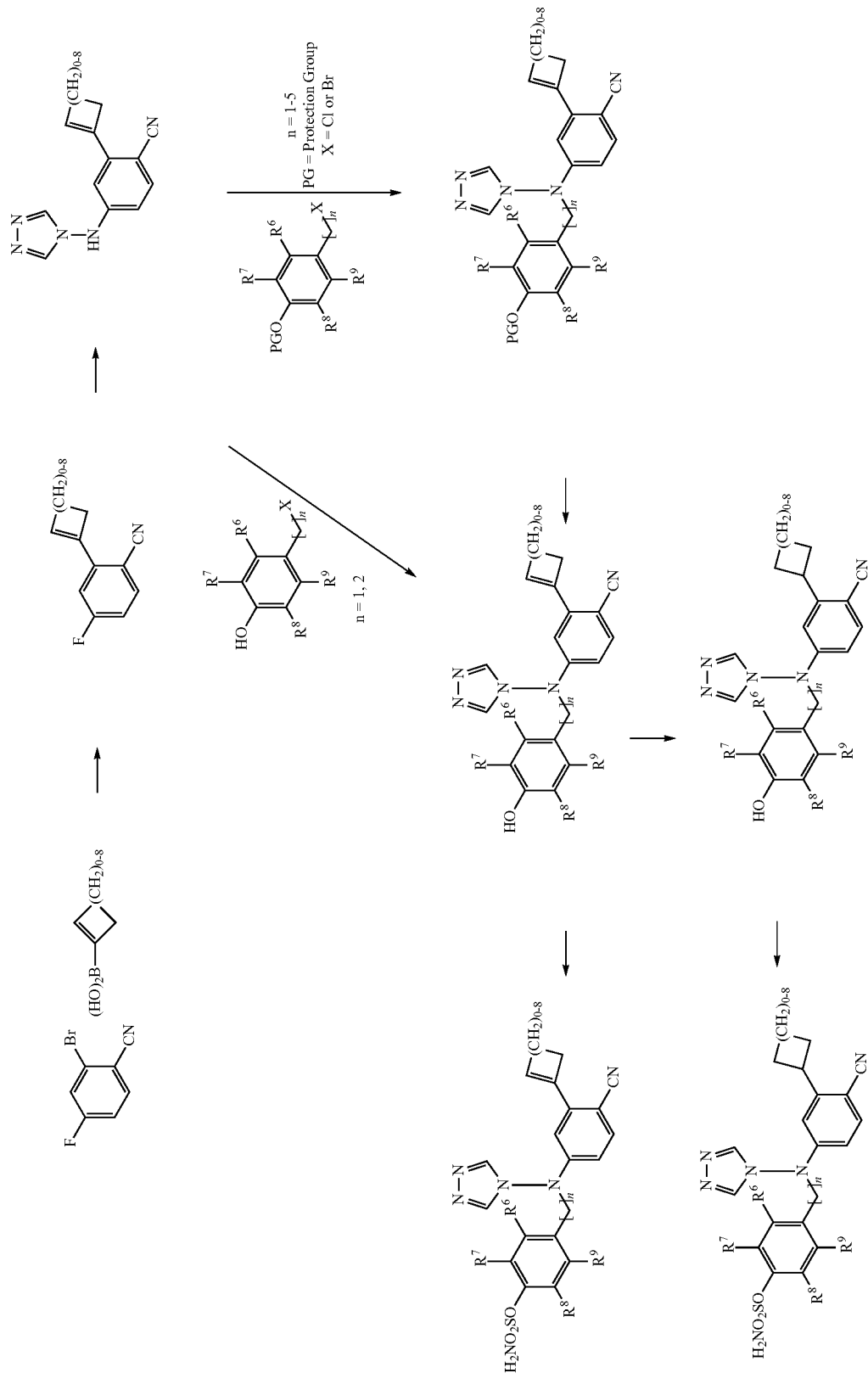
Scheme 3. General synthetic route for preparing derivatives containing an aliphatic ring.

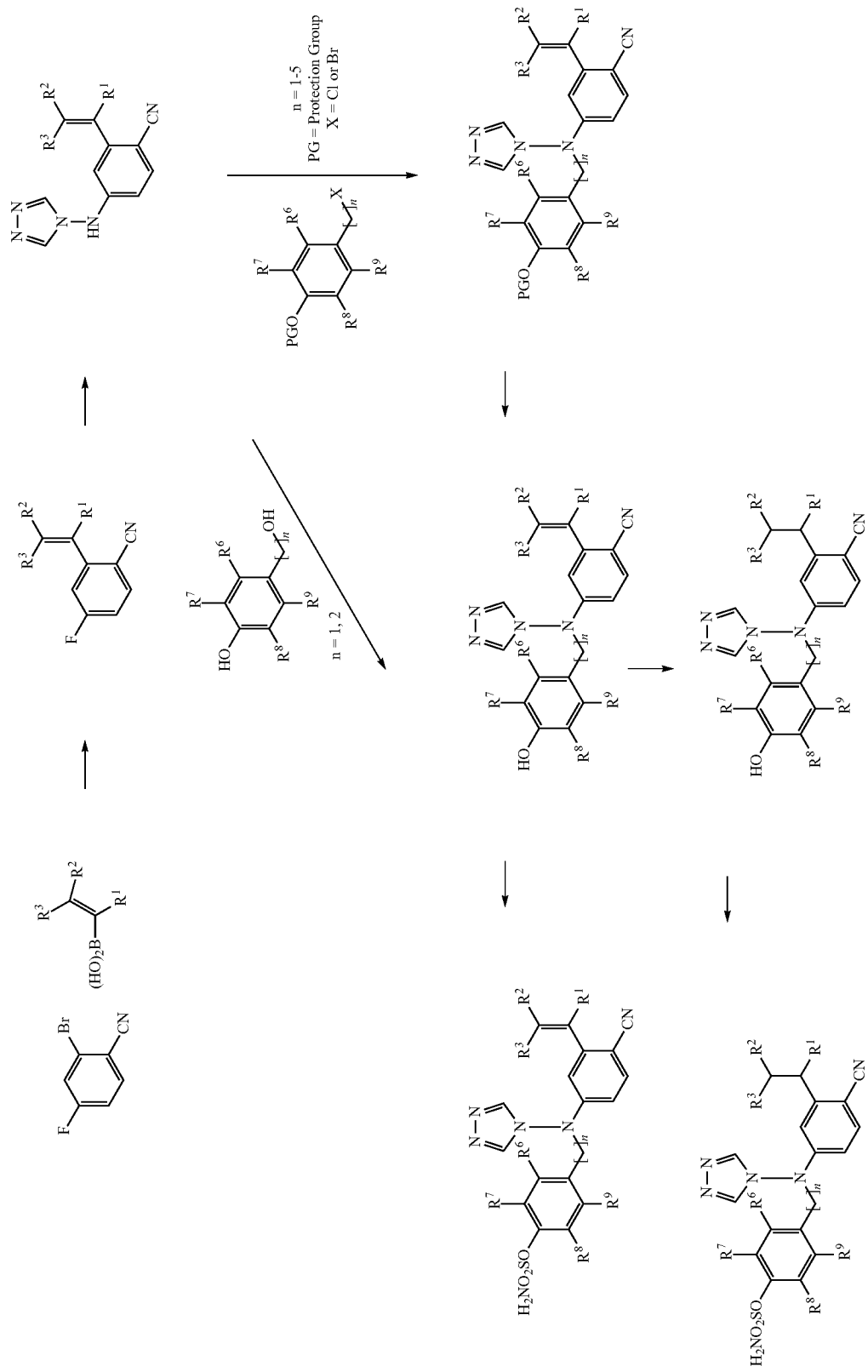

Scheme 5. General synthetic route for preparing derivatives containing a substituted biphenyl moiety where Z = a carbon atom, and D = a bond.
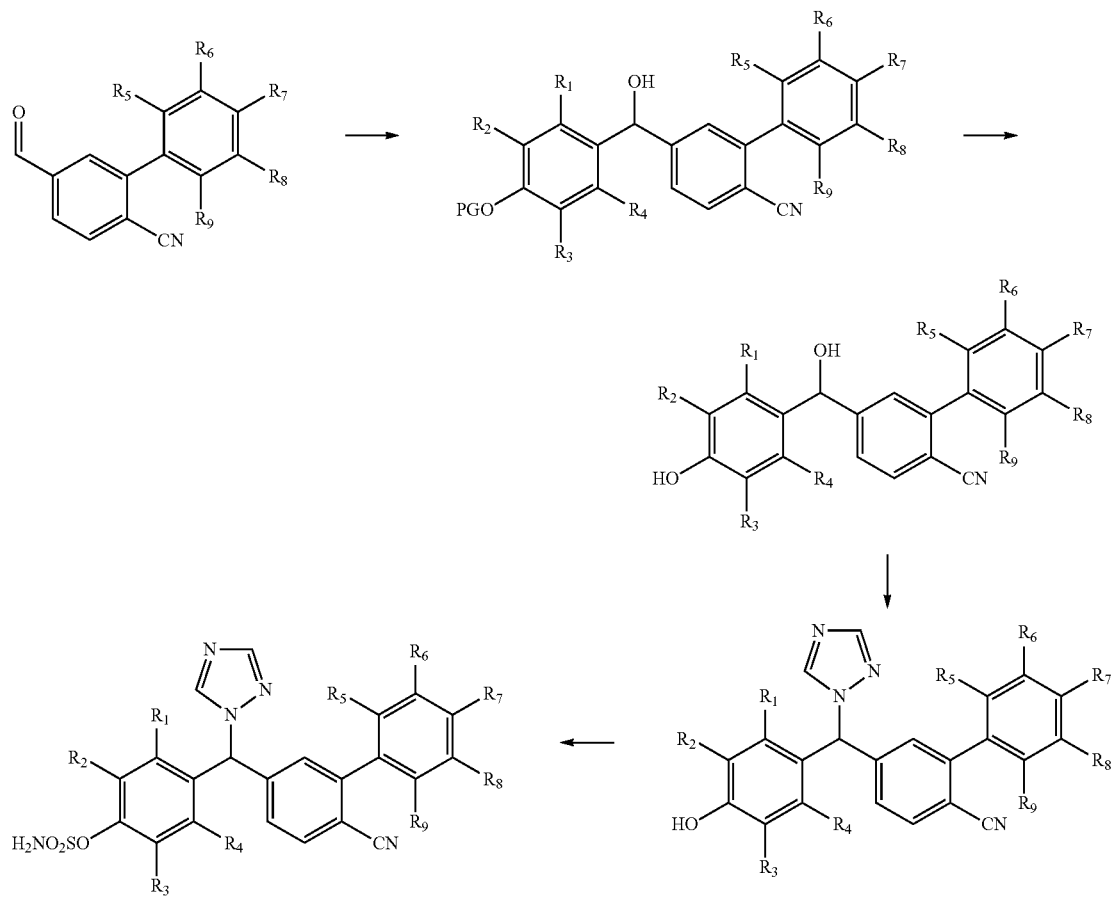
Scheme 6 General synthetic route for preparing derivatives containing a substituted biphenyl moiety where Z = a carbon atom, and D = (CH$_2$)$_n$
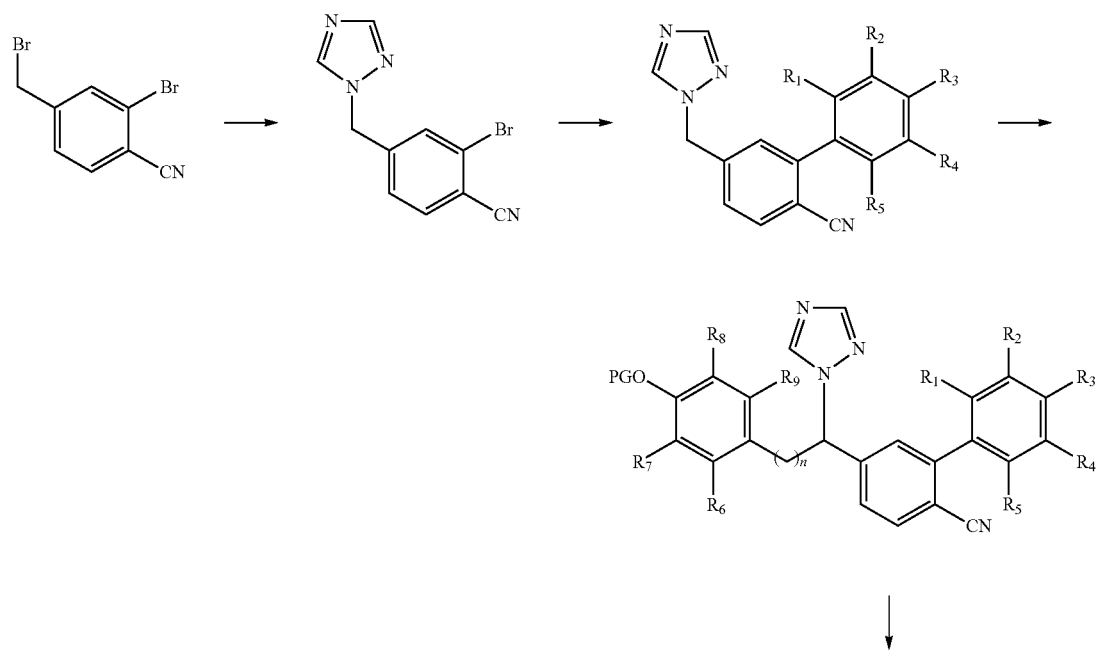

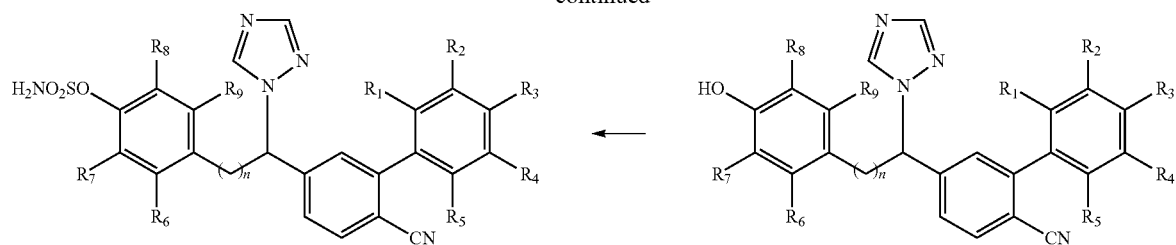
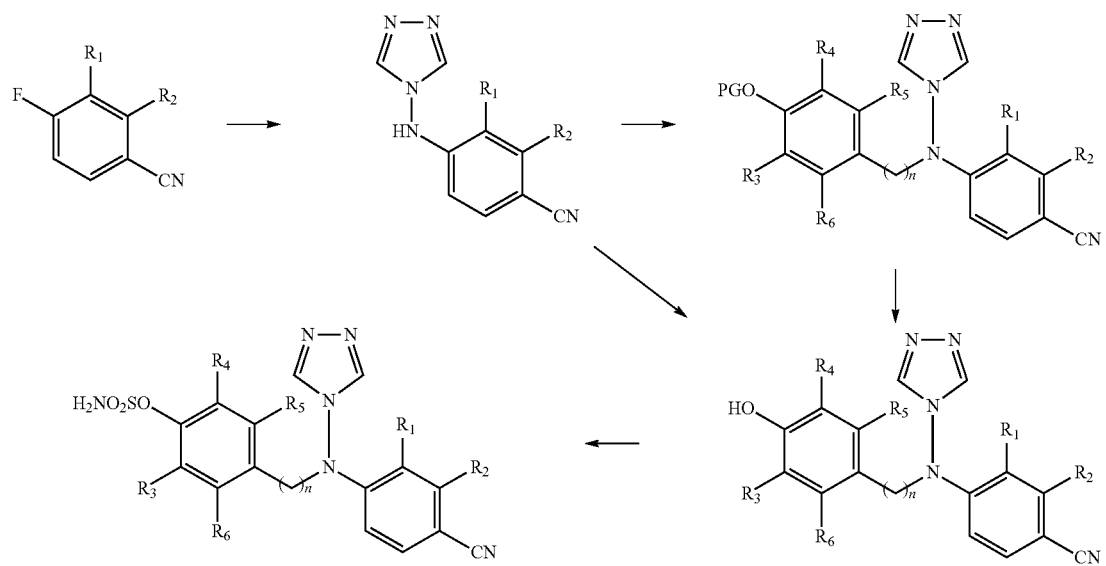
Scheme 7. General synthetic route for preparing derivatives where $R_1$ and $R_2$ together with the adjoining phenyl ring forms a fused bicyclic ring
eg R1, R2 = —CH=CH—CH=CH—
Scheme 8 General synthetic route for preparing derivatives where $R_1$ is a monocyclic or fused bicyclic heterocycle or lactam
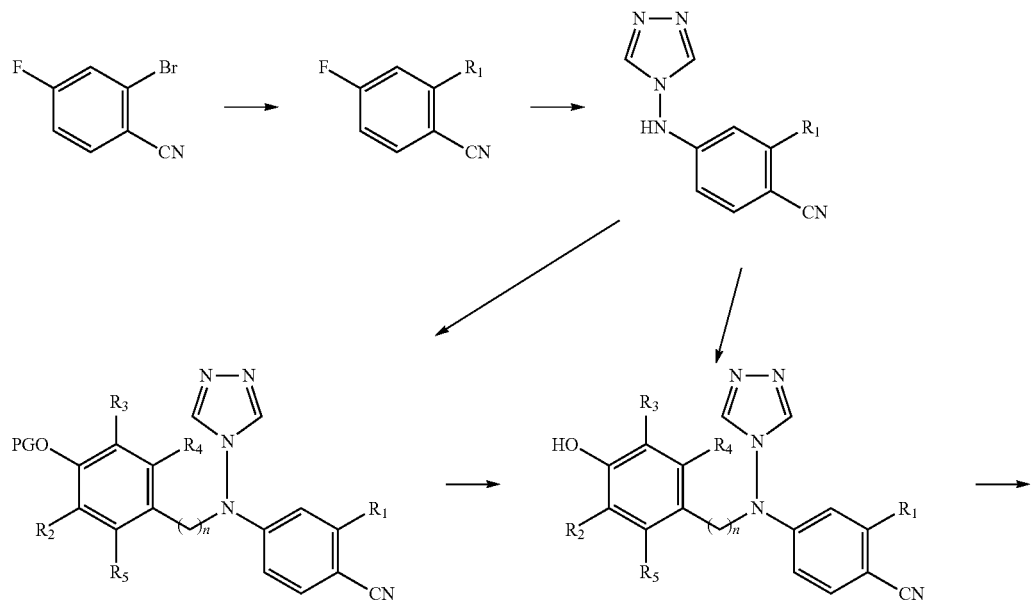

-continued
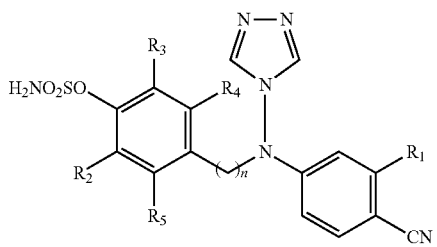
n = 1-5
Scheme 9. General synthetic route for preparing derivatives containing a piperidine, morpholine, piperazine and cyclic amine
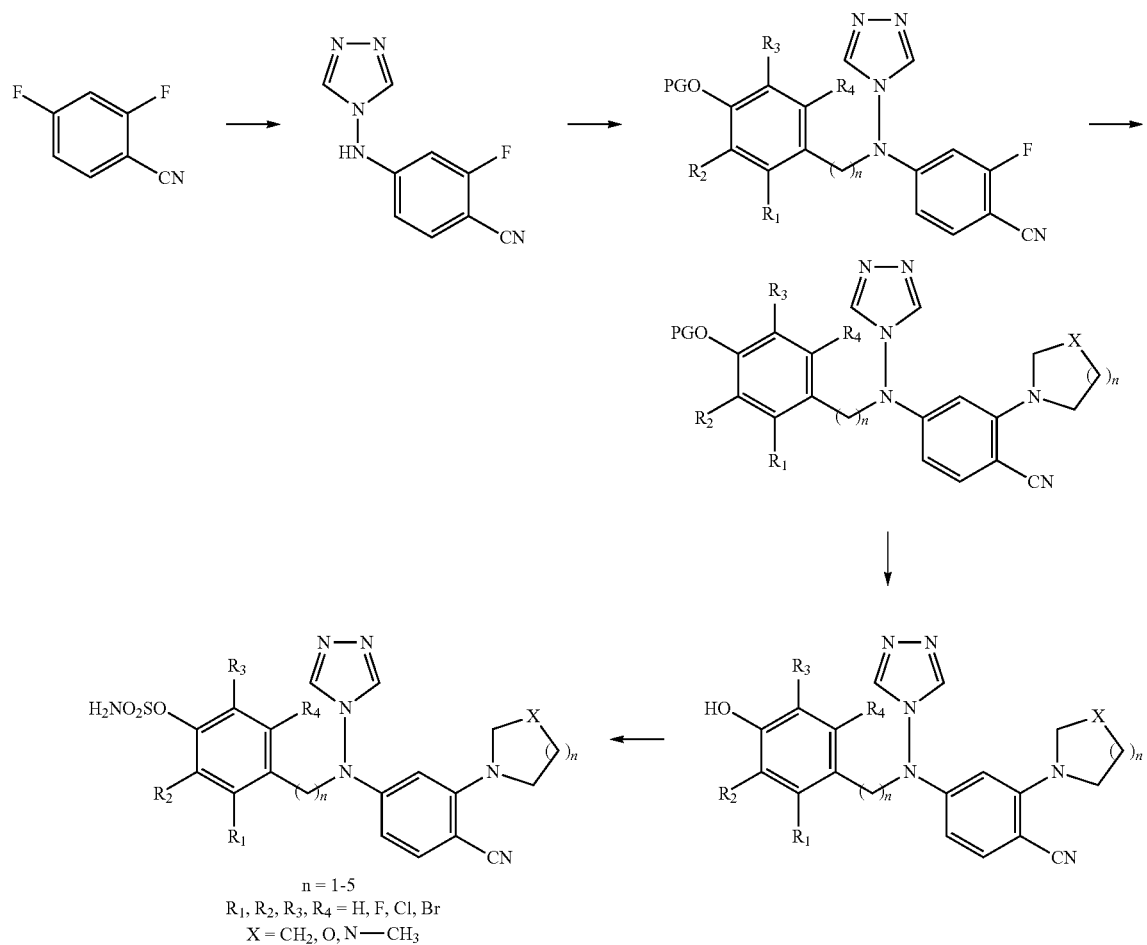
n = 1-5
R₁, R₂, R₃, R₄ = H, F, Cl, Br
X = CH₂, O, N—CH₃
Scheme 10. General synthetic route for preparing 1H-pyrroledione-, pyrrolidinedione- and piperidinedione-containing derivatives
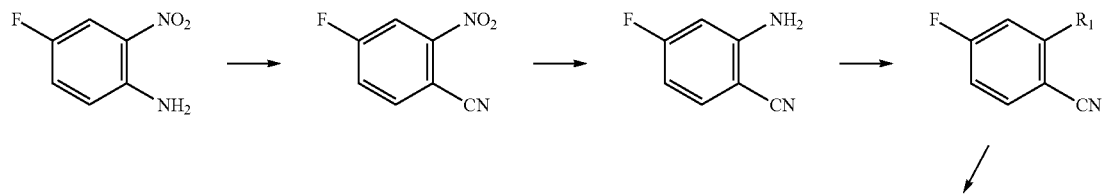

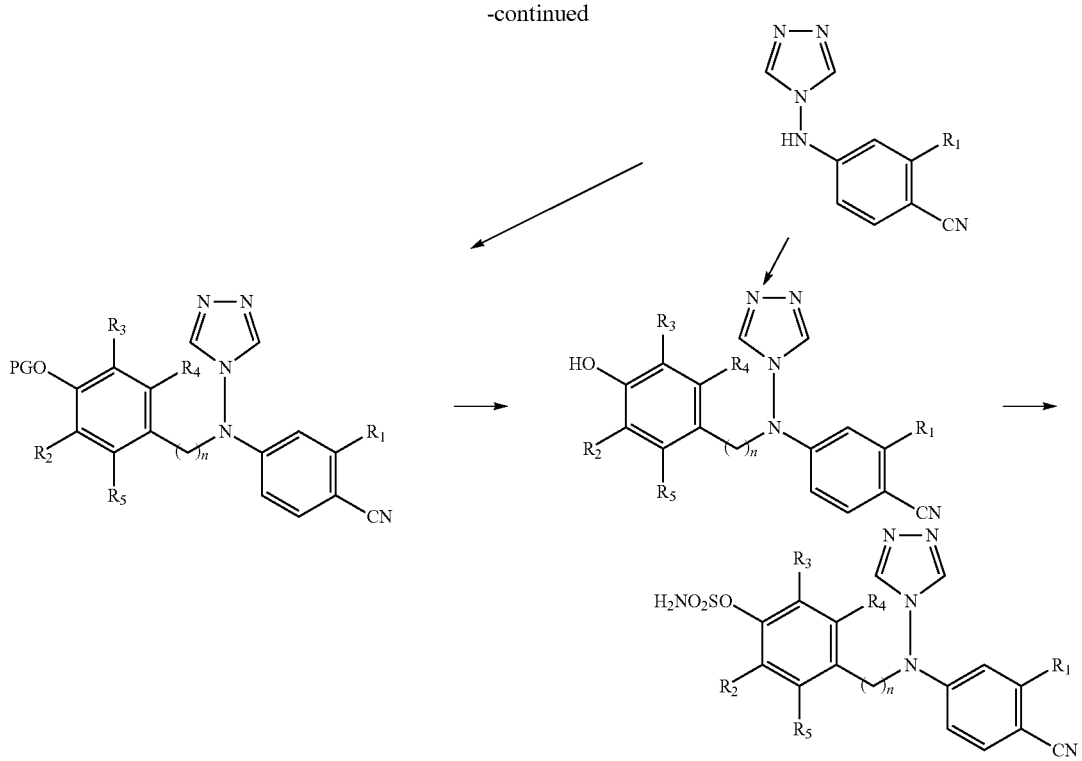

EXAMPLES

The present invention will now be described in further detail by way of example only with reference to the accompanying figure in which:—

FIG. 1 is a scheme
FIG. 2 is a scheme

The present invention will now be described only by way of example. However, it is to be understood that the examples also present preferred compounds of the present invention, as well as preferred routes for making same and useful intermediates in the preparation of same Synthetic Routes Compounds in accordance with the present invention were synthesised in accordance with the synthetic routes and schemes 4-(4H-1,2,4-Triazol-4-ylamino)-2-bromobenzonitrile (CAB05094)

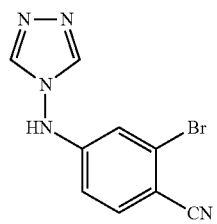 [SMILES: N#Cc1ccc(Nn2cnnc2)cc1Br]

To a solution of 4H-1,2,4-triazol-4-amine (4.204 g, 50.0 mmol) in DMSO (50 mL) was added KOtBu (5.51 g, 50.0 mmol). The mixture was stirred for 0.5 hours at room temperature before 4-fluoro-2-bromobenzonitrile (5.00 g, 25.0 mmol) was added and stirring was continued for 1 hour. The mixture was poured into crushed ice and neutralized with 2M KHSO$_4$ solution. The precipitate was filtered off and recrystallised from MeOH to give CAB05094 (4.82 g, 73%) as a light yellow crystalline solid. Mp. 234-236° C.; $^1$H NMR (400 MHz, DMSO-d$_6$) δ 6.66 (dd, J=8.6, 2.4 Hz, 1H), 6.79 (d, J=2.4 Hz, 1H), 7.78 (d, J=8.6 Hz, 1H), 8.86 (s, 2H), 10.45 (s, 1H); $^{13}$C NMR (100.6 MHz, DMSO-d$_6$) δ 105.0, 111.5, 115.4, 117.8, 126.0, 136.2, 143.9, 151.8; LRMS (APCI−): m/z 261.8 (100%, [C$_9$H$_5$$^{79}$BrN$_5$]$^−$), 263.8 (90%, [C$_9$H$_5$$^{81}$BrN$_5$]$^−$); HRMS (ES+) calcd for C$_9$H$_7$$^{79}$BrN$_5$ [M+H]$^+$: 263.9879. found 263.9870;

4-((4-(Benzyloxy)benzyl)(4H-1,2,4-triazol-4-yl)amino)-2-bromobenzonitrile (CAB05114)

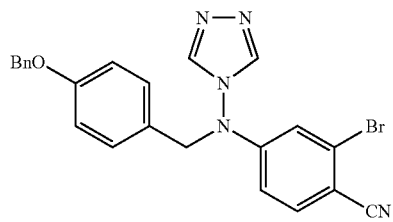 [SMILES: N#Cc1ccc(N(Cc2ccc(OCc3ccccc3)cc2)n2cnnc2)cc1Br]

To a solution of CAB05094 (1.32 g, 5.0 mmol) in DMF (20 mL) was added NaH (0 200 g, 3.0 mmol, 60% in mineral oil) at room temperature. The mixture was stirred for 0.5 hour before benzyloxybenzyl chloride (1.16 g, 5.0 mmol) was added and stirring was continued for 18 hours. The reaction mixture was diluted with EtOAc (50 mL), washed with water (3×30 mL) and brine (30 mL), dried (Na$_2$SO$_4$) and concentrated under reduced pressure. The residue was recrystallised from 2-propanol to afford CAB05114 (1.772 g, 77%) as colorless needles, Mp, 210-212° C.; $^1$H NMR (400 MHz, DMSO-$d_6$) δ 4.99 (s, 2H), 5.06 (s, 2H), 6.65 (dd, J=8.6, 2.4 Hz, 1H), 6.94 (AA'BB', 2H), 7.15 (d, J=2.4 Hz, 1H), 7.19 (AA'BB', 2H), 7.30-7.46 (m, 5H), 7.81 (d, J=8.6 Hz, 1H), 8.73 (s, 2H); $^{13}$C NMR (100.6 MHz, DMSO-$d_6$) δ 56.4, 69.2, 105.5, 112.8, 114.8, 116.7, 117.6, 126.0, 126.1, 127.8, 127.9, 128.4, 130.2, 135.9, 136.9, 143.3, 152.3, 158.2; LRMS (ES+): m/z 460.1 (100%, [M+H]$^+$); HRMS (ES+) calcd for $C_{23}H_{18}BrN_6ONa$ [M+Na]$^+$: 482.0587. found 482.0588; Anal. Calcd for $C_{23}H_{18}BrN_5O$: C, 60.01; H, 3.94; N, 15.21. Found C, 60.1; H, 3.92; N, 15.3.

5-((4-(Benzyloxy)benzyl)(4H-1,2,4-triazol-4-ylamino)biphenyl-2-carbonitrile (CAB06018)

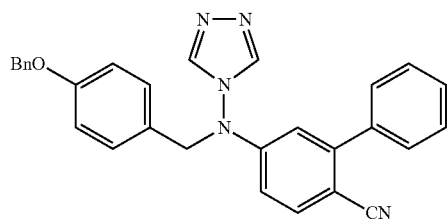

A mixture of CAB05114 (1.56 g, 3.39 mmol), phenyl boronic acid (0.61 g, 5.0 mmol), dimethoxyethane (25 mL) and 2M $Na_2CO_3$ (25 mL) was heated to reflux under $N_2$-atmosphere before and $Pd_2(dba)_2$ (0.05 g, 0.055 mmol) was added. The mixture was kept at reflux temperature for 4 hours (TLC-control) before it was cooled to room temperature and filtered (celite) to remove the solids. The mixture was then extracted with EtOAc (3×50 mL). The combined organic extracts were dried ($Na_2SO_4$) and concentrated under reduced pressure. The residue was purified by flash chromatography [$SiO_2$, $CHCl_3$/acetone (4:1)] followed by recrystallisation from EtOAc/hexane to afford CAB06018 (0.798 g, 51%) as fine colorless crystals. Mp. 171-173° C.; $^1$H NMR (400 MHz, DMSO-$d_6$) δ 5.05 (s, 2H), 5.06 (s, 2H), 6.72 (dd, J=9.0, 2.8 Hz, 1H), 6.80 (d, J=2.8 Hz, 1H), 6.96 (AA'BB', 2H), 7.2.3 (AA'BB', 2H), 7.30-7.53 (m, 10H), 7.86 (d, J=9.0 Hz, 1H), 8.78 (s, 2H); $^{13}$C NMR (100.6 MHz, DMSO-$d_6$) δ 56.5, 69.2, 101.9, 112.7, 114.0, 114.8, 118.8, 126.6, 127.8, 127.9, 128.5, 128.6, 128.8, 128.9, 130.1, 135.5, 136.9, 137.8, 143.4, 146.3, 151.5, 158.2; LRMS (ES+): m/z 458.4 (60%, [M+H]$^+$); 389.3 (100%); HRMS (ES+) calcd for $C_{19}H_{24}N_5O$ [M+H]$^+$: 458.1975. found 458.1971; Anal. Calcd for $C_{29}H_{23}N_5O$: C, 76.13; H, 5.07; N, 15.31. Found C, 76.2; H, 5.07; N, 15.4.

5-((4-Hydroxybenzyl)(4H-1,2,4-triazol-4-yl)amino)biphenyl-2-carbonitrile (CAB06021)

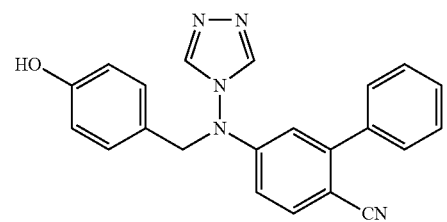 [SMILES: N#Cc1ccc(N(Cc2ccc(O)cc2)n2cnnc2)cc1-c1ccccc1]

To a solution of CAB06018 (0.458 g, 1.00 mmol) in THF and MeOH was added Pd—C (0.05 g, 5% Pd). The mixture was stirred under $H_2$-atmosphere for 18 hours before the catalyst was filtered off (celite) and the volatiles were removed under reduced pressure. The residue was recrystallized from EtOAc to afford CAB06021 (0.206 g, 56%) as a white solid. Mp.>180° C. (dec.); $^1$H NMR (400 MHz, DMSO-$d_6$) δ 4.98 (s, 2H0, 6.68 (AA'BB', 2H), 6.70-6.82 (m, 2H), 7.06 (AA'BB', 2H), 7.45-7.54 (m, 5H), 7.86 (d, J=8.6 Hz, 1H), 8.73 (s, 2H), 9.50 (s, 1H); $^{13}$C NMR (100.6 MHz, DMSO-$d_6$) δ 56.6, 101.8, 112.7, 114.0, 115.4, 118.8, 124.4, 128.6, 128.8, 128.9, 130.2, 135.5, 137.9, 143.5, 146.3, 151.6, 157.3; LRMS (ES+): m/z 368.2 (100%, [M+H]$^+$); HRMS (ES+) calcd for $C_{22}H_{17}N_5O$ [M+H]$^+$: 368.1506. found 368.1499.

4-(((6-Cyanobiphenyl-3-yl)(4H-1,2,4-triazol-4-yl)amino)methyl)phenyl sulfamate (CAB06025)

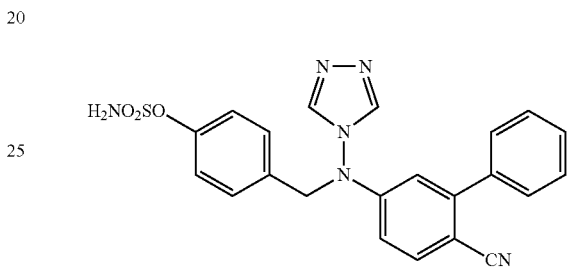

To a solution of sulfamoyl chloride (0.520 g, 4.5 mmol) in DMA (1 mL) was added a solution of CAB06021 (0.146 g, 0.397 mmol) in DMA (5 mL) at 0° C. The solution was stirred for 2 h at 0° C. and overnight at room temperature. EtOAc (60 mL) and water (30 mL) were added, the organic layer was separated, washed with water (3×20 mL) and brine (20 mL), dried ($Na_2SO_4$) and concentrated under reduced pressure. The residue was recrystallized from EtOAc to afford CAB06025 (0.132 g, 75%) as a white solid. Mp.>200° C. (dec.); $^1$H NMR (400 MHz, DMSO-$d_6$) δ 5.18 (s, 2H), 6.69 (dd, J=8.6, 2.7 Hz, 1H), 6.77 (d, J=2.7 Hz, 1H), 7.23 (AA'BB', 2H), 7.42 (AA'BB', 2H), 7.46-7.55 (m, 5H), 7.87 (d. J=8.6 Hz, 1H), 8.04 (s, 2H), 8.86 (s, 2H); $^{13}$C NMR (100.6 MHz, DMSO-$d_6$) δ 56.6, 102.0, 112.6, 113.9, 118.8, 122.3, 128.6, 128.8, 129.0, 129.8, 133.3, 135.6, 137.8, 143.4, 146.4, 149.9, 151.4; LRMS (ES-): m/z 445.7 (100%, [M-H]$^-$); HRMS (ES+) calcd for $C_{22}H_{19}N_6O_3S$ [M+H]$^+$: 447.1234. found 447.1223.

5-Fluoro-biphenyl-2-carbonitrile (CAB06020)

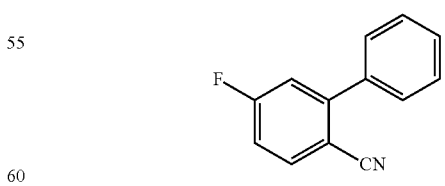

A mixture of 2-promo-4-fluorobenzinitrile (5.6 g, 28.0 mmol), phenylboronic acid (4.27 g, 35.0 mmol), dimethoxyethane (25 mL) and 2M $Na_2CO_3$ (40 mL) was heated to reflux before $Pd_2(dba)_3$ (0.10 g, 0.11 mmol) was added and heating was continued for 5 h. After cooling to room temperature $CHCl_3$ (50 mL) was added and the mixture was filtered (celite). The mixture was extracted with EtOAc (3×50 mL). The combined organic extracts were dried (Na₂SO₄) and concentrated under reduced pressure. The residue was purified by flash chromatography [SiO₂, CHCl₃/hexane (1:10)] followed by recrystallisation from hexane to give CAB06020 (4.29 g, 78%) as colorless needles. Mp, 79-80° C.; $^1$H NMR. (400 MHz, CDCl₃) δ 7.14 (dt, J=8.6, 2.7 Hz, 1H), 7.22 (dd, J=2.7 Hz, 1H), 7.46-7.57 (m, 5H), 7.77 (dd, J=8.6, 5.5 Hz, 1H); LRMS (ES+): m/z 197.9 (100%, [M+H]⁺); HRMS (ES+) calcd for $C_{13}H_9FN$ [M+H]⁺: 198.0714. found 198.0706; Anal. Calcd for $C_{13}H_8FN$: C, 79.17; H, 4.09; N, 7.10. Found C, 79.3; H, 4.08; N, 7.04.

5-(4H-1,2,4-Triazol-4-ylamino)biphenyl-2-carbonitrile (CAB06021)

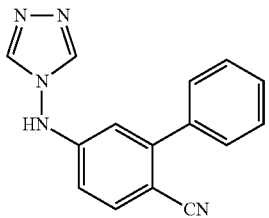 [SMILES: N#Cc1ccc(Nn2cnnc2)cc1-c1ccccc1]

To a solution of 4-amino-4H-1,2,4-triazole (3.29 g, 39.14 mmol) in DMSO (40 mL) was added KOtBu (4.39 g, 39.14 mmol). The mixture was stirred for 0.5 hours at room temperature before CAB06020 (3.86 g, 19.57 mmol) was added and stirring was continued for 1 hour. The mixture was poured into crushed ice and neutralised with 2M KHSO₄-solution. The white precipitate was filtered off, washed with water and recrystallised from 2-propanol to give CAB06022 (3.62 g, 71%) as light yellow crystals. Mp. 181-182° C.; $^1$H NMR (400 MHz, DMSO-d₆) δ 6.51 (d, J=15 Hz, 1H), 6.60 (dd, J=8.5, 2.5 Hz, 1H), 7.42-7.58 (m, 5H), 7.81 (d, J=8.5 Hz, 1H), 8.89 (s, 2H), 10.34 (s, 1H); $^{13}$C NMR (100.6 MHz, DMSO-d₆) δ 101.3, 111.4, 112.6, 119.0, 128.4, 128.8, 128.9, 135.7, 137.8, 144.1, 146.4, 150.9; LRMS (ES+): m/z 262.0 (100%, [M+H]⁺); HRMS (ES+) calcd for $C_{15}H_{11}N_5$ [M+H]⁺: 262.1087. found 262.1080.

4-Benzyloxy-3-fluoro-benzaldehyde (CAB06038)

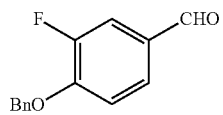

A mixture of 3-fluoro-4-hydroxybenzaldehyde (4.264 g, 30.0 mmol), benzyl bromide (5.986 g, 35.0 mmol, 4.16 mL) and K₂CO₃ (820 g, 59.0 mmol) in DMF (50 mL) was stirred for 48 hours at room temperature before EtOAc (100 mL) and water (50 mL) were added. The organic layer was separated, washed with water (2×50 mL), brine (30 mL) and dried (Na₂SO₄). Concentration in vacuo gave a white solid residue. Recrystallization from CH₂Cl₂/n-hexane afforded CAB06038 as colorless needles (5.59 g, 81%). Mp. 94-95° C.; $^1$H NMR (400 MHz, CDCl₃) δ 524 (s, 2H), 7.12 (dd, J=8.2, 8.2 Hz, 1H), 734-7.48 (m, 5H), 7.59-7.66 (m, 2H), 9.85 (d, J=2.0 Hz, 1H); LRMS (ES+): m/z 231.1 (100%, [M+H]⁺).

(4-(Benzyloxy)-3-fluorophenyl)methanol (CAB06039)

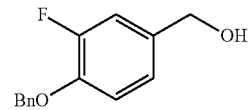

To a solution of CAB06038 (2.30 g, 10.0 mmol) in MeOH (10 mL) and THF (10 mL) was added NaBH₄ (0.20 g, 5.28 mmol) at 0° C. The mixture was stirred for 1 hour before EtOAc (50 mL) and water (20 mL) were added. The organic layer was separated, washed with 2M KHSO₄-solution (30 mL) and brine (0.30 mL), dried (MgSO₄) and concentrated under reduced pressure. The residue was purified by flash chromatography [SiO₂, EtOAc/petrol ether (1:4)] to afford CAB06038 (2.19 g, 94%) as a colorless crystalline solid. Mp. 56-57° C.; $^1$H NMR (400 MHz, CDCl₃) δ 1.71 (s, 1H—exchanges with D₂O), 4.61 (s, 2H), 5.15 (s, 2H), 6.97 (dd, J=8.6, 8.6 Hz, 1H), 7.02 (dd, J=8.6, 1.9 Hz, 1H), 7.13 (dd, J=11.7 Hz, 1.9 Hz, 1H), 7.30-7.46 (m, 5H); LRMS (FAB+): mix 232.1 (55%, [M]⁺), 215.1 (40%), 91.1 (100%).

1-(Benzyloxy)-4-(chloromethyl)-2-fluorobenzene (CAB06040)

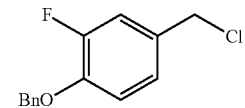 [SMILES: Fc1cc(CCl)ccc1OCc1ccccc1]

To a solution of CAB06039 (2.00 g, 8.61 mmol) in CH₂Cl₂ (20 mL) was added thionyl chloride (2.0 mL) at room temperature. The mixture was stirred at room temperature for 2 hours before the solvents and the excess thionyl chloride were removed under reduced pressure. The residue was purified by flash chromatography [SiO₂, CHCl₃] to afford a white solid, which was recrystallized from petrol ether to afford CAB06040 (2.01 g, 93%) as colorless fine needles. Mp, 67-69° C.; $^1$H NMR (400 MHz, CDCl₃) δ 4.52 (s, 2H), 5.15 (s, 2H), 6.96 (dd, J=8.2, 8.2 Hz, 1H), 7.04-7.06 (m, 1H), 7.15 (dd, J=11.7, 2.4 Hz, 1H), 7.31-7.45 (m, 5H); LRMS (FAB+): m/z 250.0 (16%, [M]⁺), 215.0 (10%), 91.0 (100%).

5-((4-(Benzyloxy)-3-fluorobenzyl)(4H-2,4-triazol-4-yl)amino)biphenyl-2-carbonitrile (CAB06041)

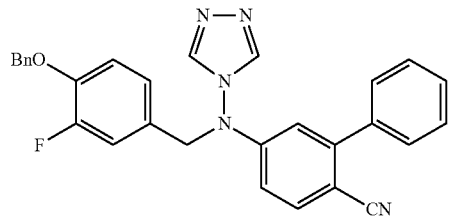 [SMILES: N#Cc1ccc(N(Cc2ccc(OCc3ccccc3)c(F)c2)n2cnnc2)cc1-c1ccccc1]

To a solution of CAB06022 (0.522 g, 1.99 mmol) in DMF (10 mL) was added NaH (0.080 g, 2.0 mmol) at room temperature. The mixture was stirred for 0.5 hours until the production of hydrogen ceased, then CAB06040 (0.501 g, 2.0 mmol) was added and stirring was continued for 18 hours. The reaction mixture was diluted with EtOAc (50 mL), washed with water (3×30 mL) and brine (30 mL), dried (Na$_2$SO$_4$) and concentrated under reduced pressure. The residue was purified by flash chromatography [SiO$_2$, CHCl$_3$/acetone (4:1)] to give CAB06041 as a white solid (0.879 g, 92%), which was recrystallised from EtOAc/cyclohexane to give colorless fine needles. Mp. 166-168° C.; $^1$H NMR (400 MHz, CDCl$_3$) δ 5.06 (s, 2H), 5.14 (s, 2H), 6.70 (dd, J=8.6, 2.7 Hz, 1H), 6.79 (d, J=2.7 Hz, 1H), 7.01-7.06 (m, 1H), 715-7.20 (m, 1H), 7.24 (dd, J=12.1, 2.3 Hz, 1H), 7.32-7.45 (m, 5H), 7.47-7.55 (m, 5H), 7.86 (d, J=8.6 Hz, 1H), 8.83 (s, 2H); LRMS (ES+): m/z 476.3 (100%, [M+H]$^+$); HRMS (ES+) calcd for C$_{29}$H$_{23}$FN$_5$O [M+H]$^+$: 476.1881. found 476.1896; Anal. Calcd for C$_{29}$H$_{22}$FN$_5$O: C, 73.25; H, 4.66; N, 14.73. Found C, 73.2; H, 4.63; N, 14.4.

5-((3-Fluoro-4-hydroxybenzyl)(4H-1,2,4-triazol-4-yl)amino)biphenyl-2-carbonitrile (CAB06043)

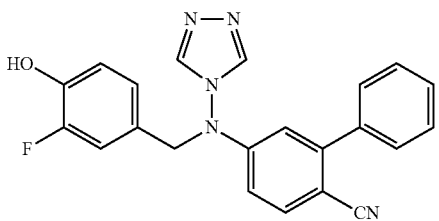 [SMILES: N#Cc1ccc(N(Cc2ccc(O)c(F)c2)n2cnnc2)cc1-c1ccccc1]

To a solution of CAB06041 (0.798 g, 1.678 mmol) in THF (20 mL) and methanol (20 mL) was added Pd—C (0.10 g, 5% Pd). The mixture was stirred under H$_2$-atmosphere for 48 hours before the catalyst was filtered off (celite) and the volatiles were removed under reduced pressure. The residue was recrystallised from EtOAc to give fine colorless crystals. Mp.>210° C. (dec.); $^1$H NMR (400 MHz, DMSO-d$_6$) δ 5.00 (s, 2H), 6.71 (dd, J=8.6, 27 Hz, 1H), 6.79 (d, J=2.7 Hz, 1H), δ 83-6.91 (m, 2H), 7.11 (dd, J=12.5, 2.0 Hz, 1H), 7.46-7.55 (m, 5H), 7.86 (d, J=8.6 Hz, 1H), 8.78 (s, 2H), 9.94 (s, 1H); LRMS (ES+): m/z 386.4 (100%, [M+H]$^+$); HRMS (ES+) calcd for C$_{22}$H$_{16}$FN$_5$ONa [M+Na]$^+$: 402.1231. found 402.1211.

4-(((6-Cyanobiphenyl-3-yl)(4H-1,2,4-triazol-4-yl)amino)methyl)-2-fluorophenyl sulfamate (CAB06044)

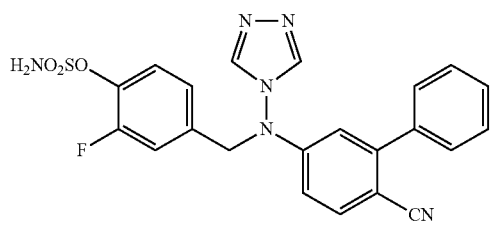

To a solution of sulfamoyl chloride (0.399 g, 3.45 mmol) in DMA (1 mL) was added a solution of CAB06043 (0.161 g, 0.418 mmol) in DMA (5 mL) at 0° C. The clear solution was stirred for 2 h at 0° C. and then for 4 h at room temperature, EtOAc (50 mL) and water (20 mL) were added, the organic layer was separated, washed with water (2×30 mL) and brine (30 mL), dried (Na$_2$SO$_4$) and concentrated under reduced pressure. The residue was purified by flash chromatography [SiO$_2$, CHCl$_3$/acetone (1:1)] to give CAB06044 (0.126 g, 65%) as a white solid. Mp. 198-200° C.; $^1$H NMR (400 MHz, DMSO-d$_6$) δ 5.20 (s, 2H), 6.65 (d, J=8.6 Hz, 1H), 6.75 (s, 1H), 7.22 (d, J=8.6 Hz, 1H), 7.30-7.58 (m, 7H), 7.86 (dd, J=8.6 Hz, 2.3 Hz, 1H), 8.29 (s, 2H), 8.92 (s, 2H; LRMS (ES+): m/z 465.2 (100%, [M+H]$^+$); HRMS (ES+) calcd for C$_{22}$H$_{18}$FN$_6$O$_3$S [M+H]$^+$: 465.1140. found 465.1118.

2-Chloro-4-hydroxymethyl-phenol (CAB06028)

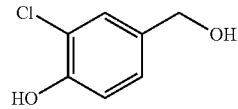

To a solution of 3-chloro-4-hydroxybenzaldehyde (4.697 g, 30.0 mmol) and to trimethoxyborate (0.5 mL) in THF (20 mL) and EtOH (20 mL) was added NaBH$_4$ (2.0 g, 52.87 mmol) in small portions over a period of 8 hours. The mixture was stirred overnight and EtOAc (100 mL) and water (50 mL) were added. The organic layer was separated and washed with 2M KHSO$_4$ (30 mL) and brine (30 mL), dried (MgSO$_4$) and concentrated under reduced pressure. The residue was purified by flash chromatography [SiO$_2$, CHCl$_3$/acetone (0.3:1)] followed by recrystallistion from EtOAc/hexane to give CAB06028 (3.82 g, 80%) as fine colorless needles: Mp. 126-127° C.; $^1$H NMR (400 MHz, DMSO-d$_6$) δ 4.36 (d, J=6.5 Hz, 2H), 5.11 (t, J=6.5 Hz, 1H), 6.90 (d, J=8.2 Hz, 1H), 7.06 (dd, J=82, 2.0 Hz, 1H), 7.25 (d, J=2.0 Hz, 1H), 9.99 (s, 1H); $^{13}$C NMR (100.6 MHz, DMSO-d$_6$) δ 62.1, 116.3, 119.2, 126.4, 128.1, 134.5, 151.7; LRMS (ES-): m/z 156.9 (100%, [M-H]).

5-9-Chloro-4-hydroxybenzyl)(4H-1,2,4-triazol-4-yl)amino)biphenyl-2-carbonitrile (CAB06047)

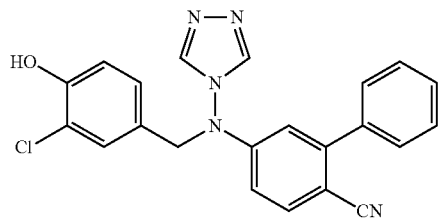

A solution of 2-chloro-4-(hydroxymethyl)phenol (CAB06028, 0.317 g, 2.0 mmol) in SOCl$_2$ (5 mL) was stirred at room temperature for 0.5 h. The excess SOCl$_2$ was removed under reduced pressure and the residue was dissolved in DMF (5 mL). Then CAB06022 (0.523 g, 2.0 mmol) and K$_2$CO$_3$ (1.38 g, 10 mmol) were added and the mixture was stirred intensively overnight. EtOAc (60 mL) and 2M KHSO$_4$ (30 mL) were added, the organic layer was separated, washed with water (10 mL) and brine (20 mL), dried (Na$_2$SO$_4$) and concentrated under reduced pressure. The residue was purified by flash chromatography ([SiO$_2$], acetone/chloroform 1:2) to afford CAB06047 (0.490 g, 61%) as a white solid: Mp, 226-228° C.; $^1$H NMR (400 MHz, DMSO-d$_6$) δ 5.00 (s, 2H), δ 70 (dd, J=8.6, 2.7 Hz. 1H), 6.80 (d, J=2.4 Hz, 1H), 6.87 (d, I=8.6 Hz, 1H), 7.02 (dd, J=8.6, 2.4 Hz, 1H), 7.46-7.56 (m, 5H), 7.29 (d, J=27 Hz, 1H), 7.85 (d, J=8.6 Hz, 1H), 8.78 (s, 2H), 10.28 (s, 1H); $^{13}$C NMR (100.6 MHz, DMSO-d$_6$) δ 56.1, 101.9, 112.7, 114.1, 116.6, 118.7, 119.6, 126.1, 128.5, 128.6, 128.8, 128.9, 130.4, 135.5, 137.8, 143.4, 146.3, 151.4, 152.9; LRMS (ES+): m/z 402.3 (100%, [M+H]$^+$); HRMS (ES+) calcd for C$_{22}$H$_{17}$ClN$_5$O [M+H]$^+$: 402.1116. found 402.1105.

2-Chloro-4-(((6-cyanobiphenyl-3-yl)(4H-1,2,4-triazol-4-yl)amino)methyl)phenyl sulfamate (CAB06049)

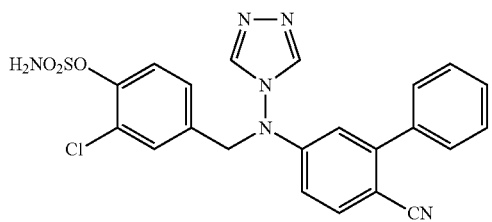

To a solution of sulfamoyl chloride (0.399 g, 3.45 mmol) in DMA (1 mL) was added a solution of CAB06047 (0.20 g, 0.498 mmol) in DMA (5 mL) at 0° C. The clear solution was stirred for 2 hours at 0° C. and then for 4 hours at room temperature. EtOAc (50 mL) and water (20 mL) were added, the organic layer was separated, washed with water (2×30 mL) and brine (30 mL), dried (Na$_2$SO$_4$) and concentrated under reduced pressure. The residue was purified by flash chromatography [SiO$_2$, CHCl$_3$/acetone (2:1)] to afford CAB06045 (0.158 g, 66%) as a white solid. Mp. 201-204° C.; $^1$H NMR (400 MHz, DMSO-d$_6$) δ 116 (s, 2H), 6.66 (dd, J=8.6, 2.4 Hz, 1H), 6.77 (d, J=2.4 Hz, 1H), 7.38 (dd, J=8.6, 2.3 Hz, 1H), 7.44 (d, J=8.6 Hz, 1H), 7.46-7.53 (m, 5H), 7.59 (d, J=2.3 Hz, 1H), 7.83 (d, J=8.6 Hz, 1H), 8.29 (s, 2H), 8.89 (s, 2H); $^{13}$C NMR (100.6 MHz, DMSO-d$_6$) δ 56.2, 102.2, 112.6, 114.0, 118.7, 123.7, 126.5, 128.1, 128.6, 128.8, 129.0, 130.3, 134.9, 135.6, 137.7, 143.4, 145.8, 146.3, 151.2; LRMS (ES+): m/z 481.2 (100%, [M+H]$^+$); HRMS (ES+) calcd for C$_{22}$H$_{18}$ClN$_6$O$_3$S [M+H]$^+$: 481.0844. found 481.0830.

5-((3-Bromo-4-hydroxybenzyl)(4H-1,2,4-triazol-4-yl)amino)biphenyl-2-carbonitrile (CAB06026)

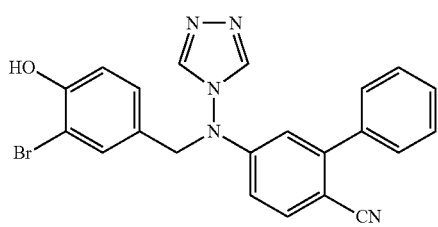 [SMILES: N#Cc1ccc(N(Cc2ccc(O)c(Br)c2)n2cnnc2)cc1-c1ccccc1]

A solution of 2-bromo-4-(hydroxymethyl)phenol (0.305 g, 1.5 mmol) in SOCl$_2$ (5 mL) was stirred at room temperature for 0.5 h. The excess SOCl$_2$ was removed under reduced pressure and the residue was dissolved in DMF (5 mL). Then CAB06022 (0:392 g, 1.5 mmol) and K$_2$CO$_3$ (1.38 g, 10 mmol) were added and the mixture was stirred intensively overnight. EtOAc (60 mL) and 2M KHSO$_4$ (30 mL) were added, the organic layer was separated, washed with water (10 mL) and brine (20 mL), dried (Na$_2$SO$_4$) and concentrated under reduced pressure. The residue was purified by flash chromatography [SiO$_2$, acetone/chloroform (1:2)] to afford CAB06026 (0.288 g, 43%) as a white solid: Mp. 218-220° C.; $^1$H NMR (400 MHz, DMSO-d$_6$) δ 5.00 (s, 2H), 6.70 (dd, J=8.6, 2.4 Hz, 1H), 6.82 (d, J=2.4 Hz, 1H), 6.86 (d, J=8.2 Hz, 1H), 7.07 (dd, J=8.2, 2.0 Hz, 1H), 7.44 (d, J=2.0 Hz, 1H), 7.48-7.58 (m, 5H), 7.86 (d, J=8.2 Hz, 1H), 8.79 (s, 2H), 10.38 (s, 1H); $^{13}$C NMR. (100.6 MHz, DMSO-d$_6$) δ 56.0, 101.9, 109.2, 112.7, 114.2, 116.3, 118.8, 126.5, 128.6, 128.8, 129.0, 129.3, 133.4, 135.6, 137.8, 143.5, 146.3, 151.4, 154.0; LRMS (ES+): m/z 446.2 (100%, [M+H]$^+$); HRMS (ES+) calcd for C$_{22}$H$_{17}$BrN$_5$O [M+H]$^+$: 446.0624. found 446.0617.

2-Bromo-4-(((6-cyanobiphenyl-3-yl)(4H-1,2,4-triazol-4-yl)amino)methyl)phenyl sulfamate (CAB06045)

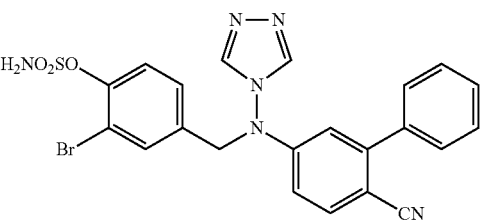

To a solution of sulfamoyl chloride (0.399 g, 3.45 mmol) in DMA (1 mL) was added a solution of CAB06026 (0.103 g, 0.231 mmol) in DMA (5 mL) at 0° C. The clear solution was stirred for 2 h at 0° C. and then for 4 h at room temperature. EtOAc (50 mL) and water (20 mL) were added, the organic layer was separated, washed with water (2×30 mL) and brine (30 mL), dried (Na$_2$SO$_4$) and concentrated under reduced pressure. The residue was purified by flash chromatography [SiO$_2$, CHCl$_3$/acetone (1:1)] to afford CAB06045 (0.073 g, 60%) as a white solid. Mp.>200° C. (dec.); $^1$H NMR (400 MHz, DMSO-d$_6$) δ 5.18 (s, 2H), 6.67 (dd, J=8.6, 2.4 Hz, 1H), 6.79 (d, J=2.4 Hz, 1H), 7.40-7.56 (m, 7H), 734 (d, J=1.6 Hz, 1H), 7.87 (d, J=8.6 Hz, 1H), 8.31 (s, 2H), 8.91 (s, 2H); $^{13}$C NMR (100.6 MHz, DMSO-d$_6$) δ 56.1, 102.1, 112.6, 114.0, 115.8, 118.7, 123.2, 128.5, 128.8, 129.0, 133.4, 135.0, 135.6, 137.7, 143.4, 146.3, 147.1, 151.2; LRMS (ES+): m/z. 527.2 (100%, [C$_{22}$H$_{18}$$^{81}$BrN$_6$O$_3$S]$^+$), 525.2 (90%, [C$_{22}$H$_{18}$$^{79}$BrN$_6$O$_3$S]$^+$); HRMS (ES+) calcd for C$_{22}$H$_{18}$$^{79}$BrN$_6$O$_3$S [M+H]$^+$: 525.0339. found 525.0320.

5-Fluoro-4'-methoxybiphenyl-2-carbonitrile (CAB06042)

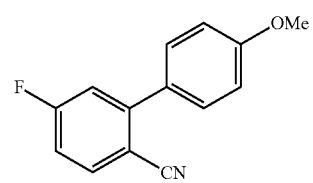 [SMILES: COc1ccc(-c2cc(F)ccc2C#N)cc1]

A mixture of 2-bromo-4-fluorobenzinitrile (5.0 g, 25.0 mmol), 4-methoxyphenylboronic acid (4.56 g, 30 mmol), dimethoxyethane (25 mL) and 2M Na$_2$CO$_3$ (40 mL) was heated to reflux before Pd$_2$(dba)$_3$ (0.10 g) was added and heating was continued for 5 hours. After cooling to room temperature CHCl$_3$ (50 mL) was added to dissolve the product, which crystallised from the organic layer. The mixture was filtered through celite, the organic layer was separated, dried (Na$_2$SO$_4$) and concentrated under reduced pressure. The residue was purified by flash chromatography [SiO$_2$, CHCl$_3$] followed by recrystallisation from EtOH to give CAB06042 as a white solid (4.03 g, 71%) Mp. 145-147° C.; $^1$H NMR (400 MHz, CDCl$_3$) δ 3.87 (s, 3H), 7.02 (AA'BB', 2H), 7.07-7.13 (m, 1H), 7.19 (dd, J=9.4, 2.7 Hz, 1H), 7.51 (AA'BB', 2H), 7.75 (dd, J=8.6, 5.5 Hz, 1H); LRMS (ES+): m/z 228.2 (100%, [M+H]$^+$); HRMS (ES+) calcd for C$_{14}$H$_{11}$FNO [M+H]$^+$: 228.0819. found 228.0816; Anal. Calcd for C$_{14}$H$_{10}$FNO: C, 74.00; H, 4.44; N, 6.16. Found C, 73.7; H, 4.40; N, 6.09.

5-(4H-1,2,4-Triazol-4-ylamino)-4'-methoxybiphenyl-2-carbonitrile (CAB06046)

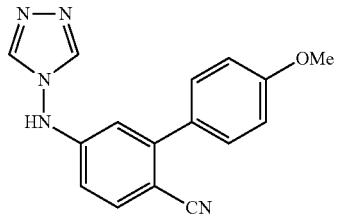 [SMILES: COc1ccc(-c2cc(Nn3cnnc3)ccc2C#N)cc1]

To a solution of 4H-1,2,4-triazol-4-amine (3.441 g, 40.928 mmol) in DMSO (40 mL) was added KOtBu (4.593 g, 40.928 mmol). The mixture was stirred for 0.5 hours at room temperature before CAB06042 (4.65 g, 20.468 mmol) was added and stirring was continued for 1 hour. The mixture was poured into crushed ice and neutralized with 2M KHSO$_4$ solution. The precipitate was filtered off and recrystallised from acetone/Et$_2$O to afford CAB06046 (5.07 g, 85%) as a light yellow crystalline solid. Mp. 176-177° C.; $^1$H NMR (400 MHz, DMSO-d$_6$) δ 3.81 (s, 3H), 6.47 (d, J=2.4 Hz, 1H), 6.54 (dd, J=8.6, 2.4 Hz, 1H), 7.07 (AA'BB', 2H), 7.43 (AA'BB', 2H), 7.77 (J=8.6 Hz, 1H), 8.86 (s, 2H), 10.28 (s, 1H); $^{13}$C NMR. (100.6 MHz, DMSO-d$_6$) δ 55.3, 101.2, 111.0, 112.3, 114.2, 119.1, 129.7, 130.0, 135.6, 144.1, 146.1, 150.8, 159.8; LRMS (ES+): m/z 2923 (100%, [M+H]$^+$); HRMS (ES+) calcd for C$_{16}$H$_{14}$N$_6$O [M+H]$^+$: 292.1193. found 292.1180; Anal, Calcd for C$_{16}$H$_{13}$N$_5$O: C, 65.97; H, 4.50; N, 24.04. Found C, 65.9; H, 4.56; N, 23.8.

5-((4-(Benzyloxy)benzyl)(4H-1,2,4-triazol-4-yl)amino)-4'-methoxybiphenyl-2-carbonitrile (CAB06065)

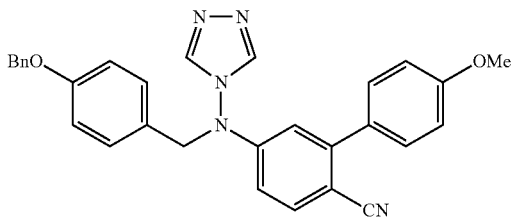 [SMILES: COc1ccc(-c2cc(N(Cc3ccc(OCc4ccccc4)cc3)n3cnnc3)ccc2C#N)cc1]

To a solution of CAB06046 (0.874 g, 3.0 mmol) in DMF (20 mL) was added NaH (0.120 g, 3.0 mmol, 60% in mineral oil) at room temperature. The mixture was stirred for 0.5 hours before benzyloxybenzyl chloride (0.698 g, 3.0 mmol) was added and stirring was continued for 18 hours. The reaction mixture was diluted with EtOAc (50 mL), washed with water (3×30 mL) and brine (30 mL), dried (Na$_2$SO$_4$) and concentrated under reduced pressure. The residue was recrystallised from 2-propanol to afford CAB06065 (1.112 g, 76%) as colorless needles. Mp. 219-221° C.; $^1$H NMR (400 MHz, DMSO-d$_6$) δ 3.81 (s, 3H), 5.04 (s, 2H), 5.06 (s, 2H), 6.69 (dd, J=8.6, 2.4 Hz, 1H), 6.74 (d, J=2.4 Hz, 1H), 6.95 (AA'BB', 2H), 7.07 (AA'BB', 2H), 7.23 (AA'BB', 2H), 7.30-7.44 (m, 5H), 7.47 (AA'BB', 2H), 7.82 (d, J=8.6 Hz, 1H), 8.77 (s, 2H); $^{13}$C NMR (100.6 MHz, DMSO-d$_6$) δ 55.3, 56.5, 69.2, 101.7, 112.3, 113.8, 114.2, 114.8, 119.0, 126.6, 127.8, 127.9, 128.4, 129.9, 130.0, 130.1, 135.5, 136.9, 143.4, 146.0, 151.5, 158.2, 159.9; LRMS (ES+): m/z 488.2 (100%, [M+H]$^+$); HRMS (ES+) calcd for C$_{30}$H$_{26}$N$_5$O$_2$ [M+H]$^+$: 476.1881. found 488.2063; Anal, Calcd for C$_{30}$H$_{25}$N$_5$O$_2$: C, 73.90; H, 5.17; N, 14.36. Found C, 73.7; H, 5.10; N, 14.3.

5-((4-Hydroxybenzyl)(4H-1,2,4-triazol-4-yl)amino)-4'-methoxybiphenyl-2-carbonitrile (CAB06073)

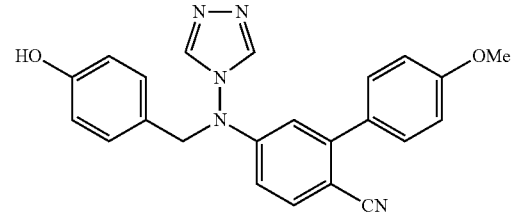 [SMILES: COc1ccc(-c2cc(N(Cc3ccc(O)cc3)n3cnnc3)ccc2C#N)cc1]

To a solution of CAB06065 (0.95 g, 1.95 mmol) in THF (20 mL) and methanol (20 mL) was added Pd—C (0.10 g, 5% Pd). The mixture was stirred under H$_2$-atmosphere for 48 h before the catalyst was filtered off (celite) and the volatiles were removed under reduced pressure. The residue was recrystallised from EtOH give CAB06073 (0.69 g, 89%) as colorless crystals. Mp. xxx-xxx ° C.; $^1$H NMR (400 MHz, DMSO-d$_6$) δ 3.81 (s, 3H), 4.96 (s, 2H), 6.65-6.71 (m, 3H), 6.74 (d, J=8.6 Hz, 1H), 7.04-7.10 (m, 4H), 7.46 (AA'BB', 2H), 7.81 (d, S=8.6 Hz, 1H), 8.71 (s, 2H), 9.49 (s, 1H); $^{13}$C NMR (100.6 MHz, DMSO-d$_6$) δ 55.3, 56.6, 101.6, 112.3, 113.8, 114.2, 115.4, 119.0, 124.5, 129.9, 130.0, 130.2, 135.5, 143.5, 146.0, 151.5, 157.2, 159.9; LRMS (ES+): m/z 398.2 (100%, [M+H]$^+$); HRMS (ES+) calcd for C$_{23}$H$_{19}$N$_5$O$_2$Na [M+Na]$^+$: 420.1431. found 420.1410; Anal. Calcd for C$_{23}$H$_{19}$N$_6$O$_2$: C, 69.51; H, 4.82; N, 17.62. Found C, 69.3; H, 4.80; N, 17.65.

4-(((6-Cyano-4'-methoxybiphenyl-3-yl)(4H-1,2,4-triazol-4-ylamino)methyl)phenyl sulfamate (CAB06077)

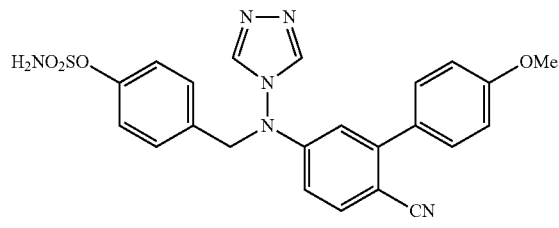

To a solution of sulfamoyl chloride (0.399 g, 3.45 mmol) in DMA (1 mL) was added a solution of CAB06073 (0.200 g, 0.503 mmol) in DMA (5 mL) at 0° C. The clear solution was stirred for 2 hours at 0° C. and then for 4 hours at room temperature. EtOAc (50 mL) and water (20 mL) were added, the organic layer was separated, washed with water (2×30 mL) and brine (30 mL), dried ($Na_2SO_4$) and concentrated under reduced pressure. The residue was recrystallised from EtOAc to afford CAB06077 (0.194 g, 81%) as a white solid. Mp. 184-186° C.; $^1$H NMR (400 MHz, DMSO-$d_6$) δ3.81 (s, 3H), 6.65 (dd, J=8.6, 2.3 Hz, 1H), 6.71 (d, J=2.3 Hz, 1H), 7.07 (AA'BB', 2H), 7.24 (AA'BB', 2H), 7.43 (AA'BB', 2H), 7.45 (AA'BB', 2H), 7.83 (d, J=8.6 Hz, 1H), 8.03 (s, 2H), 8.85 (s, 2H); $^{13}$C NMR (100.6 MHz, DMSO-$d_6$) δ 55.3, 56.6, 101.8, 112.2, 113.7, 114.2, 118.9, 122.2, 129.7, 129.9, 130.0, 133.3, 135.5, 143.4, 146.0, 149.8, 151.3, 159.9; LRMS (ES+): m/z 477.3 (100%, [M+H]$^+$); HRMS (ES+) calcd for $C_{23}H_{21}N_6O_4S$ [M+H]$^+$: 477.1340. found 477.1328.

5,4'-Difluoro-biphenyl-2-carbonitrile (CAB06058)

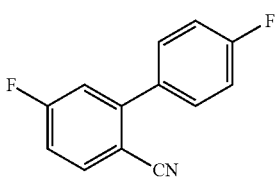 [SMILES: N#Cc1ccc(F)cc1-c1ccc(F)cc1]

A mixture of 2-bromo-4-fluorobenzinitrile (5.0 g, 25.0 mmol), 4-fluorophenylboronic acid (3.85 g, 27.5 mmol), dimethoxyethane (30 mL) and 2M $Na_2CO_3$ (40 mL) was heated to reflux before $Pd_2(dba)_3$ (0.10 g) was added and heating was continued for 5 hours. After cooling to room temperature $CHCl_3$ (50 mL) was added to and the mixture was filtered (celite). The organic layer was separated, dried ($Na_2SO_4$) and concentrated under reduced pressure. The residue was purified by flash chromatography [$SiO_2$, $CHCl_3$] followed by recrystallisation from $CHCl_3$/n-hexane to afford CAB06058 (4.03 g, 71%) as colorless needles. Mp. 111-113° C.; $^1$H NMR (400 MHz, CDCl$_3$) δ 7.12-7.23 (m, 4H), 7.50-7.56 (m, 2H), 7.76 (dd, J=8.6, 5.4 Hz, 1H); LRMS (ES+): m/z 416.0 (100%, [M+H]$^+$); HRMS (ES+) calcd for $C_{13}H_8F_2N$ [M+H]$^+$: 216.0619. found 216.0613; Anal. Calcd for $C_{13}H_7F_2N$: C, 72.56; H, 3.28; N, 6.51. Found C, 72.4; H, 3.28; N, 6.55.

5-(4H-1,2,4-Triazol-4-ylamino)-4'-fluorobiphenyl-2-carbonitrile (CAB06062)

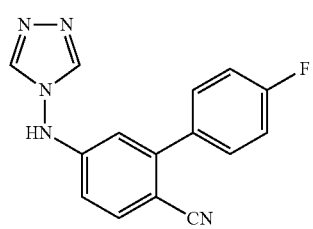 [SMILES: N#Cc1ccc(Nn2cnnc2)cc1-c1ccc(F)cc1]

To a solution of 4H-1,2,4-triazol-4-amine (1.711 g, 20.35 mmol) in DMSO (30 mL) was added KOtBu (2.28 g, 20.35 mmol). The mixture was stirred for 0.5 h at room temperature before CAB06058 (2.19 g, 10.17 mmol) was added and stirring was continued for 1 hour. The mixture was poured into crushed ice and neutralized with 2M $KHSO_4$ solution. The precipitate was filtered off, washed with water and recrystallised from EtOAc/n-hexane to afford CAB06062 (2.07 g, 73%) as a light yellow crystalline solid. Mp. 231-234° C.; $^1$H NMR (400 MHz, DMSO-$d_6$) δ 6.50 (d, I=2.4 Hz, 1H), 6.58 (dd, J=8.6, 2.4 Hz, 1H), 7.32-7.38 (m, 2H), 7.51-7.58 (m, 2H), 7.80 (d, 8.6 Hz, 1H), 8.86 (s, 2H), 10.32 (s, 1H); LRMS (ES+): m/z 280.1 (100%, [M+H]$^+$); HRMS (ES+) calcd for $C_{15}H_{11}FN_5$ [M+H]$^+$: 280.0993. found 280.0982; Anal. Calcd for $C_{15}H_{10}FN_5$: C, 64.51; H, 3.61; N, 25.08. Found C, 64.4; H, 3.57; N, 24.8.

5-((4-(Benzyloxy)benzyl)(4H-1,2,4-triazol-4-yl)amino)-4'-fluorobiphenyl-2-carbonitrile (CAB06064)

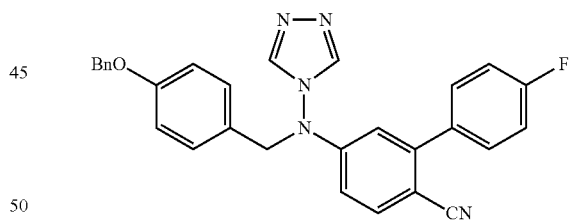

To a solution of CAB06062 (0.838 g, 3.0 mmol) in DMF (20 mL) was added NaH (0.120 g, 3.0 mmol, 60% in mineral oil) at room temperature. The mixture was stirred for 0.5 hours before benzyloxybenzyl chloride (0.698 g, 3.0 mmol) was added and stirring was continued for 18 hours. The reaction mixture was diluted with EtOAc (50 mL), washed with water (3×30 mL) and brine (30 mL), dried ($Na_2SO_4$) and concentrated under reduced pressure. The residue was recrystallised from 2-propanol to give CAB06064 (1.127 g, 79%) as colorless crystals. Mp. 211-213° C.; $^1$H NMR (400 MHz, DMSO-$d_6$) δ 5.05 (s, 2H), 5.06 (s, 2H), 6.70 (dd, J=8.6, 2.3 Hz, 1H), 6.83 (d, J=2.3 Hz, 1H), 6.88 (AA'BB', 2H), 7.21 (AA'BB', 2H), 730-7.44 (m, 7H), 7.55-7.60 (m, 2H), 7.85 (d, J=8.6 Hz, 1H), 8.75 (s, 2H); LRMS (ES+): m/z 476.3 (100%, [M+H]$^+$); HRMS (ES+) calcd for $C_{29}H_{23}FN_5O$ [M+H]$^+$:

476.1881. found 476.1860; Anal Calcd for $C_{29}H_{22}FN_5O$: C, 73.25; H, 4.66; N, 14:73. Found C, 73.3; H, 4.64; N, 14.8.

4'-Fluoro-5-((4-hydroxybenzyl)(4H-1,2,4-triazol-4-yl)amino)biphenyl-2-carbonitrile (CAB06069)

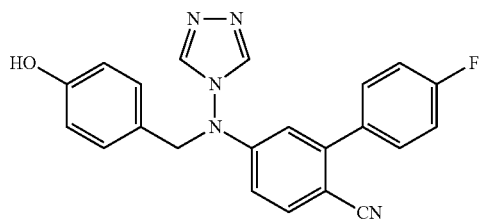 [SMILES: N#Cc1ccc(N(Cc2ccc(O)cc2)n2cnnc2)cc1-c1ccc(F)cc1]

To a solution of CAB306064 (0.93 g, 1.96 mmol) in THF (20 mL) and methanol (20 mL) was added Pd—C (0.10 g, 5% Pd). The mixture was stirred under $H_2$-atmosphere for 48 hours before the catalyst was filtered off (celite) and the volatiles were removed under reduced pressure. The residue was recrystallised from EtOH give CAB06069 (0.68 g, 90%) as light yellow crystals. Mp, 205-208*C; $^1$H NMR (400 MHz, DMSO-$d_6$) δ 4.97 (s, 2H), 6.67 (AA'BB', 2H), 6.70 (dd, J=8.6, 2.4 Hz, 1H), 6.82 (d, J=2.4 Hz, 1H), 7.06 (AA'BB', 2H), 7.34-7.40 (m, 2H), 7.55-7.60 (m, 2H), 7.84 (d, J=8.6 Hz, 1H), 8.71 (s, 2H), 9.49 (s, 1H); LRMS (ES+): m/z 386.1 (100%, [M+H]$^+$); HRMS (ES+) calcd for $C_{22}H_{17}FN_5O$ [M+H]$^+$: 386.1412. found 386.1397; Anal. Calcd for $C_{22}H_{16}FN_5O$: C, 68.56; H, 4.18; N, 18.17. Found C, 68.6; 4.18; N, 18.3,

4-(((6-Cyano-4'-fluorobiphenyl-3-yl)(4H-1,2,4-triazol-4-yl)amino)methyl)phenyl sulfamate (CAB06078)

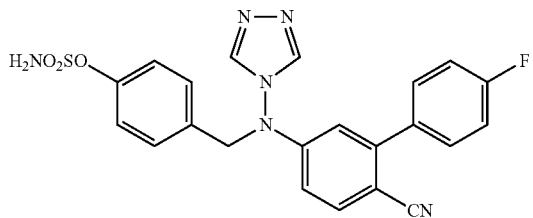

To a solution of sulfamoyl chloride (0.399 g, 3.45 mmol) in DMA (1 mL) was added a solution of CAB06069 (0.207 g, 0.503 mmol) in DMA (5 mL) at 0° C. The clear solution was stirred for 2 hours at 0° C. and then for 4 hours at room temperature, EtOAc (50 mL) and water (20 mL) were added, the organic layer was separated, washed with water (2×30 mL) and brine (30 mL), dried (Na$_2$SO$_4$) and concentrated under reduced pressure. The residue was recrystallised from EtOAc to afford CAB06078 (0.197 g, 79%) as a white solid. Mp. 197-199° C.; $^1$H NMR (400 MHz, DMSO-$d_6$) δ 5.17 (s, 2H), 6.67 (dd, J=8.6, 2.4 Hz, 1H), 6.80 (d, J=14 Hz, 1H), 7.2.3 (AA'BB', 2H), 731.7.44 (m, 4H), 7.52-7.60 (m, 2H), 7.86 (d, J=8.6 Hz, 1H), 8.03 (s, 2H), 8.84 (s, 2H); LRMS (ES+): m/z 465.4 (100%, [M+H]$^+$); HRMS (ES+) calcd for $C_{22}H_{18}FN_6O_3S$ [M+H]$^+$: 477.1140. found 465.1123.

5-((4-(Benzyloxy)benzyl)(4H-1,2,4-triazol-4-yl)amino)biphenyl-2,4'-dicarbonitrile (CAB06075)

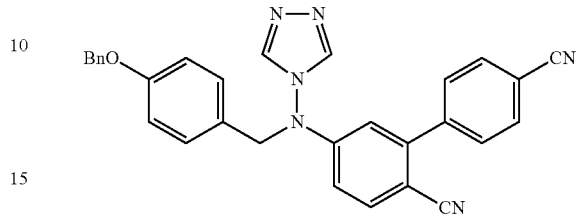

A mixture of 4-((4-(benzyloxy)benzyl)(4H-1,2,4-triazol-4-yl)amino)-2-bromobenzonitrile (CAB05114, 0.460 g, 1.0 mmol), 4-cyanophenylboronic acid (0.184 g, 1.25 mmol), dimethoxyethane (20 mL) and 2M Na$_2$CO$_3$ (20 mL) was heated to reflux before Pd$_2$(dba)$_3$ (0.05 g) was added and heating was continued for 5 hours. After cooling to room temperature EtOAc (50 mL) was added to and the mixture was filtered (celite). The organic layer was separated, dried (Na$_2$SO$_4$) and concentrated under reduced pressure. The residue was purified by flash chromatography [SiO$_2$, CHCl$_3$/acetone (2:1)] to afford CAB06075 (4.03 g, 71%) as a white solid. Mp. 234-237-113° C.; $^1$H NMR (400 MHz, DMSO-$d_6$) δ 5.02 (s, 4H), 6.72 (dd, J=8.6, 2.7 Hz, 1H), 6.91 (d, J=2.7 Hz, 1H), 6.95 (AA'BB', 2H), 7.21 (AA'BB', 2H), 7.30-7.45 (m, 5H), 7.75 (AA'BB', 2H), 7.90 (d, J=8.6 Hz, 1H), 8.02 (AA'BB', 2H), 8.75 (s, 2H); $^{13}$C NMR (100.6 MHz, DMSO-$d_6$) δ 56.5, 69.2, 101.7, 111.7, 113.4, 113.7, 114.1, 114.8, 118.3, 118.4, 126.4, 127.8, 127.9, 128.4, 129.7, 130.0, 130.1, 132.7, 135.6, 136.9, 142.3, 143.3, 144.5, 145.9, 151.5, 158.2; LRMS (ES+): m/z 4833 (100%, [M+H]$^+$); HRMS (ES+) calcd for $C_{30}H_{23}N_6O$ [M+H]$^+$: 483.1928. found 483.1918.

5-((4-Hydroxybenzyl)(4H-1,2,4-triazol-4-yl)amino)biphenyl-2,4'-dicarbonitrile (CAB06076)

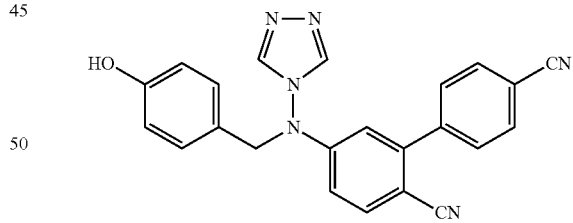

To a solution of CAB06075 (0.201 g, 0.417 mmol) in THF (20 mL) and methanol (20 mL) was added Pd—C (0.05 g, 5% Pd). The mixture was stirred under $H_2$-atmosphere for 48 hours before the catalyst was filtered off (celite) and the volatiles were removed wider reduced pressure. The residue was suspended in EtOAc and heated to reflux for 5 minutes. After cooling down to room temperature the precipitate was filtered of and dried under high vacuum to afford CAB06076 (0.146 g, 89%) as a white solid. Mp. 221-223° C.; $^1$H NMR (400 MHz, DMSO-$d_6$) δ 4.98 (s, 2H), 6.67 (AA'BB', 2H), 6.73 (dd, J=8.6, 2.4 Hz, 1H), 6.91 (d, J=2.4 Hz, 1H), 7.06 (AA'BB', 2H), 7.75 (AA'BB', 2H), 7.89 (d, 8.6 Hz, 1H), 8.01 (d, J=8.6 Hz, 1H), δ 70 (s, 2H), 9.51 (s, 1H); $^{13}$C NMR (100.6

MHz, DMSO-d$_6$) δ 56.5, 101.6, 111.3, 113.4, 114.1, 115.4, 118.4, 118.5, 124.3, 129.3, 130.2, 132.7, 135.6, 142.3, 143.4, 144.5, 151.6, 157.3; LRMS (ES+): m/z 393.1 (100%, [M+H]$^+$); HRMS (ES+) calcd for C$_{23}$H$_{17}$N$_6$O [M+H]$^+$: 393.1458. found 393.1450.

4-(((4',6-Dicyanobiphenyl-3-yl)(4H-1,2,4-triazol-4-yl)amino)methyl)phenyl sulfamate (CAB06088)

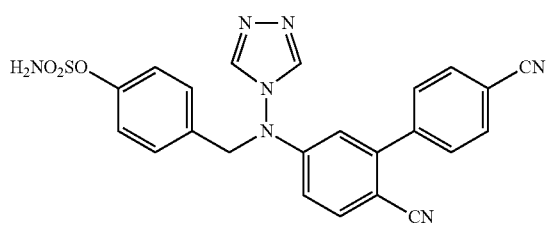

To a solution of sulfamoyl chloride (0.399 g, 3.45 mmol) in DMA (1 mL) was added a solution of CAB06076 (0.102 g, 0.26 mmol) in DMA (5 mL) at 0° C. The clear solution was stirred for 2 hours at 0° C. and then for 4 hours at room temperature. EtOAc (50 mL) and water (20 mL) were added, the organic layer was separated, washed with water (2×30 mL) and brine (0.30 mL), dried (Na$_2$SO$_4$) and concentrated under reduced pressure. The residue was purified by flash chromatography [SiO$_2$, CHCl$_3$/acetone (1:1)] to afford CAB06088 (0.065 g, 53%) as a white solid. Mp, >140° C. (dec.); $^1$H NMR (400 MHz, DMSO-d$_6$) δ 5.17 (s, 2H), 6.60 (dd, J=8.6, 24 Hz, 2H), 6.87 (d, J=2.4 Hz, 2H), 7.22 (AA'BB', 2H), 7.40 (AA'BB', 2H), 7.71 (AA'BB', 2H), 7.89 (d, J=8.6 Hz, 1H), 7.99 (AA'BB', 2H), 8.02 (s, 2H), 8.83 (s, 2H); $^{13}$C NMR (100.6 MHz, DMSO-d$_6$) δ 56.5, 101.9, 111.8, 113.3, 114.0, 118.3, 118.5, 122.3, 129.7, 129.8, 132.7, 133.1, 135.7, 142.2, 143.4, 144.6, 149.9, 151.4; LRMS (ES+): m/z 471.2 (100%, [M+H]$^{30}$); HRMS (ES+) calcd for C$_{23}$H$_{18}$N$_7$O$_3$S [M+H]$^+$: 472.1186. found 472.1180.

4'-(Benzyloxy)-5-fluorobiphenyl-2-carbonitrile (CAB06048)

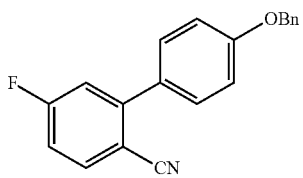 [SMILES: N#Cc1ccc(F)cc1-c1ccc(OCc2ccccc2)cc1]

A mixture of 2-bromo-4-fluorobenzinitrile (4.50 g, 22.5 mmol), 4-benzyloxyphenylboronic acid (5.19 g, 22.76 mmol), dimethoxyethane (25 mL) and 2M Na$_2$CO$_3$ (40 mL) was heated to reflux before Pd$_2$(dba)$_3$ (0.05 g, 0.055 mmol) was added and heating was continued for 5 hours. After cooling to room temperature CHCl$_3$ (ca. 100 mL) was added to dissolve the product, which crystallised from the organic layer. The mixture was filtered through celite, the organic layer was separated, dried (Na$_2$SO$_4$) and concentrated under reduced pressure. The residue was recrystallized from CHCl$_3$/hexane to give CAB06048 (5.32 g, 78%) as colorless needles. Mp. 94-96° C.; $^1$H NMR (400 MHz, DMSO-d$_6$) δ 5.12 (s, 2H), 7.06-712 (m, 3H), 7.18 (dd, J=9.4, 2.7 Hz, 1H), 7.33-7.53 (m, 7H), 7.74 (dd, J=8.6, 5.7 Hz, 1H); LRMS (ES+): m/z 326.4 (100%, [M+N]$^+$), 304.3 (60%, [M+H]$^+$); HRMS (ES+) calcd for C$_{20}$H$_{15}$FNO [M+H]$^+$: 304.1132. found 304.1125.

5-(4H-1,2,4-Triazol-4-ylamino)-4'-(benzyloxy)biphenyl-2-carbonitrile (CAB06050)

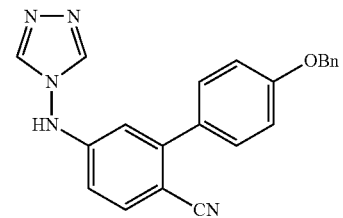 [SMILES: N#Cc1ccc(Nn2cnnc2)cc1-c1ccc(OCc2ccccc2)cc1]

To a solution of 4H-1,2,4-triazol-4-amine (2.439 g, 29.01 mmol) in DMSO (50 mL) was added KOtBu (3.36 g, 30.0 mmol). The mixture was stirred for 0.5 hours at room temperature before CAB06048 (440 g, 14.51 mmol) was added and stirring was continued for 1 hour. The mixture was poured into crushed ice and neutralized with 2M KHSO$_4$ solution. The precipitate was filtered off and recrystallised from EtOAc/n-hexane to give CAB06050 (5.07 g, 85%) as fine colorless needles. Mp. 180-182° C.; $^1$H NMR (400 MHz, DMSO-d$_6$) δ 5.17 (s, 2H), 6.47 (d, J=2.4 Hz, 1H), 6.54 (dd, J=8.6, 2.4 Hz, 1H), 7.15 (AA'BB', 2H), 7.32-7.50 (m, 7H), 7.78 (d, J=8.6 Hz, 1H), 8.86 (s, 2H), 10.28 (s, 1H); $^{13}$C NMR (100.6 MHz, DMSO-d$_6$) δ 69.4, 101.2, 111.0, 112.3, 115.0, 119.1, 127.8, 127.9, 128.5, 129.7, 130.2, 135.6, 136.8, 144.1, 146.0, 150.8, 158.9; LRMS (ES+): m/z 368.2 (100%, [M+H]$^+$); HRMS (ES+) calcd for C$_{22}$H$_{18}$N$_5$O [M+H]$^+$: 368.1506. found 368.1494

4'-(Benzyloxy)-5-((4-bromobenzyl)(4H-1,2,4-triazol-4-ylamino)biphenyl-2-carbonitrile (CAB06051)

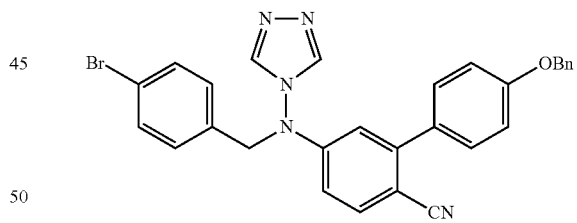

To a solution of CAB06050 (2.20 g, 5.99 mmol) in DMF (20 mL) was added NaH (0.240 g, 6.0 mmol) at room temperature. The mixture was stirred for 0.5 hours until the production of hydrogen ceased, then 4-bromobenzyl bromide (1.497 g, 5.99 mmol) was added and stirring was continued for 18 hours. The reaction mixture was diluted with EtOAc (60 mL), washed with water (3×30 mL) and brine (30 mL), dried (Na$_2$SO$_4$) and concentrated under reduced pressure. The residue was recrystallized from EtOH to afford CAB06051 (165 g, 82%) as fine light yellow needles, Mp. 186-188° C.; $^1$H NMR (400 MHz, CDCl$_3$) δ 5.12 (s, 2H), 5.18 (s, 2H), 6.64 (dd, T=8.6, 2.4 Hz, 1H), 6.75 (d, T=2.4 Hz, 1H), 7.14 (AA'BB', 2H), 7.28 (AA'BB', 2H), 7.30-7.50 (m, 5H), 7.53 (AA'BB', 2H), 7.82 (AA'BB', 2H), 8.79 (s, 2H); $^{13}$C NMR (100.6 MHz, DMSO-d$_6$) δ 56.5, 69.3, 101.9, 112.3, 113.8, 115.0, 118.9, 121.3, 127.7, 127.9, 128.5, 129.9, 130.1, 130.7, 131.6, 134.2, 135.5, 136.8, 149.4, 146.0, 151.3, 159.0; LRMS (ES+): m/z 536.2 (100%, [M+H]$^+$); HRMS (ES+) calcd for C$_{29}$H$_{23}$BrN$_5$O [M+H]$^+$: 536.1080. found 536.1064.

5-(Benzyl-[1,2,4]triazol-4-yl-amino)-4'-hydroxy-biphenyl-2-carbonitrile (CAB06052)

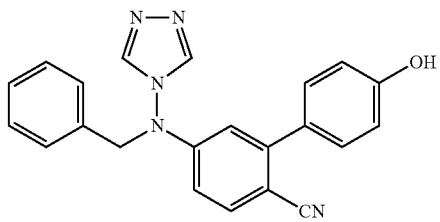 [SMILES: N#Cc1ccc(N(Cc2ccccc2)n2cnnc2)cc1-c1ccc(O)cc1]

To a solution of CAB06051 (0.536 g, 1.00 mmol) in THF (20 mL) and methanol (20 mL) was added Pd—C (0.050 g, 5% Pd). The mixture was stirred under H$_2$-atmosphere for 48 hows before the catalyst was filtered off (celite) and the volatiles were removed under reduced pressure. The residue was purified by flash chromatography [SiO$_2$, CHCl$_3$/acetone (3:1)] to afford CAB06052 (0.297 g, 81%) as a white solid. Mp. 229-230° C.; $^1$H NMR (400 MHz, DMSO-d$_6$) δ 5.12 (s, 2H), 6.65 (dd, J=8.6, 2.4 Hz, 1H), 6.70 (d, J=2.4 Hz, 1H), 6.88 (AA'BB', 2H), 5.28-7.36 (m, 7H), 7.80 (d, J=8.6 Hz, 1H), 8.81 (s, 2H), 9.82 (s, 1H); $^{13}$C NMR (100.6 MHz, DMSO-d$_6$) δ 57.2, 101.7, 112.0, 111.6, 115.5, 119.1, 128.0, 128.4, 128.5, 128.7, 129.8, 134.8, 135.8, 143.4, 146.4, 151.5, 158.3; LRMS (ES+): m/z 368.4 (100%, [M+H]$^+$); HRMS (ES+) calcd for C$_{22}$H$_{28}$N$_5$O [M+H]$^+$: 368.1506. found 368.1490.

5'-(Benzyl(4H-1,2,4-triazol-4-yl)amino)-2'-cyanobiphenyl-4-yl sulfamate (CAB06054)

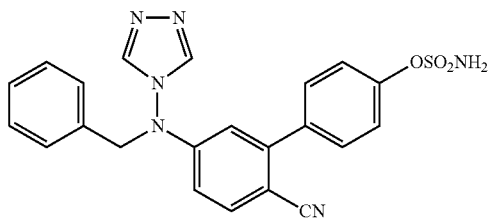

To a solution of sulfamoyl chloride (0399 g, 3.45 mmol) in DMA (1 mL) was added a solution of CAB06052 (0.152 g, 0.414 mmol) in DMA (5 mL) at 0° C. The clear solution was stirred for 2 hours at 0° C. and then for 4 hours at room temperature. EtOAc (50 mL) and water (20 mL) were added, the organic layer was separated, washed with water (2×30 mL) and brine (30 mL), dried (Na$_2$SO$_4$) and concentrated under reduced pressure. The residue was recrystallised from acetone/hexane to afford CAB06054 (0.127 g, 69%) as a white solid. Mp. 157-160° C.; $^1$H NMR (400 MHz, DMSO-d$_6$) δ 5.15 (s, 2H), 6.72-6.78 (m, 2H), 7.26-7.35 (m, 5H), 7.42 (AA'BB', 2H), 7.61 (AA'BB', 2H), 7.88 (d, J=8.6 Hz, 1H), 8.13 (s, 2H), 8.81 (s, 2H); $^{13}$C NMR (100.6 MHz, DMSO-d$_6$) δ 57.2, 101.8, 112.7, 113.9, 118.7, 122.5, 128.1, 128.5, 128.7, 130.1, 134.1, 135.6, 136.0, 143.4, 145.2, 150.6, 151.5; LRMS (ES+): m/z 447.3 (100%, [M+H]$^+$); HRMS (ES+) calcd for C$_{22}$H$_{19}$N$_6$O$_3$S [M+H]$^+$: 447.1234. found 447.1221.

5-((4-Bromobenzyl)(4H-1,2,4-triazol-4-yl)amino)-4'-hydroxybiphenyl-2-carbonitrile (CAB06056)

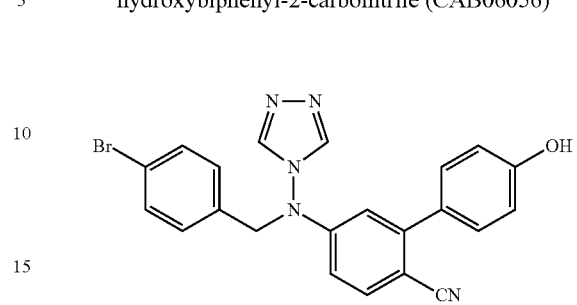

A solution of CAB06051 (0.536 g, 1.00 mmol) in AcOH (4 mL) and conc. HCl (2 mL) was heated to 100° C. for 1 h. After cooling to room temperature EtOAc (50 mL) was added and the mixture was washed with water (2×30 mL) and conc. NaHCO$_3$ solution (30 mL). The organic layer was dried (Na$_2$SO$_4$) and concentrated under reduced pressure. The residue was recrystallised from EtOAc/petrol ether (40-60° C.) to afford CAB06056 (0.433 g, 97%) as white solid. Mp. 222-224° C.; $^1$H NMR (400 MHz, DMSO-d$_6$) δ 5.11 (s, 2H), 6.63 (dd, J=8.6, 2.7 Hz, 2H), 6.70 (d, J=2.7 Hz, 1H) 6.87 (AA'BB', 2H), 7.27 (AA'BB', 2H), 7.33 (AA'BB', 2H), 7.52 (AA'BB', 2H), 8.82, (s, 2H), 9.82 (s, 1H); $^{13}$C NMR (100.6 MHz, DMSO-d$_6$) δ 56.5, 101.8, 112.1, 113.6, 115.5, 119.0, 121.3, 128.3, 129.9, 130.7, 131.6, 134.3, 135.5, 143.4, 146.4, 151.3, 158.3; LRMS (ES+): m/z 446.0 (100%, [C$_{22}$H$_{17}$$^{81}$BrN$_5$O]$^+$), 444.0 (95%, [C$_{22}$H$_{17}$$^{79}$BrN$_5$O]$^+$); HRMS (ES+) calcd for C$_{22}$H$_{17}$$^{81}$BrN$_5$O [M+H]$^+$:446.0611. found 446.0596.

5'-((4-Bromobenzyl)(4H-1,2,4-triazol-4-yl)amino)-2'-cyanobiphenyl-4-yl sulfamate (CAB06059)

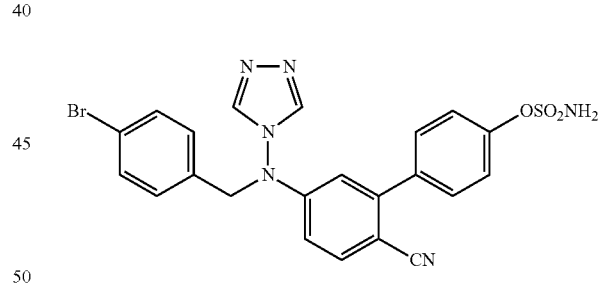

To a solution of sulfamoyl chloride (0.399 g, 3.45 mmol) in DMA (1 mL) was added a solution of CAB06056 (0.223 g, 0.50 mmol) in DMA (5 mL) at 0° C. The clear solution was stirred for 2 h at 0° C. and then for 4 h at room temperature. EtOAc (50 mL) and water (20 mL) were added, the organic layer was separated, washed with water (2×30 mL) and brine (30 mL), dried (Na$_2$SO$_4$) and concentrated under reduced pressure. The residue was purified by flash chromatography [SiO$_2$, CHCl$_3$/acetone (2:1)] to give CAB06059 (0.199 g, 76%) as a white solid. Mp. 122-123° C.; $^1$H NMR. (400 MHz, DMSO-d$_6$) δ 5.13 (s, 2H), 6.72-6.77 (m, 2H), 7.29 (AA'BB', 2H), 7.42 (AA'BB', 2H), 7.53 (AA'BB', 2H), 7.61 (AA'BB', 2H), 7.88 (d, J=8.6 Hz, 1H), 8.13 (s, 2H), 8.83 (s, 2H); $^{13}$C NMR (100.6 MHz, DMSO-d$_6$) δ 56.5, 102.0, 112.8, 114.0, 118.6, 121.4, 122.5, 130.1, 130.7, 131.6, 134.2, 135.7, 135.9, 143.4, 145.2, 150.6, 151.4; LRMS (ES+): m/z 525.1 (100%,

[C$_{22}$H$_{18}$$^{79}$BrN$_6$O$_3$S]$^+$), 527.1 (80%, [C$_{22}$H$_{18}$$^{81}$BrN$_6$O$_3$S]$^+$); HRMS (ES+) calcd for C$_{22}$H$_{18}$$^{79}$BrN$_6$O$_3$S [M+H]$^+$: 525.0339. found 525.0318.

(E/Z)-N-(4-(Benzyloxy)benzylidene)-1H-1,2,4-triazol-1-amine (CAB06086)

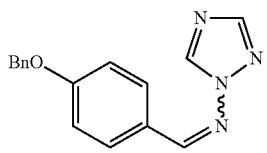 [SMILES: C(=Nn1cncn1)c1ccc(OCc2ccccc2)cc1]

To a solution of 1,2,4-triazole (1.38 g, 20.0 mmol) and NaOH (1.60 g, 400 mmol) in water was added hydroxylamine-O-sulfonic acid (2.26 g, 20.0 mmol) in small portions. The pink solution was heated to 70° C. for 1 hour and then concentrated under reduced pressure. The residue was suspended in EtOH (50 mL) and the solids were filtered off. To the filtrate was added 4-benzyloxybenzaldehyde (2.12 g, 10.0 mmol) and p-TsOH*H$_2$O (0.05 g) and the resulting mixture was heated to reflux for 15 minutes. The clear solution was left standing at room temperature overnight. The product crystallized from the solution and was collected by filtration to afford CAB06086 (2.39 g, 86%) as colorless plates. Mp. 121-123° C.; $^1$H NMR (400 MHz, DMSO-d$_6$) δ 5.20 (s, 2H), 7.18 (AA'BB', 2H), 7.30-7.48 (m, 5H), 7.91 (AA'BB', 2H), 8.15 (s, 1H), 8.89 (s, 1H), 9.17 (s, 1H); $^{13}$C NMR (100.6 MHz, DMSO-d$_6$) δ 69.5, 115.4, 124.7, 127.8, 128.0, 128.5, 130.6, 136.5, 142.0, 149.5, 153.4, 161.5; LRMS (ES+): m/z 279.1 (100%, [M+H]$^+$); HRMS (ES+) calcd for C$_{16}$H$_{15}$N$_4$O [M+H]$^+$: 279.1240. found 279.1245.

N-(4-(Benzyloxy)benzyl)-1H-1,2,4-triazol-1-amine (CAB06089)

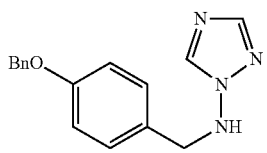 [SMILES: c1ccc(COc2ccc(CNn3cncn3)cc2)cc1]

To a solution of CAB06086 (1.392 g, 5.0 mmol) in THF (20 mL) and MeOH (20 mL) was added NaBH$_4$ (0.20 g 5.28 mmol) at 0° C. The mixture was stirred for 1 hour at 0° C. and then for 12 hours at room temperature (TLC-control). The mixture was poured into water (50 mL) and the products were extracted with EtOAc (3×40 mL). The combined organic fractions were dried (Na$_2$SO$_4$) and concentrated under reduced pressure. The residue was purified by flash chromatography [SiO$_2$, actone/CHCl$_3$ (1:1)] to afford CAB06089 (1.163 g, 83%) as a white solid. Mp. 123-124° C.; $^1$H NMR (400 MHz, DMSO-d$_6$) δ 4.16 (d, J=3.5 Hz, 2H), 5.06 (s, 2H), 6.93 (AA'BB', 2H), 7.16 (AA'BB', 2H), 7.29-7.46 (m, 6H), 7.89 (s, 1H), 8.14 (s, 1H); $^{13}$C NMR (100.6 MHz, DMSO-d$_6$) δ 54.0, 69.1, 114.5, 127.7, 127.8, 128.4, 128.9, 129.9, 137.1, 142.7, 149.5, 157.7; LRMS (ES+): 281.0 (100%, [M+H]$^+$); HRMS (ES+) calcd for C$_{16}$H$_{17}$N$_4$O [M+H]$^+$: 281.1397. found 281.1401; Anal. Calcd for C$_{16}$H$_{16}$FN$_4$O: C, 68.55; H, 5.75; N, 19.99. Found C, 68.2; H, 5.80; N, 20.0.

5-((4-(Benzyloxy)benzyl)(1H-1,2,4-triazol-1-yl)amino)biphenyl-2-carbonitrile (CAB06090)

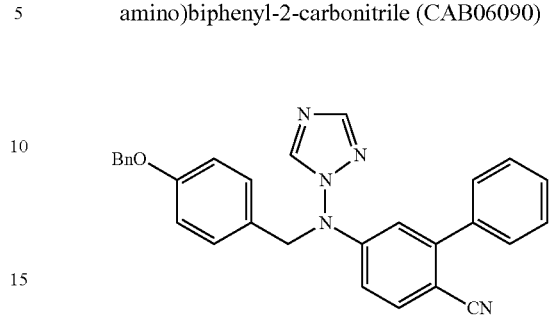

To a solution of CAB06089 (0.280 g, 1.00 mmol) in DMSO (10 mL) was added KOtBu (0.123 g, 1.10 mmol). The mixture was stirred for 0.5 hours at room temperature before CAB06020 (0.197 g, 1.00 mmol) was added and stirring was continued overnight. Then water (30 mL) was added and the mixture was extracted with EtOAc (3×30 mL). The combined organic extracts were dried (Na$_2$SO$_4$) and concentrated under reduced pressure. The residue was purified by flash chromatography [SiO$_2$, acetone/CHCl$_3$ (1:6)] to afford CAB06090 (0.362 g, 79%) as a colorless oil, which was crystallized from MeOH (colorless crystals). Mp. 112-113° C.; $^1$H NMR (400 MHz, DMSO-d$_6$) δ 5.02 (s, 2H), 5.06 (s, 2H), 6.68 (dd, J=8.6, 2.3 Hz, 1H), 6.84 (d, J=2.4 Hz, 1H), 6.95 (AA'BB', 2H), 7.25 (AA'BB', 2H), 7.30 7.52 (m, 10H), 7.84 (d, J=8.6 Hz, 1H), 8.16 (s, 1H), 8.56 (s, 1H); $^{13}$C NMR (100.6 MHz, DMSO-d$_6$) δ 56.3, 69.2, 102.5, 113.6, 114.7, 115.0, 118.7, 126.7, 127.7, 127.8, 128.4, 128.5, 128.7, 128.9, 130.1, 135.3, 136.9, 137.8, 145.1, 146.1, 151.1, 151.4, 158.1; LRMS (ES+): m/z 458.3 (100%, [M+H]$^+$); HRMS (ES+) calcd for C$_{29}$H$_{24}$N$_5$O [M+H]$^+$: 458.1975. found 458.1972; Anal. Calcd for C$_{29}$H$_{23}$N$_5$O; C, 76.13; H, 5.07; N, 15.31. Found C, 76.0; H, 5.04; N, 15.2.

5-((4-Hydroxybenzyl)(1H-1,2,4-triazol-1-yl)amino)biphenyl-2-carbonitrile (CAB06093)

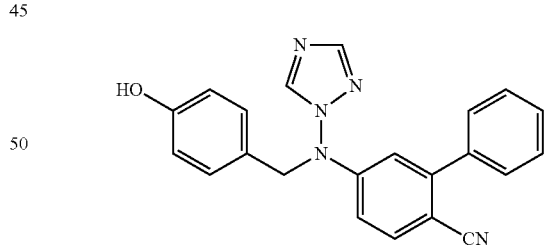

To a solution of CAB06090 (0.273 g, 0.597 mmol) in THF (10 mL) and methanol (10 mL) was added Pd—C (0.05 g, 5% Pd). The mixture was stirred under H$_2$-atmosphere for 18 hours before the catalyst was filtered off (celite) and the volatiles were removed under reduced pressure. The residue was recrystallized from EtOAc/n-hexane afford CAB06093 (0.210 g, 96%) as colorless crystals. Mp. 169-170° C.; $^1$H NMR (400 MHz, DMSO-d$_6$) δ 4.93 (s, 2H), 6.67 (AA'BB', 2H), 6.69 (dd, J=8.6, 2.3 Hz, 1H), 6.83 (d, J=2.3 Hz, 1H), 7.10 (AA'BB', 2H), 7.45-7.56 (m, 5H), 7.84 (d, J=8.6 Hz, 1), 8.48 (s, 1H), 9.46 (s, 1H); $^{13}$C NMR (100.6 MHz, DMSO-d$_6$) δ 56.4, 102.4, 113.7, 115.0, 115.2, 118.8, 124.5, 128.6, 128.7, 128.9, 130.2, 135.3, 137.8, 145.1, 146.1, 151.1, 151.4, 157.1; LRMS (ES+): m/z 368.2 (100%, [M+H]+); HRMS (ES+) calcd for $C_{22}H_{18}N_5O$ [M+H]+: 368.1506. found 368.1495.

4-(((6-Cyanobiphenyl-3-yl)(1H-1,2,4-triazol-1-yl)amino)methyl)phenyl sulfamate (CAB06094)

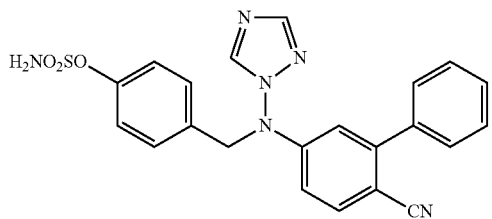

To a solution of sulfamoyl chloride (0.399 g, 3.45 mmol) in DMA. (1 mL) was added a solution of CAB06093 (0.100 g, 0.272 mmol) in DMA (5 mL) at 0° C. The clear solution was stirred for 2 hours at 0° C. and then for 4 hours at room temperature, EtOAc (50 mL) and water (20 mL) were added, the organic layer was separated, washed with water (2×30 mL) and brine (30 mL), dried ($Na_2SO_4$) and concentrated under reduced pressure. The residue was purified by flash chromatography [$SiO_2$, $CHCl_3$/acetone (1:2)] to afford CAB06094 (0.103 g, 85%) as a colorless foam. $^1$H NMR (400 MHz, $CDCl_3$) δ 4.92 (s, 2H), 5.30 (s, 2H), 6.65 (dd, J=8.6, 2.3 Hz, 1H), 6.7.3 (d, J=2.3 Hz, 1H), 7.20-7.34 (m, 5H), 7.40-7.48 (m, 4H), 7.66 (d, J=8.6 Hz, 1H), 7.85 (s, 1H), 7.98 (s, 1H); $^{13}$C NMR (100.6 MHz, $CDCl_3$) δ 57.6, 105.2, 111.9, 116.0, 118.5, 122.7, 128.6, 128.8, 129.1, 130.1, 133.0, 135.3, 137.7, 144.1, 147.4, 150.2, 151.0, 151.5; LRMS (ES+): m/z 447.2 (80%, [M+H]+), 378.1 (100%); HRMS (ES+) calcd for $C_{22}H_{19}N_6O_3S$ [M+H]+: 447.1234. found 447.1230.

2-(Benzofuran-2-yl)-4-fluorobenzonitrile (AUP011584)

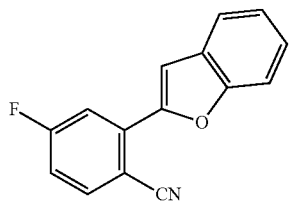 [SMILES: N#Cc1ccc(F)cc1-c1cc2ccccc2o1]

A mixture of 2-bromo-4-fluorobenzonitrile (515 g, 25.65 mmol), benzofuran-2-ylboronic acid (5.0 g, 30.8 mmol), 1,2-dimethoxyethane (25 mL) and 2M $Na_2CO_3$ (40 mL) was heated to reflux before $Pd_2(dba)_3$ (100 mg) was added and heating was continued for 5 h. After cooling to r.t, EtOAc (20 mL) was added to dissolve the product. The mixture was filtered through celite, the organic layer was separated, dried ($Na_2SO_4$) and concentrated under reduced pressure. The residue was dissolved in minimum amount of $CHCl_3$ and passed through Silica. Solvent was evaporated and the residue was first purified by crystallisation from a mixture $CHCl_3$/PE (98/2). The filtrate was purified by Combiflash chromatography (40 g column, 13 g Silica, gradient of eluent from PE to PE/EtOAc 9/1) to give the title compound as light yellow solid purified by rinsing with PE to give at the end a white solid (5.15 g). This solid had to be purified an ultimate time by drying under vacuum at 80° C. for O/N. Finally, pure expected compound was obtained as a off-white solid in 59% yield (3.6 g); mp 123-124° C.; $^1$H NMR (270 MHz, $CDCl_3$) 87.13 (1H, td, J=2.5 and 7.3 Hz, ArH), 7.30 (1H, t, J=7.7 Hz, ArH), 7-40 (1H, t, J=77 Hz, ArH), 7.56 (1H, d, J=7.7 Hz, ArH), 7.69 (1H, d, J=73 Hz, ArH), 7.76-7.86 (3H, m, ArH); Anal. Calcd. for $C_{15}H_8FNO$: C, 75.94, H, 3.40, N, 5.90. Found: C, 75 70, H, 3.37, N, 5.97%.

4-(4H-1,2,4-Triazol-4-ylamino)-2-(benzofuran-2-yl)benzonitrile (AUP01171-1)

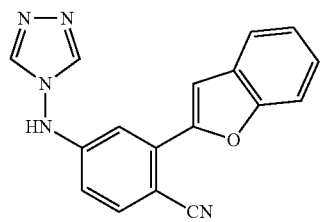 [SMILES: N#Cc1ccc(Nn2cnnc2)cc1-c1cc2ccccc2o1]

To a solution of 4H-1,2,4-triazol-4-amine (0.709 g, 8.435 mmol) in DMSO (10 mL) was added KOtBu (0.946 g, 8.435 mmol). The mixture was stirred for 30 min. at r.t before AUP01158-1 (1.0 g, 4.22 mmol) was added and stirring was continued for 1 h. The mixture was poured into crushed ice and neutralized with 2M $KHSO_4$ solution (4 mL). The precipitate was filtered off, washed with water (5×20 mL) and dried ($P_2O_5$). The solid was washed with acetone (20 mL) and the filtrate purified by Combiflash chromatography (24 g column, 5 g silica, gradient of eluent from $CHCl_3$/Acetone 6/4 to Acetone for 25 min.) to give the title compound as a white solid (990 mg, 78%); rap 278-279° C.; $^1$H NMR (270 MHz, DMSO-$d_6$) δ 6.55 (1H, dd, J=2.2 and 8.7 Hz, ArH), 7.11 (1H, d, J=2.2 Hz, ArH), 7.32 (1H, t, J=7.5 Hz, ArH), 7.41 (1H, t, J=7.0 Hz, ArH), 7.66 (1H, d, J=8.3 Hz, ArH), 7.68 (1H, s, ArH), 7.80 (1H, d, J=7.4 Hz, ArH), 7.85 (1H, d, J=8.5 Hz, ArH), 8.90 (2H, s, ArH), 10.40 (1H, s broad, NH); Anal. Calcd. for $C_{17}H_{11}N_5O$: C, 67.77; H, 3.68; N, 23.24. Found: C, 6790, H, 3:64, N, 22.80%.

2-(Benzofuran-2-yl)-4-((4-(benzyloxy)benzyl)(4H-1,2,4-triazol-4-yl)amino)benzonitrile (AUP01174-1)

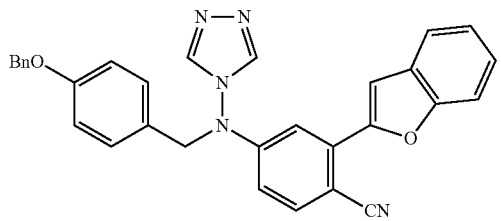 [SMILES: N#Cc1ccc(N(Cc2ccc(OCc3ccccc3)cc2)n2cnnc2)cc1-c1cc2ccccc2o1]

To a solution of AUP01171-1 (603 mg, 2.0 mmol) in DMF (10 mL) was added NaH (82 mg, 2.04 mmol) at 0° C. and the mixture was stirred at r t for 30 min. Then, 4-benzyloxybenzyl chloride (466 mg, 2.0 mmol) was added and stirring was continued for 18 h. The reaction mixture was diluted with EtOAc (30 mL), washed with water (3×30 mL) and brine (30 mL), dried ($Na_2SO_4$) and concentrated under reduced pressure. The residue was purified by Combiflash chromatography (24 g column, 5 g silica, gradient of eluent from CHCl₃ to CHCl₃/Acetone 8/2 for 25 min.) to give the title compound as a white solid after rinsing with MeOH (825 mg, 83%); mp 200-201° C.; ¹H NMR (270 MHz, DMSO-d₆) δ 5.06 (2H, s, CH₂), 5.08 (2H, s, CH₂), 6.76 (1H, dd, J=2:2 and 8:5 Hz, ArH), 6.97 (2H, d, J=8.8 Hz, ArH), 7.24-7.42 (10H, m, ArH), 7.64 (1H, d, J=8.0 Hz, ArH), 7.71 (1H, s, ArH), 7.79 (1H, d, J=7.4 Hz, ArH), 7.91 (1H, d, J=8.8 Hz, ArH), 8.81 (2H, s, ArH); HRMS (ESI) calcd. for $C_{31}H_{24}N_5O_2$ (M+H)⁺ 498.1925. found 498.1920.

2-(Benzofuran-2-yl)-4-((4-hydroxybenzyl)(4H-1,2,4-triazol-4-yl)amino)benzonitrile (AUP01176-1)

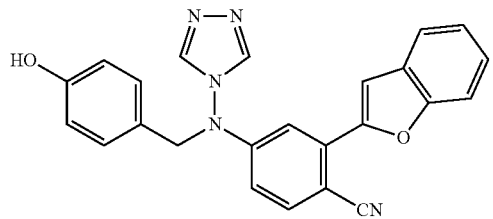 [SMILES: N#Cc1ccc(N(Cc2ccc(O)cc2)n2cnnc2)cc1-c1cc2ccccc2o1]

Palladium on charcoal (5%, 20 mg) was added to a solution of AUP01174-1 (746 mg, 1.50 mmol) in THF (25 mL) and MeOH (25 mL). The solution was stirred under an atmosphere of H₂ (provided by addition from a balloon) overnight. The excess H₂ was removed and the reaction mixture was filtered through Celite washing with CH₂Cl₂/MeOH (8/2), then the solvent was removed in vacuo. The solid was washed with MeOH (10 mL) to give the title compound as a white solid (527 mg, 86%); mp 222-223° C.; ¹H NMR (270 MHz, DMSO-d₆) δ 5.01 (2H, s, CH₂), 6.68 (2H, d, J=8.5 Hz, ArH), 6.77 (1H, dd, J=2.5 and 8.8 Hz, ArH), 7.10 (2H, d, J=8.5 Hz, ArH), 7.29-7.41 (3H, m, ArH), 7.64 (1H, d, J=8.0 Hz, ArH), 7.71 (1H, s, ArH), 7.80 (1H, d, J=7.7 Hz, ArH), 7.91 (1H, d, J=8.8 Hz, ArH), 8.76 (2H, s, ArH), 9.53 (1H, s broad, OH); HRMS (ESI) calcd. for $C_{24}H_{38}N_5O_2$ (M+H)⁺408.1455. found 408.1450.

4-(((3-(Benzofuran-2-yl)-4-cyanophenyl)(4H-1,2,4-triazol-4-yl)amino)methyl)phenyl sulfamate (AUP2011814)

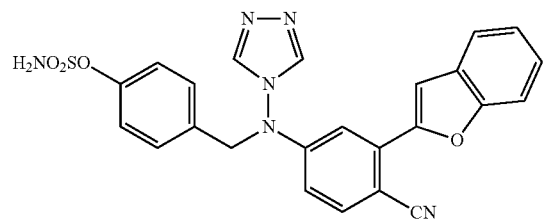

A solution of sulfamoyl chloride in toluene (0.5 M, 4.0 mL) was concentrated in vacuo at 30° C. to furnish a yellow oil which solidified upon cooling in an ice bath. DMA (2.0 mL) and AUP01176-1 (203 mg, 0.5 mmol) were subsequently added and the mixture was allowed to warm to room temperature and stirred overnight. The resulting solution was added to brine (20 mL) and the product was extracted with EtOAc (20 mL×5). The organic layers were combined, washed with brine (20 mL×3), dried (Na₂SO₄) and the solvent was removed in vacuo. Purification of the crude by rinsing and washing with cold MeOH gave the title compound as a white solid (210 mg, 86%); mp 202-203° C.; ¹H NMR (270 MHz, DMSO-d₆) δ 5.21 (2H, s, CH₂), 6.75 (1H, dd, J=2.8 and 8.8 Hz, ArH), 7.24-7.47 (71-1, in, ArH), 7.64 (1H, d, J=8.0 Hz, ArH), 7.70 (1H, s, ArH), 7.80 (1H, d, J=7.7 Hz, ArH), 7.93 (1H, d, J=8.8 Hz, ArH), 8.05 (2H, s broad, NH₂), 8.90 (2H, s, ArH$_{triazol}$); HRMS (ESI) calcd. for $C_{24}H_{19}N_6O_4S$ (M+H)⁺ 487.1183. found 487.1167.

2-(Benzofuran-2-yl)-4-((3-chloro-4-hydroxybenzyl)(4H-1,2,4-triazol-4-yl)amino)benzonitrile (AUP01177-1)

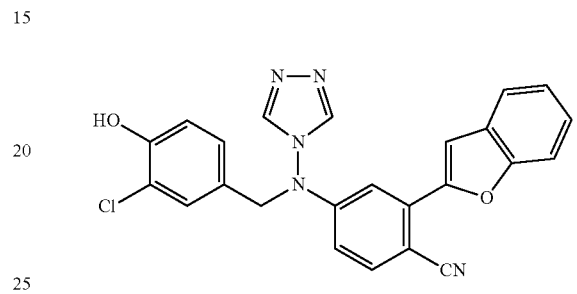

A solution of 2-chloro-4-(hydroxymethyl)phenol (CAB06028) (317 mg, 2.00 mmol) in SOCl₂ (7 mL) was stirred at r.t for 30 min. The excess SOCl₂ was removed under reduced pressure (rotavap) and the residue was dissolved in DMF (7 mL). Then AUP01171-1 (603 mg, 2.00 mmol) and K₂CO₃ (1.84 g, 13.37 mmol) were added and the mixture was stirred overnight. EtOAc (30 mL) and 2M KHSO₄ (10 mL until pH=4-5) were added, the organic layer was separated, washed with water (20 mL) and brine (30 mL), dried (Na₂SO₄) and concentrated under reduced pressure. Solid was purified by rinsing with hot IPA (propan-2-01) (6 mL) and well sonicated to give the title compound as a white solid (651 mg). The filtrate was purified by Combiflash chromatography (12 g column, 3 g silica, gradient of eluent from CHCl₃/acetone 9/1 to acetone for 15 min) to give the title compound as a white solid (40 mg). Finally, AUP01177-1 was obtained in 78% yield (691 mg); mp 196-197° C.; ¹H NMR (270 MHz, DMSO-d₆) δ 5.03 (2H, s, CH₂), 6.75 (1H, dd, J=2.5 and 8.8 Hz, 6.88 (1H, d, J=8.3 Hz, ArH), 7.07 (1H, dd, J=1.9 and 8.3 Hz, ArH), 7.26-7.45 (4H, m, ArH), 7.64 (1H, d, J=8.0 Hz, ArH), 7.71 (1H, s, ArH), 7.80 (1H, d, J=7.7 Hz, ArH), 7.92 (1H, d, J=8.8 Hz, ArH), 8.83 (2H, s, ArH), 10.33 (1H, s broad, OH); HRMS (ESI) calcd, for $C_{24}H_{17}ClN_5O_2$ (M+H)⁺442.1065. found 442.1059.

4-(((3-(benzofuran-2-yl)-4-cyanophenyl)(4H-1,2,4-triazol-4-yl)amino)methyl)-2-chlorophenyl sulfamate (AUP01184-1)

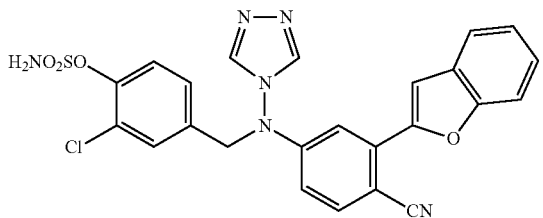

A solution of sulfamoyl chloride in toluene (0.5 M, 4.0 mL) was concentrated in vacuo at 30° C. to furnish a yellow oil which solidified upon cooling in an ice bath. DMA (2.0 mL) and AUP01177-1 (221 mg, 0.5 mmol) were subsequently added and the mixture was allowed to warm to room temperature and stirred overnight. The resulting solution was added to brine (20 mL) and the product was extracted with EtOAc (20 mL×10). The organic layers were combined, washed with brine again (20 mL×3) and the solvent was removed in vacuo. Purification of the crude by rinsing and washing with cold MeOH give the title compound as white solid (226 mg, 87%); mp 214-215° C.; $^1$H NMR (270 MHz, DMSO-d$_6$) δ 5.21 (2H, s, CH$_2$), 6.74 (1H, dd, J=2.7 and 8.8 Hz, ArH), 7.25 (1H, d, J=2.5 Hz, ArH), 7.33 (1H, t, J=7.2 Hz, ArH), 7.39-7.49 (3H, m, ArH), 7.63 (1H, d, J=8.5 Hz, ArH), 7.65 (1H, s, ArH), 7.70 (1H, s, ArH), 7.80 (1H, d, J=7.7 Hz, ArH), 7.94 (1H, d, J=8.8 Hz, ArH), 8.32 (2H, s broad, NH$_2$), 8.96 (2H, s, ArH$_{triazol}$); HRMS (ESI) calcd. for C$_{24}$H$_{18}$ClN$_6$O$_4$S (M+H)$^+$521.0793. found 521.0788.

2-((Benzofuran-2-yl)-4-((3-bromo-4-hydroxybenzyl)(4H-1,2,4-triazol-4-yl)amino)benzonitrile (AUP01189-1)

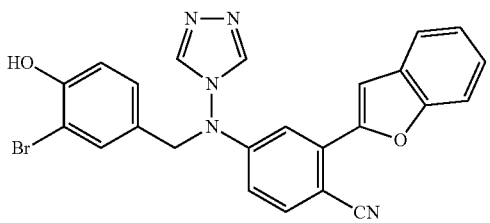 [SMILES: N#Cc1ccc(N(Cc2ccc(O)c(Br)c2)n2cnnc2)cc1-c1cc2ccccc2o1]

A solution of 2-bromo-4-(hydroxymethyl)phenol (203 mg, 1.00 mmol) in SOCl$_2$ (3.5 mL) was stirred at r.t for 30 min. The excess SOCl$_2$ was removed under reduced pressure (vacuum pump) and the residue was dissolved in DMF (3.5 mL). Then AUP01171-1 (301 mg, 1.00 mmol) and K$_2$CO$_3$ (921 mg, 6.67 mmol) were added and the mixture was stirred overnight. EtOAc (30 mL) and 2M KHSO$_4$ (5 mL until pH=4-5) were added, the organic layer was separated, washed with water (20 mL) and brine (30 mL), dried (Na$_2$SO$_4$) and concentrated under reduced pressure. The crude was purified by Combiflash chromatography (24 g column, 8 g silica, gradient of eluent from CHCl$_3$ to acetone for 30 min.) to give the title compound as a white solid (211 mg after rinsing with cold MeOH, 43%) and starting material was recovered as a white solid (88 mg, 29%); mp 147-148° C.; $^1$H NMR (270 MHz, DMSO-d$_6$) δ 5.03 (2H, s, CH$_2$), 6.75 (1H, dd, J=2.8 and 8.7 Hz, ArH), 6.87 (1H, d, J=8.3 Hz, ArH), 7.11 (1H, dd, J=1.9 and 8.2 Hz, ArH), 7.30-7.48 (4H, m, ArH), 7.64 (1H, d, J=8.3 Hz, ArH), 7.71 (1H, s, ArH), 7.80 (1H, d, J=7.7 Hz, ArH), 7.92 (1H, d, J=8.8 Hz, ArH), 8.83 (2H, s, ArH$_{triazol}$), 10.40 (1H, s broad, OH); HRMS (ESI) calcd. for C$_{24}$H$_{17}$BrN$_5$O$_2$ (M+H)$^+$486.0560. found 4486.0562.

4-(((3-(Benzofuran-2-yl)-4-cyanophenyl)(4H-1,2,4-triazol-4-yl)amino)methyl)-2-bromophenyl sulfamate (AUP01185-1)

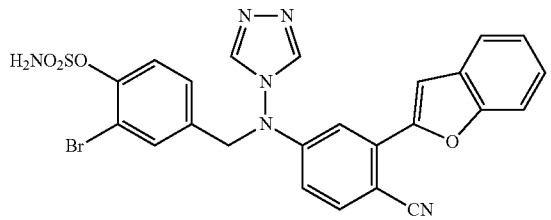

A solution of sulfamoyl chloride in toluene (0.5 M, 7.73 mL) was concentrated in vacuo at 30° C. to furnish a yellow oil which solidified upon cooling in an ice bath. DMA (4.0 mL) and AUP01189-1 (470 mg, 0.97 mmol) were subsequently added and the mixture was allowed to warm to room temperature and stirred overnight. The resulting solution was added to brine (20 mL) and the product was extracted with EtOAc (20 mL×5). The organic layers were combined, washed with brine (20 mL×3), dried (Na$_2$SO$_4$) and the solvent was removed in vacuo. The crude was purified by Combiflash chromatography (24 g column, 5 g silica, gradient of eluent from CHCl$_3$ to acetone 30 min) to give the title compound as a light yellow solid which was purified by rinsing and washing with cold MeOH giving the title compound as white solid (198 mg, 36%); mp 199-200° C.; $^1$H NMR (270 MHz, DMSO-d$_6$) δ 5.21 (2H, s, CH$_2$), 6.73 (1H, dd, J=2.7 and 8.8 Hz, ArH), 7.26 (1H, d, J=2.5 Hz, ArH), 7.33 (1H, t, J=7.2 Hz, ArH), 7.42 (1H, t, J=7.7 Hz, ArH), 7.44-7.47 (2H, m, ArH), 7.64 (1H, d, J=8.0 Hz, ArH), 7.70 (1H, s, ArH), 7.78 (1H, s, 7.80 (1H, d, J=8.5 Hz, ArH), 7.94 (1H, d, J=8.8 Hz, ArH), 8.32 (2H, a broad, NH$_2$), 8.96 (2H, s, ArH$_{triazol}$); HRMS (ESI) calcd. for C$_{24}$H$_{18}$BrN$_6$O$_4$S (M+H)$^+$565.0288. found 565.0296.

4-Fluoro-2-(furan-2-yl)benzonitrile (AUP01160-1)

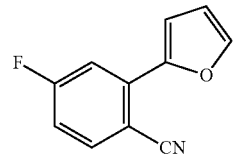 [SMILES: N#Cc1ccc(F)cc1-c1ccco1]

Following the same procedure used for AUP01158-1, AUP01160-1 was prepared from 2-bromo-4-fluorobenzonitrile (5.0 g, 25.0 mmol), furan-2-ylboronic acid (3.36 g, 30.0 mmol), Pd$_2$(dba)$_3$ (100 mg), 1,2-dimethoxyethane (25 mL) and 2M Na$_2$CO$_3$ (40 mL). The crude was purified by Combiflash chromatography (24 g column, 8 g silica., gradient of eluent from PE to PE/EtOac 9/1) to give the title compound as a light yellow solid. This solid had to be purified an ultimate time by drying under vacuum at 40° C. for 5 days. Finally, pure expected compound was obtained as a white off solid in 35% yield (1.65 g); mp 55-56° C.; $^1$H NMR (270 MHz, CDCl$_3$) δ 6.58-6.59 (1H, m, ArH), 7.02 (1H, td, J=2.7 and 8.0 Hz, ArH), 7.40 (1H, d, J=3.6 Hz, ArH), 7.57 (1H, s, ArH), 7.62

(1H, d, J=2.7 Hz, ArH), 7.70 (1H, dd, J=5.5 and 7.7 Hz, ArH); HRMS (ESI) calcd. for $C_{11}H_7FNO$ (M+H)$^+$ 188.0506. found 188.0513.

4-(4H-1,2,4-Triazol-4-ylamino)-2-(furan-2-yl)benzonitrile (AUP01173-1)

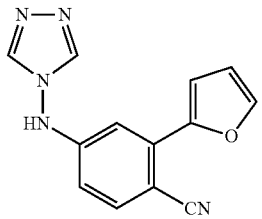 [SMILES: N#Cc1ccc(Nn2cnnc2)cc1-c1ccco1]

Following the same procedure used for AUP01171-1, AUP01173-1 was prepared from 4H-1,2,4-triazol-4-amine (1.66 g, 19.8 mmol), KOtBu (2.22 g, 19.8 mmol), compound AUP01160-1 (1.85 g, 9.88 mmol) and DMSO (23 mL). The mixture was poured into crushed ice and neutralized with 2M KHSO$_4$ solution (6 mL). The precipitate was filtered off, washed with water (5×20 mL) and dried (P$_2$O$_5$). The solid was washed with acetone (10 mL) and the filtrate purified by Combiflash chromatography (24 g column, 5 g silica, gradient of eluent from CH$_2$Cl$_2$ to MeOH for 25 min.) to give the title compound as a light brown solid (1.70 g, 68%); mp 217-218° C.; $^1$H NMR (270 MHz, DMSO-d$_6$) δ 6.52 (1H, dd, J=2.2 and 8.5 Hz, ArH), 6.69-6.71 (1H, m, ArH), 6.84 (1H, d, J=2.2 Hz, ArH), 7.22 (1H, d, J=3.6 Hz, ArH), 7.77 (1H, d, J=8.5 Hz, ArH), 7.89 (1H, d, J=2.0 Hz, ArH), 8.89 (2H, s, ArH), 10.35 (1H, s broad, NH); $^{13}$C NMR (100 MHz, DMSO-d$_6$) 97.12 (C), 107.87 (CH), 110.58 (CH), 111.38 (CH), 112.51 (CH), 119.12 (C), 133.79 (C), 136.35 (CH), 144.11 (CH×2), 144.60 (CH), 148.86 (C), 151.12 (C); HRMS (ESI) calcd. for $C_{13}H_{10}N_5O$ (M+H)$^+$ 252.0880. found 252.0876.

4-((4-(Benzyloxy)benzyl)(4H-1,2,4-triazol-4-yl)amino)-2-(furan-2yl)benzonitrile (AUP02004-1)

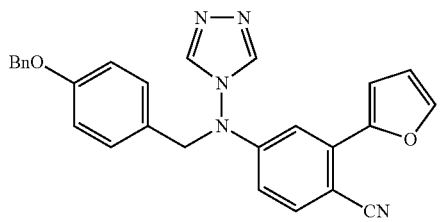 [SMILES: N#Cc1ccc(N(Cc2ccc(OCc3ccccc3)cc2)n2cnnc2)cc1-c1ccco1]

To a solution of AUP01173-1 (502 mg, 2.0 mmol) in DMF (10 mL) was added NaH (82 mg, 2.04 mmol) at 0° C. and the mixture was stirred at r.t for 0.30 min. Then, the 4-benzyloxybenzyl chloride (466 mg, 2.0 mmol) was added and stirring was continued for 18 h. The reaction mixture was diluted with EtOAc (30 mL), washed with water (3×30 mL) and brine (30 mL), dried (Na$_2$SO$_4$) and concentrated under reduced pressure. The residue was purified by Combiflash chromatography (24 g column, 5 g silica, gradient of eluent from CHCl$_3$ to CHCl$_3$/Acetone 8/2 for 25 min.) to give the title compound as a white solid after rinsing with a mixture of PE/EtOAc 2/8 (661 mg, 74%); mp 181-182° C.; $^1$H NMR (270 MHz, DMSO-d$_6$) δ 5.04 (2H, s, CH$_2$), 5.06 (2H, s, CH$_2$), 6.70-6.76 (2H, m, ArH), 6.95 (2H, d, J=8.5 Hz, ArH), 7.00 (1H, d, J=2.5 Hz, ArH), 7.21-7.26 (3H, m, ArH), 7.30-7.45 (5H, m, ArH), 7.84 (1H, d, J=8.8 Hz, ArH), 7.89 (1H, d, J=1.6 Hz, ArH), 8.78 (2H, s, ArH$_{triazol}$); HRMS (ESI) calcd. for $C_{27}H_{22}N_5O_2$ (M+H)$^+$ 448.1768. found 448.1760.

2-(Furan-2-yl)-4-((4-hydroxybenzyl)(4H-1,2,4-triazol-4-yl)amino)benzonitrile (AUP02005-1)

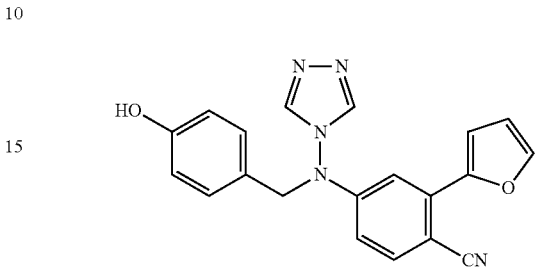

Palladium on charcoal (5%, 20 mg) was added to a solution of AUP02004-1 (600 mg, 1.34 mmol) in THF (20 mL) and MeOH (20 mL). The solution was stirred under an atmosphere of H$_2$ (provided by addition from a balloon) overnight. The excess H$_2$ was removed and the reaction mixture was filtered through Celite washing with CH$_2$Cl$_2$/MeOH (8/2), then the solvent was removed in vacuo. The solid was washed with MeOH (5 mL) to give the title compound as a white solid (275 mg, 57%); mp 218-219° C.; $^1$H NMR (270 MHz, DMSO-d$_6$) δ 4.96 (2H, s, CH$_2$), 6.67 (2H, d, J=8.3 Hz, ArH), 6.70-6.75 (2H, m, 7.00 (1H, d, J=2.5 Hz, ArH), 7.07 (2H, d, J=8.5 Hz, ArH), 7.25 (1H, d, J=3.6 Hz, ArH), 7.83 (1H, d, J=8.8 Hz, ArH), 7.89 (1H, d, J=1.1 Hz, ArH), 8.73 (2H, s, ArH$_{triazol}$), 9.50 (1H, s broad, OH); HRMS (ESI) calcd. for $C_{20}H_{16}N_5O_2$ (M+H)$^+$ 358.1299. found 358.1292.

4-(((4-Cyano-3-(furan-2-yl)phenyl)(4H-1,2,4-triazol-4-yl)amino)methyl)phenyl sulfamate (AUP02011-1)

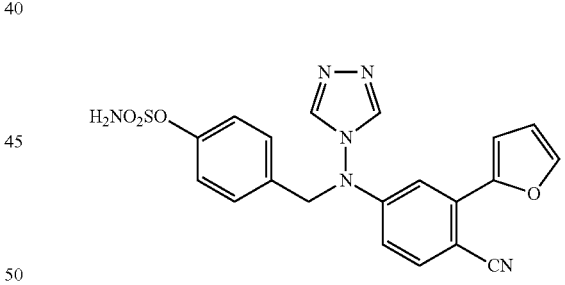

A solution of sulfamoyl chloride in toluene (0.5 M, 6.7 mL) was concentrated in vacuo at 30° C. to furnish a yellow oil which solidified upon cooling in an ice bath. DMA (1.8 mL) and AUP02005-1 (150 mg, 0.42 mmol) were subsequently added and the mixture was allowed to warm to room temperature and stirred overnight. The resulting solution was added to brine (20 mL) and the product was extracted with EtOAc (20 mL×5). The organic layers were combined, washed with brine (20 mL×3), dried (Na$_2$SO$_4$) and the solvent was removed in vacuo. The crude was purified by Combiflash chromatography (12 g column, 3 g silica, gradient of eluent from CHCl$_3$ to acetone 30 min) to give the title compound as a light yellow solid which was purified by rinsing and washing with cold MeOH giving the title compound as white solid (134 mg, 73%); mp 177-178° C.; $^1$H NMR (270 MHz, DMSO-d$_6$) δ 5.16 (2H, s, CH$_2$), 6.70-6.72 (2H, m, ArH), 6.97

(1H, d, J=2.8 Hz, ArH), 7.23 (1H, d, J=5.2 Hz, ArH), 7.25 (2H, s, ArH), 7.43 (2H, d, J=8.5 Hz, ArH), 7.85 (1.11, d, J=8.5 Hz, ArH), 7.90 (1H, d, J=1.7 Hz, ArH), 8.01 (2H, s broad, NH$_2$), 8.81 (2H, s, ArH$_{triazol}$); HRMS (ESI) calcd. for C$_{20}$H$_{17}$N$_6$O$_4$S (M+H)$^+$437.1027. found 437.1028.

Methyl 2,6-difluoro-4-hydroxybenzoate (PMW03136)

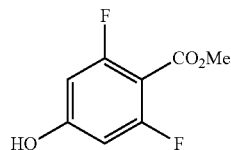 [SMILES: COC(=O)c1c(F)cc(O)cc1F]

SOCl$_2$ (4.16 g, 30.1 mmol) was added to a solution of 2,6-difluoro-4-hydroxybenzoic acid (1.50 g, 8.62 mmol) in MeOH (20 mL) and the resulting mixture was heated at reflux for 24 h. After cooling the solvent was removed in vacuo to give the title compound (1.62 g, 99%) as a white crystalline solid; mp 177.5-180° C.; $^1$H NMR (270 MHz, DMSO-d$_6$) 3.80 (3H, s, CH$_3$), 6.50-6.60 (2H, m, ArH), 11.16 (1H, s, OH)

3,5-Difluoro-4-(hydroxymethyl)phenol (PMW03144)

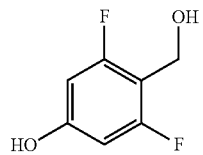

A solution of PMW03136 (1.70 g, 9.14 mmol) in THF (10 mL) was slowly added to a suspension of LiAlH$_4$ (1.39 g, 36.6 mmol) in THF (20 ml). After 45 minutes the reaction was quenched by the cautious addition of EtOAc (10 ml), H$_2$O (20 ml) and 3M HCl (10 mL). The product was extracted with EtOAc (2×40 ml) and the combined organics were washed with sat. aq. NaHCO$_3$ (50 mL) dried (MgSO$_4$) and the solvent was removed in vacuo. The crude product was using the Flashmaster II (EtOAc/hexane) to give the title compound (1.03 g, 70%) as a white solid; nip 160° C. (dec); $^1$H NMR (270 MHz, DMSO-d$_6$) 4.36 (1H, d, J=5.4, CH$_2$), 5.03 (1H, d, J=5.4, OH), 6.39-6.50 (2H, m, ArH), 10.43 (1H, s, OH); LC/MS (ES$^-$) t$_r$=0.90 min, m/z 158.9 (M$^-$−1, 100%), 140.9 (60).

5-((2,6-Difluoro-4-hydroxybenzyl)(4H-1,2,4-triazol-4-yl)amino)biphenyl-2-carbonitrile (PMW04146)

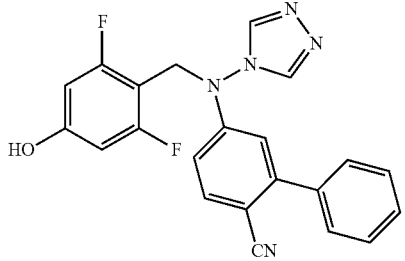 [SMILES: N#Cc1ccc(N(Cc2c(F)cc(O)cc2F)n2cnnc2)cc1-c1ccccc1]

A solution of PMW03144 (0.45 g, 2.81 mmol) in a mixture comprising of SOCl$_2$ (5 mL)/DMF (0.3 mL) was stirred for 2 h. The solvent was removed in vacuo and the resulting residue was dissolved in DMF (10 mL). 5-(4H-1,2,4-Triazol-4-ylamino)biphenyl-2-carbonitrile (CAB06022) (0.77 g, 2.95 mmol) and K$_2$CO$_3$ (1.94 g, 14.1 mmol) were added and the reaction mixture was stirred for 48 h. The mixture was poured onto H$_2$O (50 ml) and the product was extracted with EtOAc (2×50 ml). The combined organics were washed with H$_2$O (4×50 ml) and brine (50 ml), then dried (MgSO$_4$) and the solvent was removed in vacuo. The crude product was purified using the Combiflash system (DCM/acetone) to give the title compound as a white solid (0.60 g, 53%); $^1$H NMR (270 MHz, DMSO-d$_6$) 5.06 (2H, s, CH$_2$), 6.38-6.49 (2H, m, ArH), 6.71 (1H, dd, J=8.6, 2.2, ArH), 6.83 (1H, d, J=2.2, ArH), 7.48-7.61 (5H, m, ArH), 7.87 (1H, d, J=8.6, ArH), 8.75 (2H, s, NCHN), 10.58 (1H, s, OH); HRMS (ES$^+$) calcd. for C$_{22}$H$_{16}$F$_2$N$_5$O (M$^+$+1) 404.1317. found 404.1311; LC/MS (ES$^+$) t$_r$=1.40 min, m/z 404.1 (M$^+$+1, 100%).

4-(((6-Cyanobiphenyl-3-yl)(4H-1,2,4-triazol-4-yl)amino)methyl)-3,5-difluorophenyl sulfamate (PMW04153)

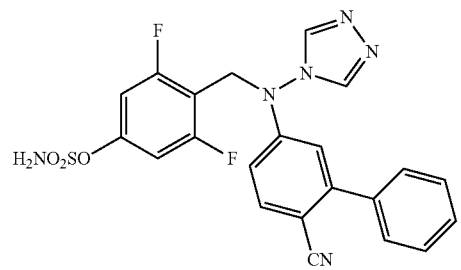

The solvent was removed from a solution of ClSO$_2$NH$_2$ in toluene (0.57 M, 6.2 ml) at 30° C. on the rotary evaporator to leave a yellow oil which solidified on cooling in an ice bath. DMA (1 mL) and a solution of PMW04146 (0.21 g, 0.52 mmol) in DMA (1 mL) were subsequently added and the reaction mixture was stirred overnight. The solution was poured onto H$_2$O (15 ml) and the product was extracted with EtOAc (2×15 ml). The organic layers were combined, washed with H$_2$O (4×15 ml) and brine (15 mL), dried (MgSO$_4$) and the solvent removed in vacuo. The crude product was purified using the Combiflash system (CHCl$_3$/Acetone) to give the title compound (0.22 g, 88%) as a white solid; $^1$H NMR (270 MHz, DMSO-d$_6$) 5.24 (2H, s, CH$_2$), 6.71 (1H, dd, J=8.8, 2.8, ArH), 6.88 (1H, d, J=2.8, AIR), 7.05-7.14 (2H, m, ArH), 7.50-7.62 (5H, m, ArH), 7.89 (1H, d, J=8.8, ArH), 8.33 (2H, s, NH$_2$), 8.82 (2H, s, NCHN); HRMS (ES$^+$) calcd. for C$_{22}$H$_{17}$F$_2$N$_6$O$_3$S (M$^+$+1) 483.1045. found 483.1031; LC/MS (ES$^+$) t$_r$=1.06 min, m/z 483.3 (M$^+$+1, 100%).

4-Fluoro-2-(furan-3-yl)benzonitrile (AUP01162-1)

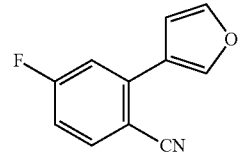 [SMILES: N#Cc1ccc(F)cc1-c1ccoc1]

Following the same procedure used for AUP01158-1, AUP01162-1 was prepared from 2-bromo-4-fluorobenzonitrile (5.0 g, 25.0 mmol), furan-3-ylboronic acid (3.36 g, 30.0), Pd$_2$(dba)$_3$ (100 mg), 1,2-dimethoxyethane (25 mL) and 2M Na$_2$CO$_3$ (40 mL). The crude was purified by Combi flash chromatography (24 g column, 8 g silica, gradient of eluent from PE to PE/EtOac 9/1) to give the title compound as a light yellow solid. This solid had to be purified an ultimate time by drying under vacuum at 60° C. for 3 days. Finally, pure expected compound was obtained as an off white solid in 32% yield (1.47 g); mp 42-68° C. (dec.); $^1$H NMR (270 MHz, CDCl$_3$) δ 6.81 (1H, d, J=2.0 Hz, ArH), 7.07 (1H, td, J=2.5 and 8.0 Hz, ArH), 7.24 (1H, dd, J=2.5 and 8.7 Hz, ArH), 7.52-7.55 (1H, m, Add), 7.72 (1H, dd, J=5.8 and 8.7 Hz, ArH), 8.06 (1H, s, ArH); HRMS (ESI) calcd. for C$_{11}$H$_7$FNO (M+H)$^+$ 188.0506. found 188.0513.

4-(4H-1,2,4-Triazol-4-ylamino)-2-(furan-3-yl)benzonitrile (AUP01172-1)

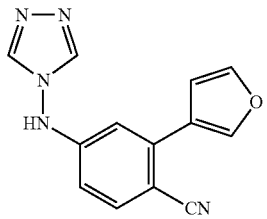 [SMILES: N#Cc1ccc(Nn2cnnc2)cc1-c1ccoc1]

Following the same procedure used for AUP01171-1, AUP01172-1 was prepared from 4H-1,2,4-triazol-4-amine (1.79 g, 21.4 mmol), KOtBu (2.40 g, 21.4 mmol), compound AUP01162-1 (2.0 g, 10.70 mmol) and DMSO (25 mL). The mixture was poured onto crushed ice and neutralized with 2M KHSO$_4$ solution (6 mL). The precipitate was filtered off, washed with water (5×20 mL) and dried (P$_2$O$_5$). The solid was washed with acetone (10 mL) and the filtrate purified by Combi flash chromatography (24 g column, 5 g silica, gradient of eluent from CH$_2$Cl$_2$ to MeOH for 25 min.) to give the title compound as a light brown solid (2.05 g, 76%); mp 199-200° C.; $^1$H NMR (270 MHz, DMSO-d$_6$) δ 6.45 (1H, dd, J=2.2 and 8.5 Hz, ArH), 6.66 (1H, d, J=2.2 Hz, ArH), 6.83-6.84 (1H, ArH), 7.75 (1H, d, J=85 Hz, ArH), 7.84 (1H, s, ArH), 8.14 (1H, s, ArH), 8.85 (2H, s, ArH), 10.24 (1H, a broad, NH); HRMS (ESI) calcd, for C$_{13}$H$_{10}$N$_5$O (M+H)$^+$ 252.0880. found 258.0872; Anal. Calcd. for C$_{13}$H$_9$N$_5$O: C, 62.15, H, 3.61, N, 27.87. Found: C, 61.90; H, 3.57; N, 27.40%.

4-((4-(Benzyloxy)benzyl)(4H-1,2,4-triazol-4-yl)amino)-2-(furan-3-yl)benzonitrile (AUP02018-1)

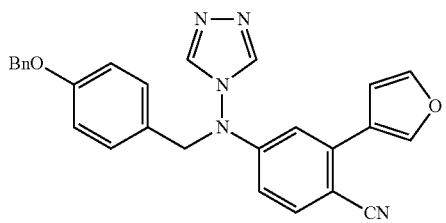 [SMILES: N#Cc1ccc(N(Cc2ccc(OCc3ccccc3)cc2)n2cnnc2)cc1-c1ccoc1]

To a solution of AUP01172-1 (502 mg, 2.0 mmol) in DMF (10 mL) was added NaH (82 mg, 2.04 mmol) at 0° C. and the mixture was stirred at r.t for 30 min. Then, 4-benzyloxybenzyl chloride (466 mg, 2.0 mmol) was added and stirring was continued for 18 h. The reaction mixture was diluted with EtOAc (0.30 mL), washed with water (3×30 mL) and brine (30 mL), dried (Na$_2$SO$_4$) and concentrated under reduced pressure. The residue was purified by Combi flash chromatography (24 g column, 5 g silica, gradient of eluent from CHCl$_3$ to CHCl$_3$/Acetone 8/2 for 25 min.) to give the title compound as a white solid after rinsing with a mixture of PE/EtOAc 2/8 (580 mg, 65%); mp 155-156° C.; $^1$H NMR (270 MHz, DMSO-d$_6$) δ 5.04 (2H, s, CH$_2$), 5.06 (2H, s, CH$_2$), 6.49 (1H, dd, J=2.8, 8.7 Hz, ArH), 6.93-6.97 (3H, m, ArH), 7.05 (1H, d, J=2.5 Hz, ArH), 7.22 (2H, d, J=8.5 Hz, ArH), 7.29-7.46 (5H, M, ArH), 7.79 (1H, d, J=8.8 Hz, ArH), 7.85-7.87 (1H, ArH), 8.21 (1H, s, ArH), 8.75 (2H, s, ArH$_{triazol}$); HRMS (ESI) calcd. for C$_{27}$H$_{22}$N$_5$O$_2$ (M+H)$^+$ 448.1768. found 448.1770; Anal. Calcd. for C$_{27}$H$_{21}$N$_5$O$_2$: C, 72.47; H, 4.73; N, 15.65. Found: C, 72.40, H, 4.73, N, 15.70%.

2-(Furan-3-yl)-4-((4-hydroxybenzyl)(4H-1,2,4-triazol-4-yl)amino)benzonitrile (AUP02023-1)

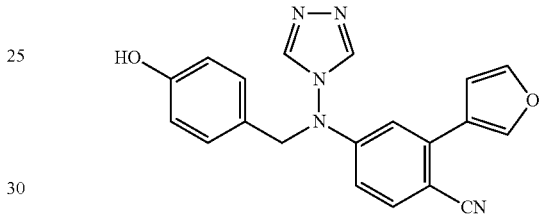

Palladium on charcoal (5%, 20 mg) was added to a solution of AUP02018-1 (510 mg, 1.14 mmol) in THF (15 mL) and MeOH (15 mL). The solution was stirred under an atmosphere of H$_2$ (provided by addition from a balloon) for 5 hours. The excess H$_2$ was removed and the reaction mixture was filtered through Celite washing with CH$_2$Cl$_2$/MeOH (8/2), then the solvent was removed in vacuo. The solid was washed with CH$_2$Cl$_2$ (5 mL) to give the title compound as a white solid (383 mg, 94%); mp 217-218° C.; $^1$H NMR (270 MHz, DMSO-d$_6$) δ 4.97 (2H, s, CH$_2$), 6.48 (1H, dd, J=2.5 and 8.5 Hz, ArH), 6.67 (2H, d, J=8.5 Hz, ArH), 6.94 (1H, d, J=1.9 Hz, ArH), 7.03-7.09 (3H, m, ArH), 7.78 (1H, d, J=8.8 Hz, ArH), 7.84-7.87 (1H, m, ArH), 8.20 (1H, s, ArH), 8.70 (2H, 5, ArH$_{triazol}$), 9.51 (1H, s broad, OH); HRMS (ESI) calcd for C$_{20}$H$_{16}$N$_5$O$_2$ (M+H)$^{30}$ 358.1299. found 358.1290; Anal. Calcd. for C$_{20}$H$_{15}$N$_5$O$_2$: C, 67.22; H, 4.23; N, 19.60. Found: C, 67.40; H, 4.25; N, 19.60%.

4-(((4-Cyano-3-(furan-3-yl)phenyl)(4H-1,2,4-triazol-4-yl)amino)methyl)phenyl sulfamate (AUP02026-1)

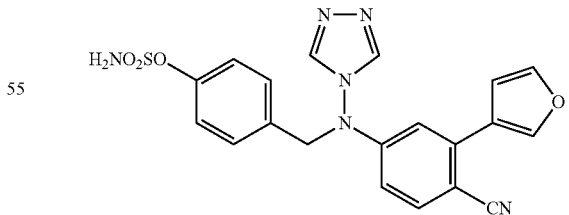

A solution of sulfamoyl chloride in toluene (0.5 M, 5.8 mL) was concentrated in vacuo at 30° C. to furnish a yellow oil which solidified upon cooling in an ice bath. DMA (1.8 mL) and AUP02023-1 (130 mg, 0.36 mmol) were subsequently added and the mixture was allowed to warm to room temperature and stirred overnight. The resulting solution was added to brine (20 mL) and the product was extracted with EtOAc (20 mL×5). The organic layers were combined, washed with brine (20 mL×3), dried (Na$_2$SO$_4$) and the solvent was removed in vacuo. The crude was purified by Combi flash chromatography (12 g column, 3 g silica, gradient of eluent from CHCl$_3$ to acetone 30 min) to give the title compound as a light yellow solid which was purified by rinsing and washing with cold CH$_2$Cl$_2$ giving the title compound as white solid (129 mg, 81%); mp 195-196° C.; $^1$H NMR (270 MHz, DMSO-d$_6$) δ 5.16 (2H, s, CH$_2$), 6.48 (1H, dd, J=2.5 and 8.8 Hz, ArH), 6.92 (1H, s, ArH), 6.99 (1H, d, J=2.5 Hz, ArH), 7.23 (2H, d, J=8.5 Hz, ArH), 7.42 (2H, d, J=8.5 Hz, ArH), 7.80 (1H, d, J=8.5 Hz, ArH), 7.84-7.86 (1H, m, ArH), 8.03 (2H, s broad, NH$_2$), 8.20 (1H, s, ArH), 8.84 (2H, s, HRMS (ESI) calcd. for C$_{20}$H$_{17}$N$_6$O$_4$S (M+H)$^+$437.1027. found 437.1018.

4-((3-Chloro-4-hydroxybenzyl)(4H-1,2,4-triazol-4-yl)amino)-2-(furan-3-yl)benzonitrile (AUP02020-1)

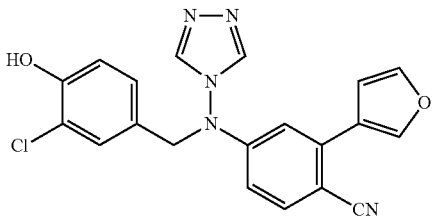 [SMILES: N#Cc1ccc(N(Cc2ccc(O)c(Cl)c2)n2cnnc2)cc1-c1ccoc1]

A solution of 2-chloro-4-(hydroxymethyl)phenol (CAB06028) (317 mg, 2.00 mmol) in SOCl$_2$ (7 mL) was stirred at r.t for 30 min. The excess SOCl$_2$ was removed under reduced pressure (rotavap) and the residue was dissolved in DMF (7 mL). Then AUP01172-1 (502 mg, 2.00 mmol) and K$_2$CO$_3$ (1.84 g, 13.37 mmol) were added and the mixture was stirred overnight. EtOAc (30 mL) and 2M KHSO$_4$ (10 mL until pH=4-5) were added, the organic layer was separated, washed with water (20 mL) and brine (30 mL), dried (Na$_2$SO$_4$) and concentrated under reduced pressure. The residue was purified twice by Combi flash chromatography (24 g column, 8 g silica, gradient of eluent from CHCl$_3$ to acetone for 40 min.) to give the title compound as a white solid after rinsing with a mixture of PE/EtOAc 2/8 (355 mg, 45%); mp 192-193° C.; $^1$H NMR (270 MHz, DMSO-d$_6$) δ 4.99 (2H, s, CH$_2$), 6.48 (1H, dd, J=2.5 and 8.8 Hz, ArH), 6.87 (1H, d, J=8.5 Hz, ArH), 6.94-7.05 (3H, m, ArH), 7.29 (1H, d, J=1.9 Hz, ArH), 7.79 (1H, d, J=8.8 Hz, ArH), 7.85-7.87 (1H, m, ArH), 8.21 (1H, s, ArH), 8.77 (2H, s, ArH$_{triazol}$), 10.34 (1H, s broad, OH); HRMS (ESI) calcd. for C$_{20}$H$_{15}$ClN$_5$O$_2$ (M+H)$^{30}$ 392.0909. found 392.0899.

2-Chloro-4-(((4-cyano-3-(furan-3-yl)phenyl)(4H-1,2,4-triazol-4-yl)amino)methyl)phenyl sulfamate (AUP02024-1)

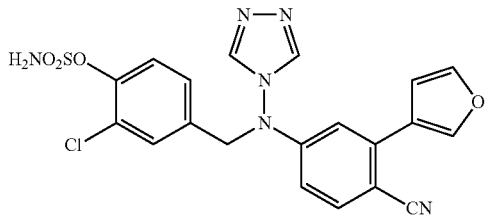

A solution of sulfamoyl chloride in toluene (0.5 M, 4.50 mL) was concentrated in vacuo at 30° C. to furnish a yellow oil which solidified upon cooling in an ice bath. DMA (12 mL) and AUP02020-1 (110 mg, 0.28 mmol) were subsequently added and the mixture was allowed to warm to room temperature and stirred overnight. The resulting solution was added to brine (20 mL) and the product was extracted with EtOAc (20 mL×5). The organic layers were combined, washed with brine (20 mL×3), dried (Na$_2$SO$_4$) and the solvent was removed in vacuo. The crude was purified by Combi flash chromatography (12 g column, 3 g silica, gradient of eluent from CHCl$_3$ to acetone 30 min) to give the title compound as a light yellow solid which was purified by rinsing and washing with cold CH$_2$Cl$_2$ giving the title compound as white solid (88 mg, 67%); mp 154-155° C.; $^1$H NMR (270 MHz, DMSO-d$_6$) δ 5.17 (2H, s, CH$_2$), 6.48 (1H, dd, J=2.8 and 8.8 Hz, ArH), 6.92 (1H, s, ArH), 6.99 (1H, d, J=2.5 Hz, ArH), 7.38-7.47 (2H, m, ArH), 7.60 (1H, s, ArH), 7.81 (1H, d, J=8.8 Hz, ArH), 7.86 (1H, 5, ArH), 8.19 (1H, s, ArH), 8.31 (2H, s broad, NH$_2$), 8.90 (2H, s, ArH$_{triazol}$); HRMS (ESI) calcd. for C$_{20}$H$_{16}$ClN$_6$O$_4$S (M+H)$^+$471.0637. found 471.0638.

4-((3-Bromo-4-hydroxybenzyl)(4H-1,2,4-triazol-4-yl)amino)-2-(furan-3-yl)benzonitrile (AUP02028-1)

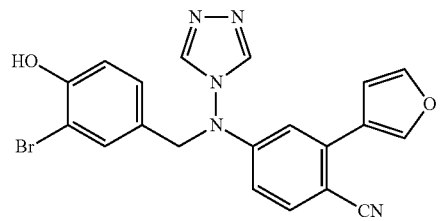 [SMILES: N#Cc1ccc(N(Cc2ccc(O)c(Br)c2)n2cnnc2)cc1-c1ccoc1]

A solution of 2-bromo-4-(hydroxymethyl)phenol (406 mg, 2.00 mmol) in SOCl$_2$ (7 mL) was stirred at r.t for 30 min. The excess SOCl$_2$ was removed under reduced pressure (vacuum pump) and the residue was dissolved in DMF (7 mL). Then AUP01172-1 (502 mg, 2.00 mmol) and K$_2$CO$_3$ (1.84 g, 13.33 mmol) were added and the mixture was stirred overnight. EtOAc (30 mL) and 2M KHSO$_4$ (10 mL until pH=4-5) were added, the organic layer was separated, washed with water (20 mL) and brine (30 mL), dried (Na$_2$SO$_4$) and concentrated under reduced pressure. The crude was purified by Combi flash chromatography (40 g column, 15 g silica, gradient of eluent from CHCl$_3$ to acetone for 30 min.) to give the title compound as a light orange solid (AUP02028-1:340 mg after rinsing with cold DCM, 39%) and starting material as a orange solid (AUP02028-2: 220 mg, 44%); mp 200-201° C.; $^1$H NMR (270 MHz, DMSO-d$_6$) δ 4.99 (2H, s, CH$_2$), 6.48 (1H, dd, J=2.5 and 8.8 Hz, ArH), 6.86 (1H, d, J=8.3 Hz, ArH), 6.94 (1H, s, ArH), 7.04-7.10 (2H, m, ArH), 7.43 (1H, s, ArH), 7.79 (1H, d, J=8.5 Hz, ArH), 7.86 (1H, s, ArH), 8.21 (1H, s, ArH), 8.76 (2H, s, ArH$_{triazol}$), 10.37 (1H, a broad, OH); HRMS (ESI) calcd. for C$_{20}$H$_{15}$BrN$_5$O$_2$ (M+H)$^+$436.0404. found 436.0398.

2-Bromo-4-(((4-cyano-3-(furan-3-yl)phenyl)(4H-1,2,4-triazol-4-yl)amino)methyl)phenyl sulfamate (AUP02030-1)

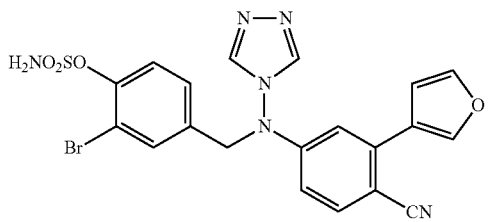

A solution of sulfamoyl chloride in toluene (0.5 M, 5.1 mL) was concentrated in vacuo at 30° C. to furnish a yellow oil which solidified upon cooling in an ice bath. DMA (1.5 mL) and AUP02028-1 (140 mg, 0.32 mmol) were subsequently added and the mixture was allowed to warm to room temperature and stirred overnight. The resulting solution was added to brine (20 mL) and the product was extracted with EtOAc (20 mL×5). The organic layers were combined, washed with brine (20 mL×3), dried ($Na_2SO_4$) and the solvent was removed in vacuo. The crude was purified by Combi flash chromatography (12 g column, 3 g silica, gradient of eluent from $CHCl_3$ to acetone 30 min) to give the title compound as a light yellow solid which was purified by rinsing and washing with cold $CH_2Cl_2$ giving the title compound as white solid (114 mg, 69%); nap 167-177° C. decamp; $^1$H NMR (270 MHz, DMSO-$d_6$) δ 5.17 (2H, s, $CH_2$), 6.47 (1H, dd, J=2.5 and 8.8 Hz, ArH), 6.92 (1H, s, ArH), 6.99 (1H, d, J=2.5 Hz, ArH), 7.44 (2H, s, ArH), 7.74 (1H, s, ArH), 7.81 (1H, d, J=8.8 Hz, ArH), 7.86 (1H, s, ArH), 8.19 (1H, s, ArH), 8.32 (2H, s broad, $NH_2$), 8.89 (2H, 5, ArH$_{triazol}$); HRMS (ESI) calcd. for $C_{20}H_{16}BrN_6O_4S$ (M+H)$^+$ 515.0132. found 515.0139; HPLC (90% $CH_3CN$ in $H_2O$) $t_r$=1.33 min (100%); Anal. Calcd. for $C_{20}H_{15}BrN_6O_4S$: C, 46.61, H, 2.93, N, 16.31. Found: C, 47.00, H, 3.10, N, 16.00%.

2-(2,6-Difluoro-4-methoxyphenyl)malonic acid (PMW04138)

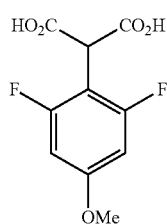

3M aq. NaOH (80 mL) was added to a solution of diethyl 2-(2,6-difluoro-4-methoxyphenyl)malonate, 6.30 g, 20.85 mmol) in $Et_2O$ (5 mL). The reaction mixture was heated at reflux until all the solid had dissolved. After cooling, the mixture was acidified with 3M aq. HCl and the product was extracted with EtOAc (2×100 ml). The combined organic layers were dried ($MgSO_4$) and solvent was removed in vacuo to give the title compound as a tan coloured solid (4.50 g, 88%); mp 157° C. (dec); $^1$H NMR (270 MHz, DMSO-$d_6$) 3.78 (3H, s, $CH_3$), 4.72 (1H, s, CH), 6.70-6.79 (2H, m, ArH).

2-(2,6-Difluoro-4-methoxyphenyl)acetic acid (PMW04140)

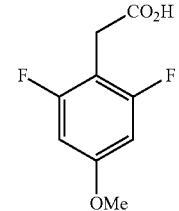 [SMILES: COc1cc(F)c(CC(=O)O)c(F)c1]

PMW04138 (4.49 g, 18.3 mmol) was heated at 160° C. until melting was complete and fizzing had ceased. Following cooling, the product was recrystallised from PE/EtOAC to give the title compound as a white crystalline solid (3.43 g, 93%); mp 137-139° C.; $^1$H NMR (270 MHz, DMSO-$d_6$) 3.52 (2H, s, $CH_2$), 3.77 (3H, s, $CH_3$), 6.68-6.79 (2H, m, ArH); HRMS (ES+) calcd for $C_9H_9F_2O_2$ 203.0514. found 203.0508.

Methyl 2-(2,6-difluoro-4-methoxyphenyl)acetate (PMW94141)

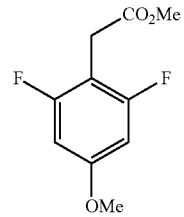

A solution of PMW04140 (3.37 g, 16.7 mmol) in MeOH (70 mL) containing conc. HCl (15 drops) was heated at reflux overnight. The mixture was allowed to cool and was neutralised with sat aq. $NaHCO_3$. The solvent was removed in vacuo and the residue was dissolved in EtOAc (100 mL) and washed with $H_2O$ (100 mL), sat. aq, $NaHCO_3$ (100 mL) and brine (100 mL) then dried ($MgSO_4$) and the solvent was removed in vacuo. The title compound (3.30 g, 92%) was obtained as a pale yellow oil; $^1$H NMR. (270 MHz, DMSO-$d_6$) 3.61 (2H, s, $CH_2$), 3.69 (3H, s, $CH_3$), 3.76 (3H, s, $CH_3$), 6.40-6.49 (2H, m, ArH); $^{19}$F NMR (376.4 MHz, DMSO-$d_6$)-114.4 (d); HRMS (ES+) calcd, for $C_{10}H_{11}F_2O_3$ (M$^+$+H) 217.0657. found 217.0663; LC/MS (ES$^+$) $t_r$=1.69 min, m/z 216.8 (M$^+$, 100%).

Methyl 2-(2,6-difluoro-4-hydroxyphenyl)acetate (PMW04148)

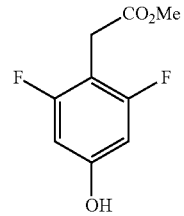

$BBr_3$ (1M in DCM, 55 mL, 55 mmol) was added to a cooled (-78° C.) solution of PMW04141 (2.87 g, 13.3 mmol) in DCM (25 mL). The reaction mixture was stirred at -78° C. for 10 min, then allowed to warm to room temperature and stirred for 3 h 30. The reaction was quenched with sat. $NaHCO_3$ (aq.)

and the product was extracted with DCM (2×150 mL). The combined organic layers were washed with brine (150 mL), dried (MgSO$_4$) and the solvent was removed in vacuo. The crude product was purified using the Combiflash system (PE/EtOAc) to give the title compound (2.07 g, 77%) as a white crystalline solid; mp 75.5-77.5° C.; $^1$H NMR (270 MHz, DMSO-d$_6$) 3.58 (2H, s, CH$_2$), 3.61 (3H, s, CH$_3$), 6.41-6.51 (2H, m, ArH), 10.34 (1H, s, OH); $^{19}$F NMR (376.4 MHz, DMSO-d$_6$)-115.4 (d); HRMS (ES+) calcd. for C$_9$H$_9$F$_2$O$_3$ (M$^+$+H) 203.0514. found 203.0511; LC/MS (ES$^+$) t$_r$=1.45 min, m/z 2018 (M$^+$+H, 100%).

Methyl 2-(2,6-difluoro-4-(triisopropylsilyloxy)phenyl)acetate (PMW04151)

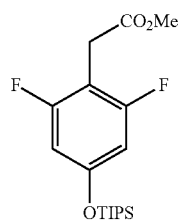

Imidazole (1.43 g, 21.0 mmol) and TIPS—Cl (2.24 g, 11.6 mmol) were sequentially added to a pale yellow solution of PMW041448 (2.13 g, 10.5 mmol) in DMF (10 mL). The reaction mixture was stirred overnight, then poured onto H$_2$O (40 ml) and extracted with EtOAc (3×50 ml). The combined organics were washed with H$_2$O (3×100 ml) and brine (100 ml), then dried (MgSO$_4$) and the solvent was removed in vacuo. The crude product was purified using the Combiflash system (PE/EtOAc) to give the title compound as a colourless oil (3.43 g, 91%); $^1$H NMR (270 MHz, CDCl$_3$) δ 1.04-1.32 (21H, m, 6×CH$_3$, 3×CH), 3.60 (2H, s, CH$_2$), 3.69 (3H, s, CH$_3$), 6.36-6.48 (2H, m, ArH); $^{13}$C NMR (100 MHz, DMSO-d$_6$) 12.5 (3×CH), 17.8 (6×CH$_3$), 27.4 (CH$_2$), 52.2 (CH$_3$), 103.3 (C, t), 103.4 (2×CH, dd), 156.7 (C, t), 161.6 (2×C, dd), 170.6 (C); $^{19}$F NMR (376 MHz, DMSO-d$_6$)-117.9 (d), 2-(2,6-Difluoro-4-(triisopropylsilyloxy)phenyl)ethanol (PMW04155)

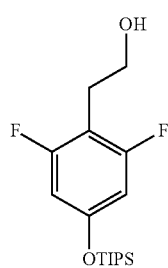

A solution of PMW04151 (2.98 g, 8.30 mmol) in THF (15 mL) was added to a cooled (0° C.) suspension of LiAlH$_4$ (0.79 g, 20.8 mol) in THF (50 mL). After stirring for 15 minutes, the reaction was quenched by addition of EtOAc (25 mL), H$_2$O (25 mL) and 3M HCl (25 mL). The product was extracted with EtOAc (2×75 ml) and the combined organics were washed with sat. aq. NaHCO$_3$ (2×100 mL) dried (MgSO$_4$) and the solvent was removed in vacuo. The crude product was purified using the Combiflash system (EtOAc/PE) to give the title compound (1.70 g, 62%) as a colourless oil; $^1$H NMR (270 MHz, CDCl$_3$) δ 1.02-1.31 (21H, m, 6×CH$_3$, 3×CH), 1.61 (1H, s, OH), 2.85 (2H, t, J=6.9, CH$_2$), 3.36 (2H, t, CH$_2$), 6.34-6.48 (2H, m, ArH); $^{19}$F NMR (376 MHz, DMSO-d$_6$)-116.0 (d); HRMS (ES$^+$) calcd. for C$_{17}$H$_{29}$F$_2$O$_2$Si (M$^+$+1) 331.1899. found 331.1887; LC/MS (ES$^+$) t$_r$=2.23 min, adz 353.4 (M$^+$+Na, 100%), 331.3 (M$^+$+1, 80).

(4-(2-Bromoethyl)-3,5-difluorophenoxy)triisopropylsilane (PMW04158)

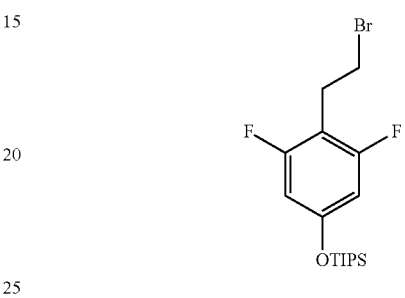

PPh$_3$ (1.11 g, 4.24 mmol) was added to a cooled (0° C.) solution of CBr$_4$ (0.92 g, 237 mmol) in DCM (15 mL). After stirring for 15 minutes, a solution of PMW04155 (0.70 g, 2.12 mmol) in DCM (5 mL) was added and the reaction mixture was stirred for 1 h, then allowed to warm to room temperature and stirred for 2 h. The solvent was removed in vacuo and the residue was purified using the Combiflash system (EtOAc/PE) to give the title compound (0.56 g, 67%) as a colourless oil; $^1$H NMR (270 MHz, CDCl$_3$) 1.05-1.32 (21H, m, 6×CH$_3$, 3×CH), 3.13 (2H, t, J=7.7, CH$_2$), 3.48 (2H, t, J=7.7, CH$_2$), 6.34-6.45 (2H, m, ArH).

5-((2,6-Difluoro-4-hydroxyphenethyl)(4H-1,2,4-triazol-4-yl)amino)biphenyl-2-carbonitrile (PMW04165)

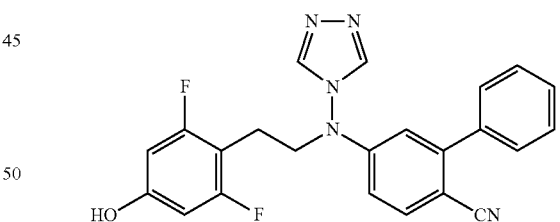

NaH (60% dispersion in mineral oil, 0.039 g, 0.98 mmol) was added to a solution of 5-(4H-1,2,4-triazol-4-ylamino) biphenyl-2-carbonitrile (CAB06022) (0.23 g, 0.88 mmol) in DMF (5 mL). After stirring for 30 minutes a solution of PMW04158 (0.38 g, 0.97 mmol) in DMF (3 mL) was added and stirring was continued for 48 h. TBAF (1M in THF, 1.35 mL) was added and after 30 minutes the reaction mixture was poured onto H$_2$O (15 mL) and acidified with 3M aq. AcOH. The product was extracted with EtOAc (0.3×25 ml) and the combined organics were washed with H$_2$O (4×50 ml) and brine (50 mL) then dried (MgSO$_4$) and the solvent was removed in vacuo. The crude product was purified using the Combiflash system (CHCl$_3$/Acetone) to give the title compound (0.18 g, 50%) as a white solid; $^1$H NMR (270 MHz, DMSO-d$_6$) 2.81 (2H, t, J=7.5, CH$_2$), 4.01 (2H, t, J=7.5, CH$_2$), 6.41-6.51 m, ArH), 6.61 (1H, d, J=2.2, ArH), 7.45-7.56 (5H, m, ArH), 7.83 (1H, d, J=8.8, ArH), 8.93 (2H, s, NCHN), 10.40 (1H, s, OH); HRMS (ES$^S$) calcd. for C$_{13}$H$_{18}$F$_2$N$_5$O$_1$ (M$^+$+1) 418.1474. found 418.1466; LC/MS (ES$^+$) t$_r$=1.39 min, m/z 418.0 (M$^+$+1, 100%).

4-(2-((6-Cyanobiphenyl-3-yl)(4H-1,2,4-triazol-4-yl)amino)ethyl)-3,5-difluorophenyl sulfamate (PMW04169)

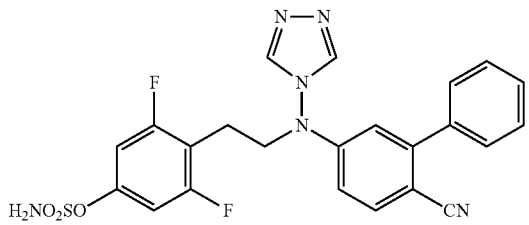

The solvent was removed from a solution of ClSO$_2$NH$_2$ in toluene (0.45 M, 3.0 ml) at 30° C. on the rotary evaporator to leave a yellow oil which solidified on cooling in an ice bath. DMA (1 mL) and a solution of PMW04165 (0.10 g, 0.24 mmol) in DMA (1 mL) were subsequently added and the reaction mixture was stirred overnight. The solution was poured onto H$_2$O (15 ml) and the product was extracted with EtOAc (2×15 ml). The organic layers were combined, washed with H$_2$O (4×15 ml) and brine (15 mL), dried (MgSO$_4$) and the solvent removed in vacuo. The crude product was purified using the Combiflash system (CHCl$_3$/Acetone) to give the title compound (0.072 g, 61%) as a white solid; $^1$H NMR (270 MHz, DMSO-d$_6$) 2.94 (2H, t, J=7.4, CH$_2$), 4.10 (2H, t, J=7.4, CH$_2$), 6.51 (1H, dd, J=8.8, 2.5, ArH), 6.68 (1H, d, J=2.5, ArH), 7.05-7.13 (2H, m, ArH), 7.46-7.56 (5H, m, ArH), 7.85 (1H, d, J=8.8, ArH), 8.25 (2H, s, NH$_2$), 8.98 (2H, s, NCHN); HRMS (ES$^+$) calcd, for C$_{23}$H$_{19}$F$_2$N$_6$O$_3$S (M$^+$+1) 497.1202. found 497.1200; LC/MS (ES$^+$) t$_r$=1.31 min, m/z 497.3 (M$^+$+1, 100%).

5-Fluoro-4'-(trifluoromethyl)biphenyl-2-carbonitrile (CAB06081)

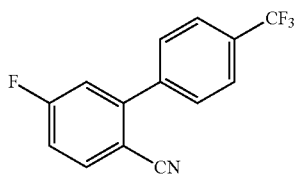 [SMILES: N#Cc1ccc(F)cc1-c1ccc(C(F)(F)F)cc1]

A mixture of 2-bromo-4-fluorobenzinitrile (4.0 g, 20.0 mmol), 4-(trifluoromethyl)phenylboronic acid (4.178 g, 22.0 mmol), dimethoxyethane (30 mL) and 2M Na$_2$CO$_3$ (40 mL) was heated to reflux before Pd$_2$(dba)$_3$ (0.10 g) was added and heating was continued for 5 h. After cooling to room temperature CHCl$_3$ (50 mL) was added to and the mixture was filtered (celite). The organic layer was separated, dried (Na$_2$SO$_4$) and concentrated under reduced pressure. The residue was purified by flash chromatography [SiO$_2$, CHCl$_3$] followed by recrystallisation from CHCl$_3$/n-hexane to give CAB06081 (4.03 g, 71%) as colorless needles. Mp. 106-107° C.; $^1$H NMR (400 MHz, DMSO-d$_6$) δ 7.53 (dt, J=8.6, 2.7 Hz, 1H), 7.62 (dd, J=9.8, 27 Hz, 1H), 7.84 (d, J=8.2 Hz, 2H), 7.91 (d, J=8.2 Hz, 2H), 8.11 (dd, J=8.6, 5.5 Hz, 1H); LRMS (ES+): m/z 266.1 (100%, [M+H]$^4$); HRMS (ES+) calcd for C$_{14}$H$_8$F$_4$N [M+H]$^+$: 266.0587. found 266.0577; Anal, Calcd for C$_{14}$H$_8$F$_4$N: C, 63.40; H, 2.66; N, 5.28. Found C, 63.5; H, 2.66; N, 5.28.

5-(4H-1,2,4-Triazol-4-ylamino)-4'-(trifluoromethyl)biphenyl-2-carbonitrile (CAB06082)

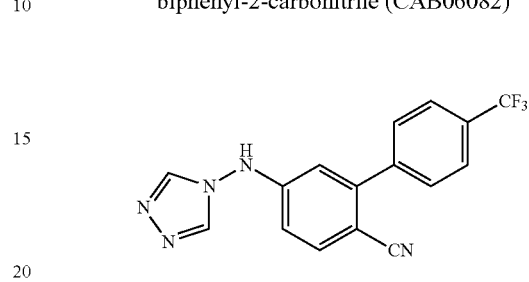

To a solution of 4H-1,2,4-triazol-4-amine (1.332 g, 15.84 mmol) in DMSO (30 mL) was added KOtBu (1.778 g, 15.84 mmol). The mixture was stirred for 0.5 h at room temperature before CAB06081 (2.10 g, 7.92 mmol) was added and stirring was continued for 1 h. The mixture was poured into crushed ice and neutralized with 2M KHSO$_4$ solution. The precipitate was filtered off, washed with water and recrystallised from EtOAc/n-hexane to give CAB06082 (1.80 g, 69%) as a white crystalline solid, Mp. 140-143° C.; $^1$H NMR (400 MHz, DMSO-d$_6$) δ 6.59 (d, J=2.4 Hz, 1H), 6.64 (dd, J=8.6, 2.4 Hz, 1H), 7.72 (AA'BB', 2H), 7.85 (d, J=8.6 Hz, 1H), 7.89 (AA'BB', 2H), 8.87 (s, 2H), 10.39 (s, 1H); LRMS (ES+): m/z 329.1 (100%, [M+H]$^+$); HRMS (ES+) calcd for C$_{16}$H$_{10}$F$_3$N$_5$ [M+H]$^+$: 330.0961. found 330.0950

5-((4-(Benzyloxy)benzyl)(4H-1,2,4-triazol-4-yl)amino)-4'-(trifluoromethyl)-biphenyl-2-carbonitrile (CAB06097)

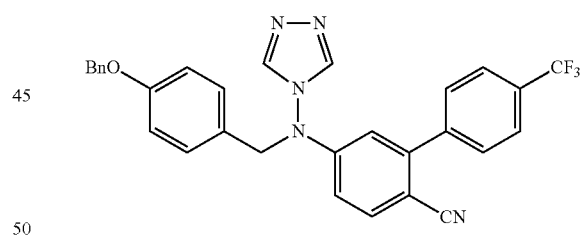

To a solution of CAB06082 (0.660 g, 2.0 mmol) in DMF (10 mL) was added NaH (0.0.80 g, 2.0 mmol, 60% in mineral oil) at room temperature. The mixture was stirred for 0.5 h before benzyloxybenzyl chloride (0.465 g, 3.0 mmol) was added and stirring was continued for 18 h. The reaction mixture was diluted with EtOAc (50 mL), washed with water (3×30 mL) and brine (30 mL), dried (Na$_2$SO$_4$) and concentrated under reduced pressure. The residue was purified by flash chromatography [SiO$_2$, EtOAc (neat)] to give CAB06097 (0.798 g, 76%) as a white solid, Mp. 173-175° C.; $^1$H NMR (400 MHz, DMSO-d$_6$) δ 5.06 (s, 4H), 6.73 (dd, J=8.2 Hz, 2.7 Hz, 1H), 6.92 (d, J=2.7 Hz, 1H), 6.96 (AA'BB', 2H), 7.21 (AA'BB', 2H), 7.30-7.45 (m, 5H), 7.76 (AA'BB', 2H), 7.89 (d, J=8.2 Hz, 1H), 7.92 (AA'BB', 2H), 8.75 (s, 2H); LRMS (ES+): m/z 526.2 (100%, [M+H]$^+$); HRMS (ES+) calcd for C$_{30}$H$_{23}$F$_3$N$_5$O [M+H]$^+$: 526.1849 found 526.1835;

5-((4-Hydroxybenzyl)(4H-1,2,4-triazol-4-yl)amino)-4'-(trifluoromethyl)-biphenyl-2-carbonitrile (CAB06100)

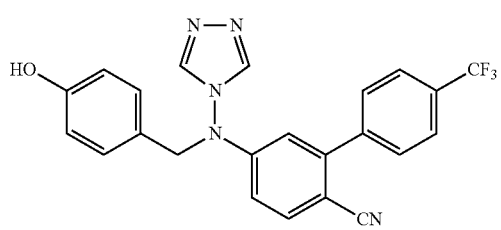 [SMILES: N#Cc1ccc(N(Cc2ccc(O)cc2)n2cnnc2)cc1-c1ccc(C(F)(F)F)cc1]

To a solution of CAB06097 (0.585 g, 1.10 mmol) in THF (20 mL) and methanol (20 mL) was added Pd—C (0.10 g, 5% Pd). The mixture was stirred under $H_2$-atmosphere for 18 h before the catalyst was filtered off (celite) and the volatiles were removed under reduced pressure. The residue was recrystallized from EtOAc give CAB06100 (0.410 g, 85%) as fine colorless needles. Mp, >215° C. (dec.); $^1$H NMR (400 MHz, DMSO-$d_6$) δ 4.99 (s, 2H), 6.67 (AA'BB', 2H), 6.73 (dd, J=8.6, 2.3 Hz, 1H), 6.82 (d, J=2.3 Hz, 1H), 7.06 (AA'BB', 2H), 7.76 (d, J=8.6 Hz, 1H), 7.91 (d, J=8.2 Hz, 2H), 8.71 (s, 2H), 9.49 s, 1H); LRMS (ES+): m/z 436.0 (100%, [M+H]$^+$); HRMS (ES+) calcd for $C_{23}H_{16}F_3N_5O$ [M+H]$^+$: 436.1380 found 436.1371; Anal. Calcd for $C_{23}H_{16}F_3N_5O$: C, 63.45; H, 3.70; N, 16.08. Found C, 63.2; H, 3.66; N, 15.8.

4-(((6-Cyano-4'-(trifluoromethyl)biphenyl-3-yl)(4H-1,2,4-triazol-4-yl)amino)-methyl)phenyl sulfamate (CAB06102)

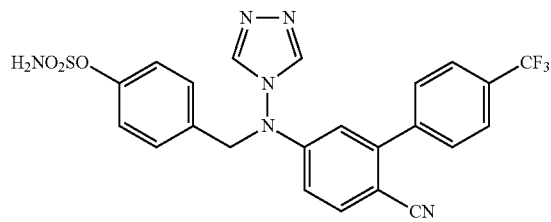

To a solution of sulfamoyl chloride (0.399 g, 3.45 mmol) in DMA (1 mL) was added a solution of CAB06100 (0.103 g, 0.237 mmol) in DMA (5 mL) at 0° C. The clear solution was stirred for 2 h at 0° C. and then for 4 h at room temperature. EtOAc (50 mL) and water (20 mL) were added, the organic layer was separated, washed with water (2×30 mL) and brine (0.30 mL), dried ($Na_2SO_4$) and concentrated under reduced pressure. The residue was crystallised from ethyl acetate to afford CAB06102 (0.107 g, 88%) as a white solid. Mp. 177-180° C.; $^1$H NMR (400 MHz, DMSO-$d_6$) δ 5.18 (s, 2H), 6.70 (dd, J=8.6, 2.4 Hz, 1H), 6.89 (d, J=2.4 Hz, 1H), 7.23 (AA'BB', 2H), 7.41 (AA'BB, 2H), 7.64 (AA'BB', 2H) 7.88-7.94 (m, 2H), 8.02 (s, 2H), 8.84 (s, 2H); LRMS (ES+): m/z 515.2 (60%, [M+H]$^+$), 446.2 (100%); HRMS (ES+) calcd for $C_{23}H_{18}F_3N_6O_3S$ [M+H]$^+$: 515.1108 found 515.1098.

Anal. Calcd for $C_{30}H_{22}F_3N_5O$: C, 68.56; H, 4.22; N, 18.33. Found C, 68.3; H, 4.23; N, 18.3.

The compounds below have also been prepared in accordance with the general synthetic schemes given above and in accordance with the examples of compounds of the present invention described above Compound 1

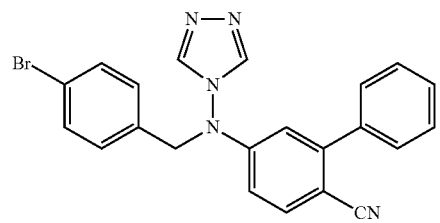

molecular weight (MW) 430 31, colorless crystal, Melting point (Mp) = 185-186° C.

Compound 2

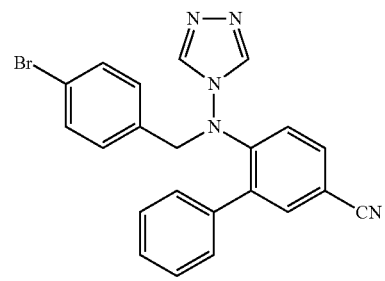

MW 430 31, Mp = 195-197° C.

Compound 3

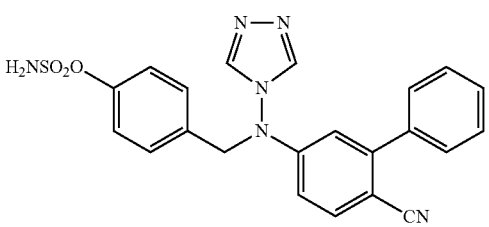

MW 446, 49, Mp 209-211° C.

Compound 4

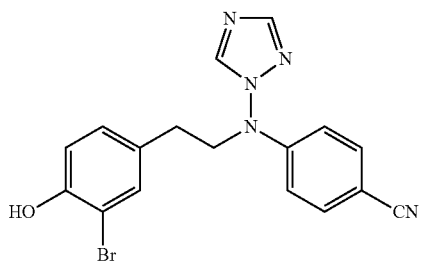

MW 383 25

Compound 5

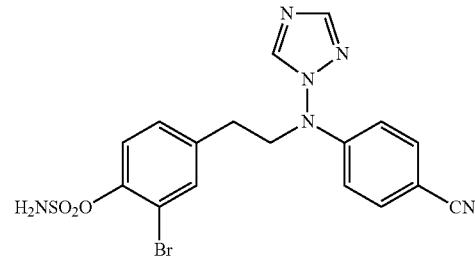

MW 462 33

Compound 6
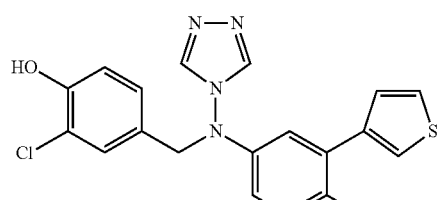
MW 407.88, white solid
Compound 7
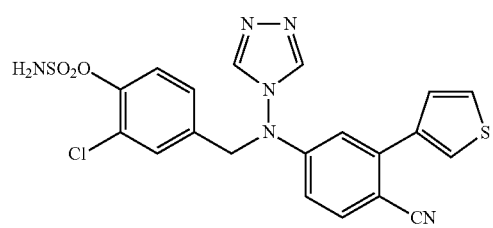
MW 486.96, white solid
Compound 8
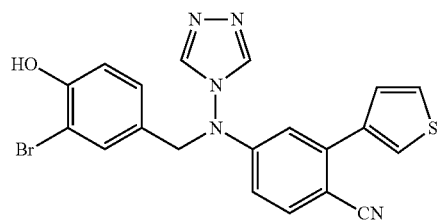
MW 452.33, Light orange solid
Compound 9
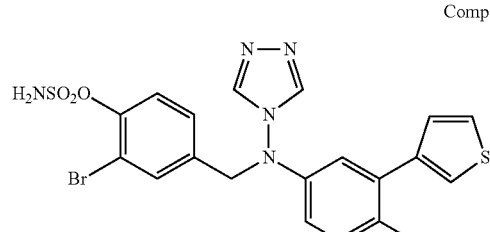
MW 531.41, white solid
Compound 10
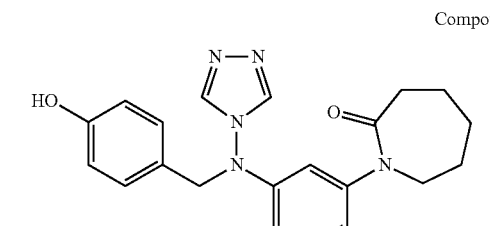
MW 481.53, White solid
Compound 11
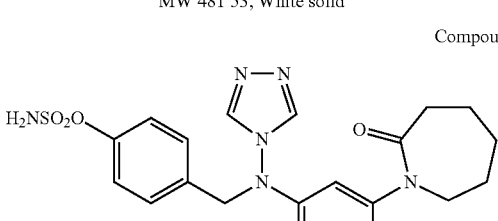
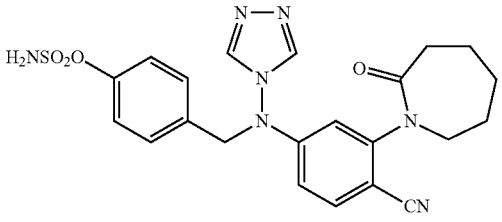
MW 481.53
Compound 12
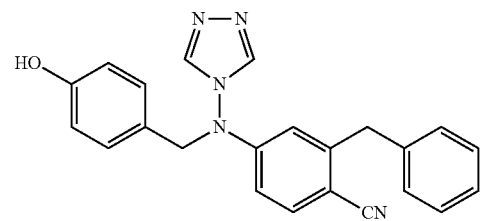
MW 381.44, White solid
Compound 13
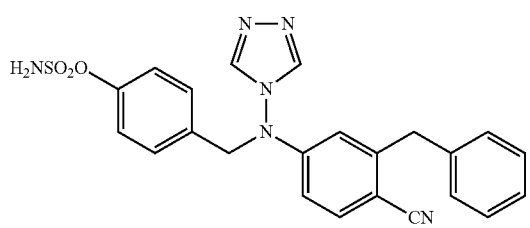
MW 460.52, White solid
Compound 14
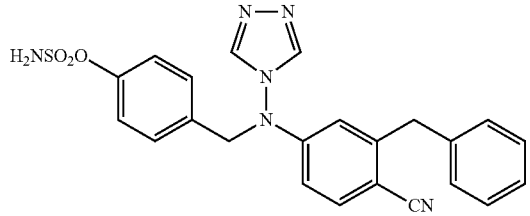
MW 360.42, White solid
Compound 15
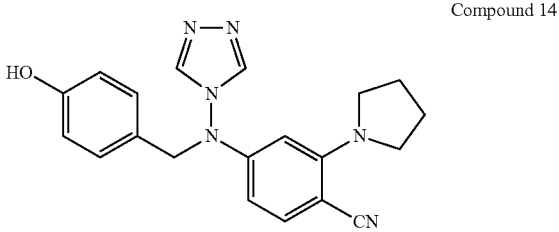
MW 439.5, off white solid
Compound 16
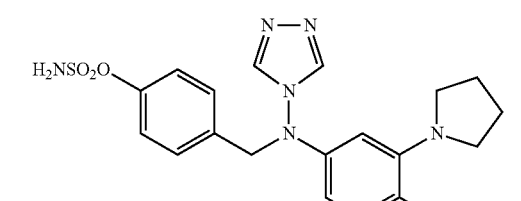
MW 374.45, off white solid
Compound 17
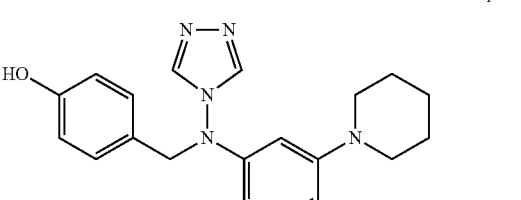
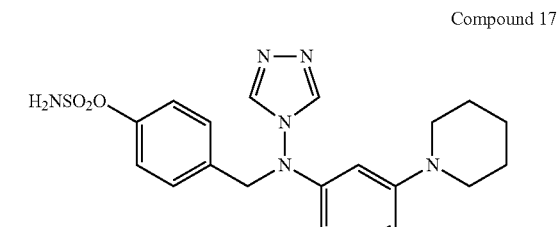
MW 453.52, Off white solid Compound 18
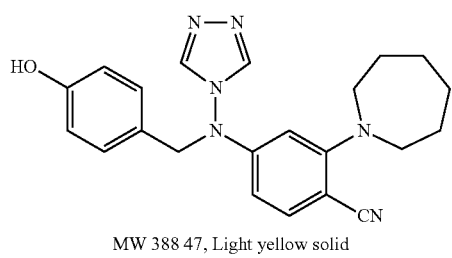
MW 388 47, Light yellow solid
Compound 19
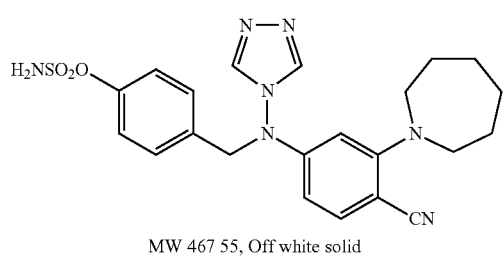
MW 467 55, Off white solid
Compound 20
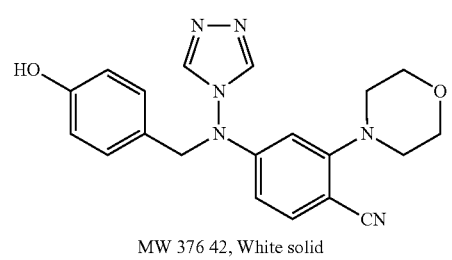
MW 376 42, White solid
Compound 21
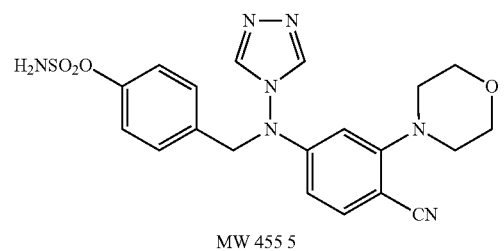
MW 455 5
Compound 22
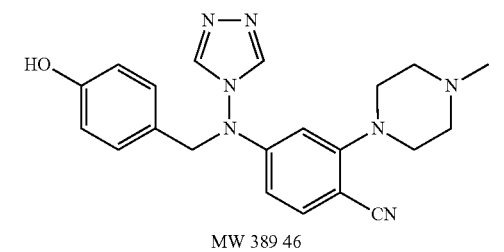
MW 389 46
Compound 23
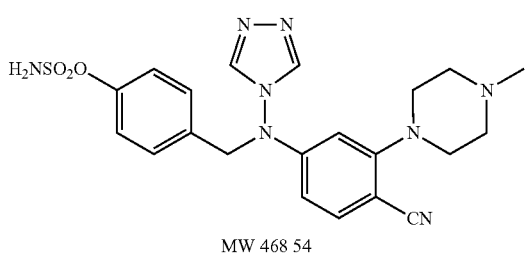
MW 468 54
Compound 24
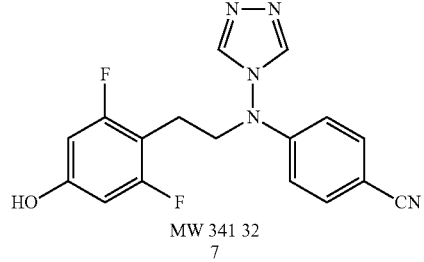
MW 341 32
Compound 25
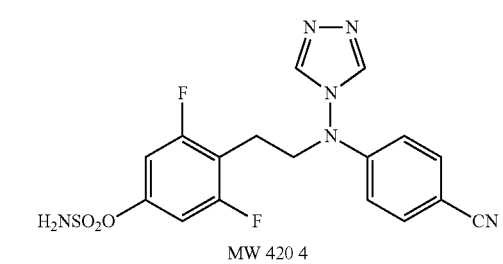
MW 420 4
Compound 26
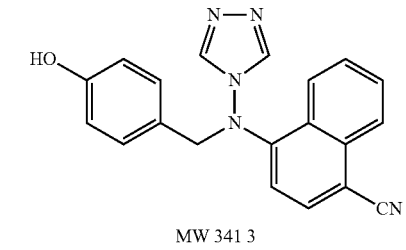
MW 341 3
Compound 27
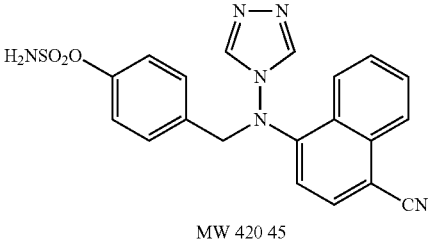
MW 420 45
Compound 28
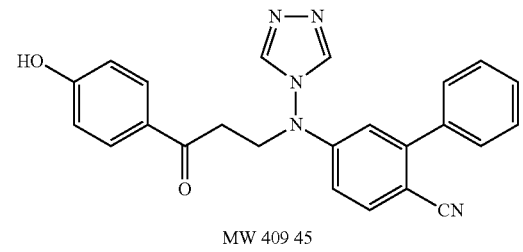
MW 409 45
Compound 29
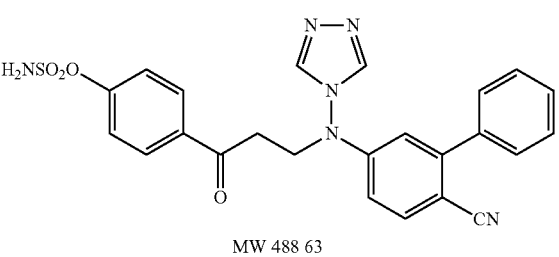
MW 488 63

-continued
Compound 30
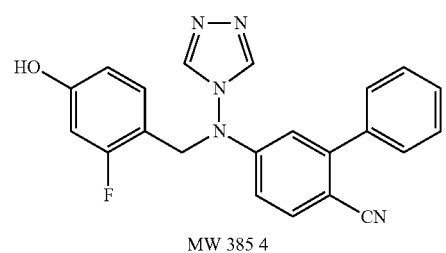
MW 385 4
Compound 31
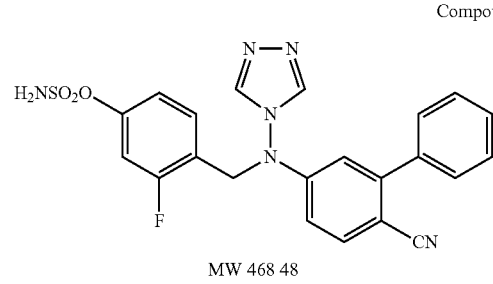
MW 468 48
Compound 32
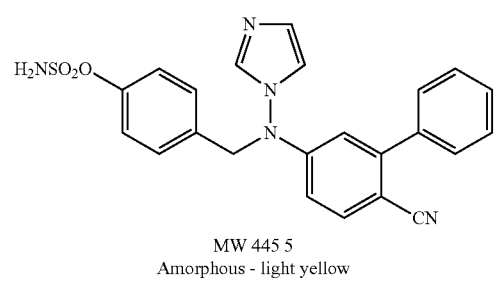
MW 445 5
Amorphous - light yellow
Compound 33
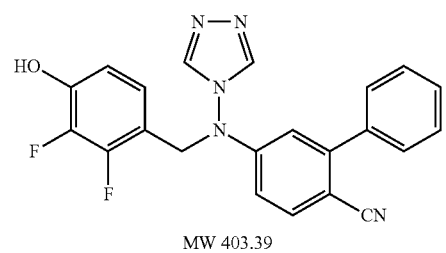
MW 403.39
Compound 34
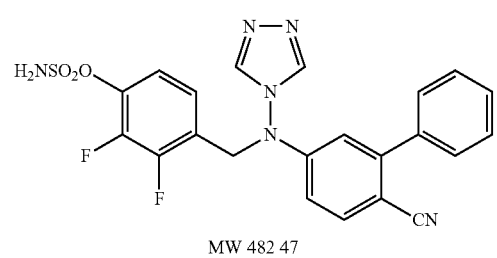
MW 482 47
-continued
Compound 35
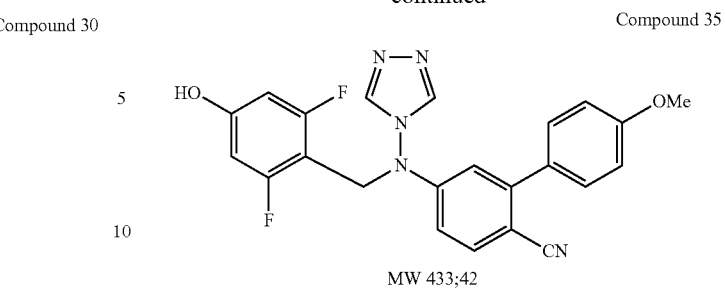
MW 433;42
Compound 36
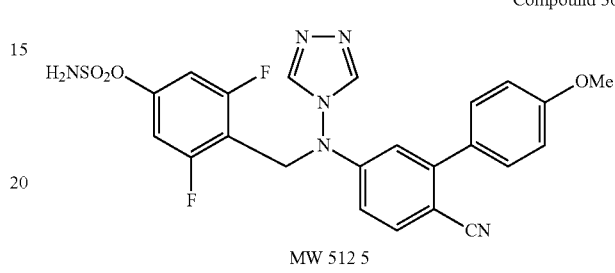
MW 512 5
Compound 37
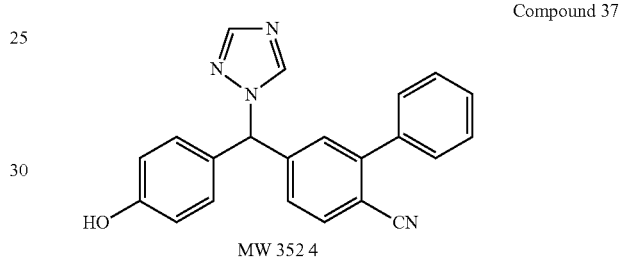
MW 352 4
Compound 38
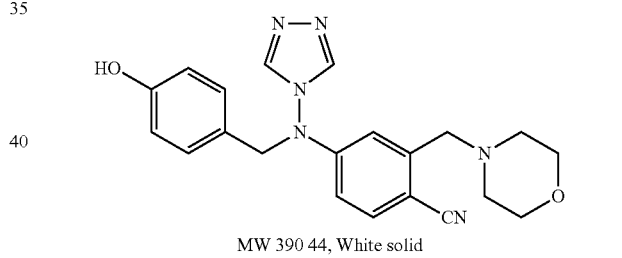
MW 390 44, White solid
Compound 39
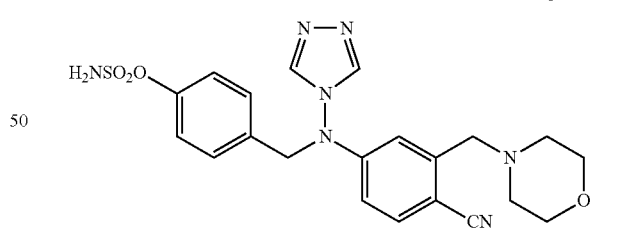
MW 469 52, White solid
Compound 40
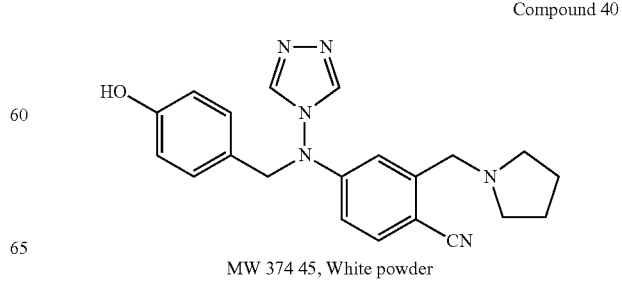
MW 374 45, White powder Compound 41
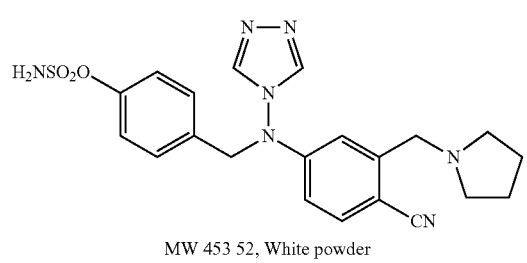
MW 453 52, White powder
Compound 42
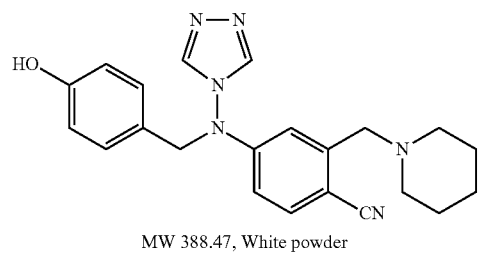
MW 388.47, White powder
Compound 43
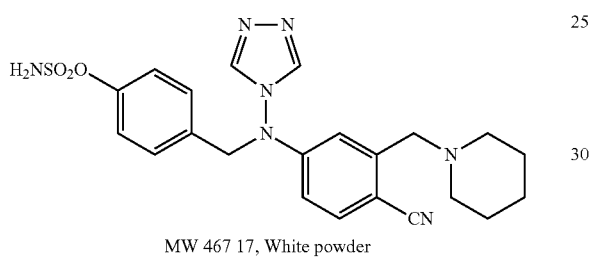
MW 467 17, White powder
Compound 44
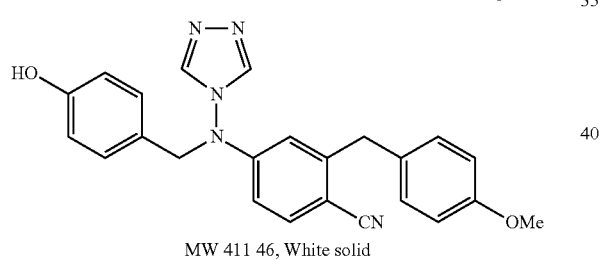
MW 411 46, White solid
Compound 45
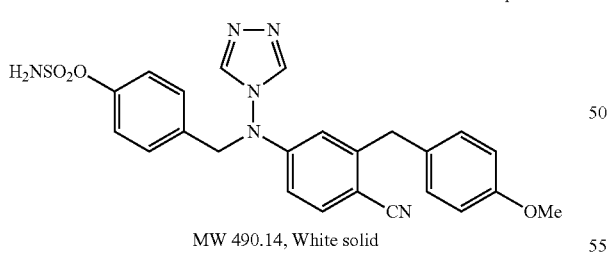
MW 490.14, White solid
Compound 46
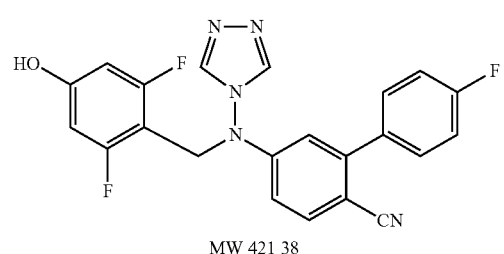
MW 421 38
Compound 47
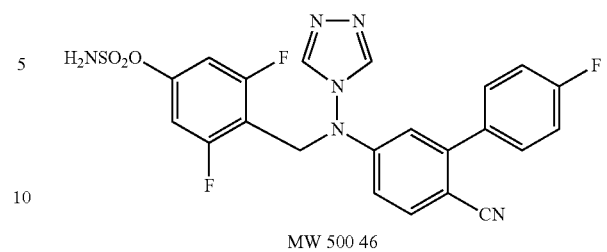
MW 500 46
Compound 48
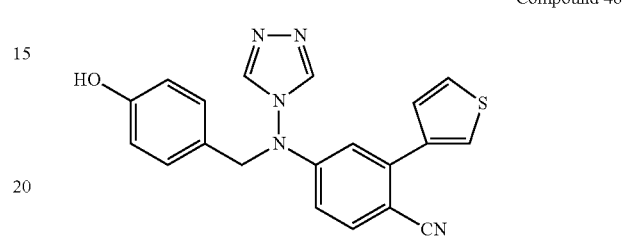
Compound 49
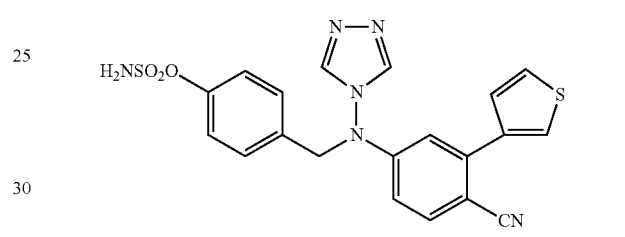
Compound 50
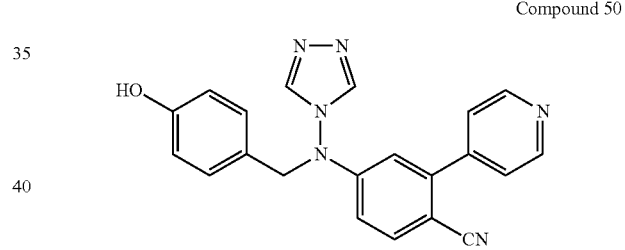
Compound 51
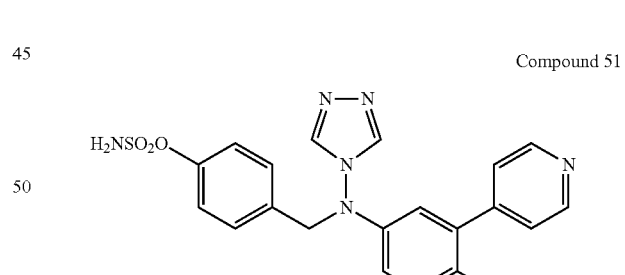
Compound 52
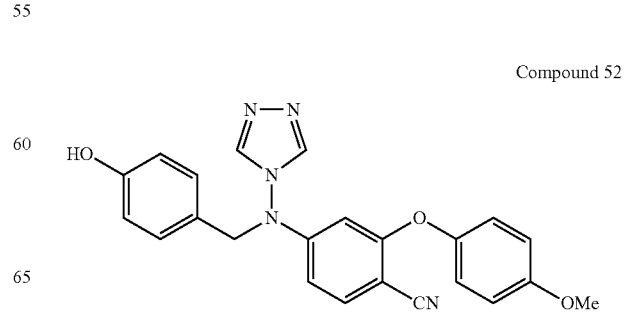

Compound 53
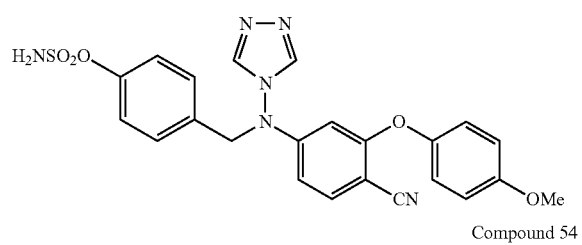
Compound 54
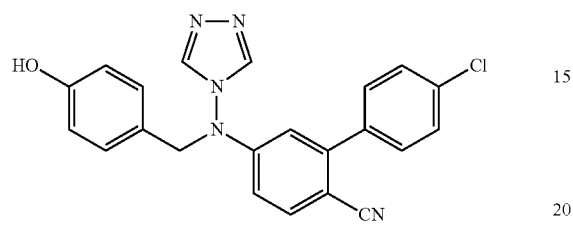
Compound 55
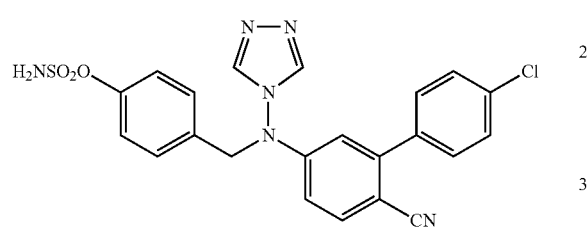
Compound 56
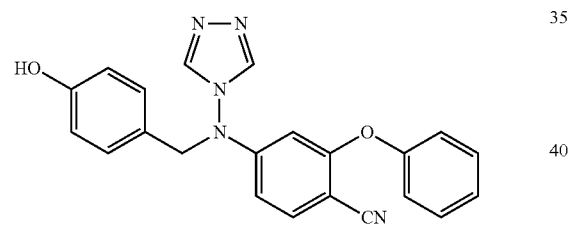
Compound 57
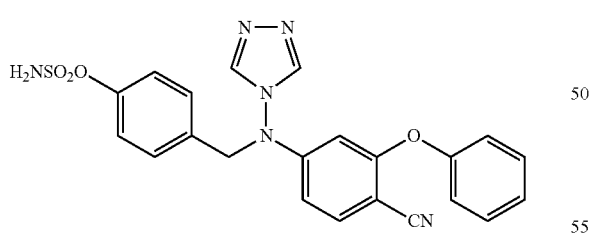
Compound 58
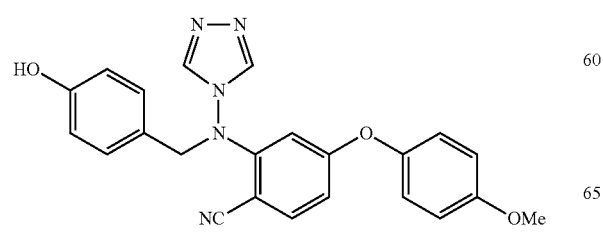
Compound 59
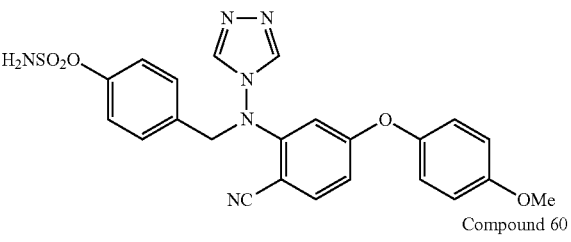
Compound 60
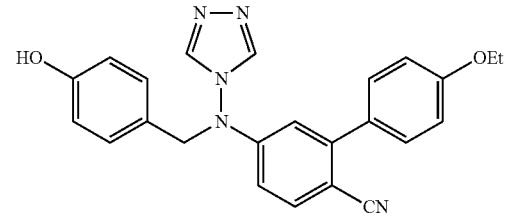
Compound 61
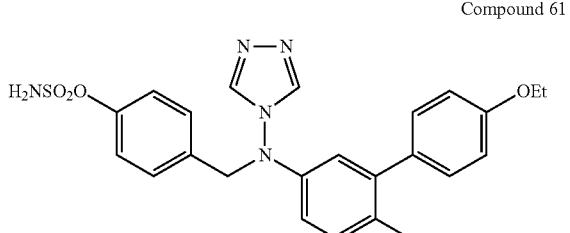
Compound 62
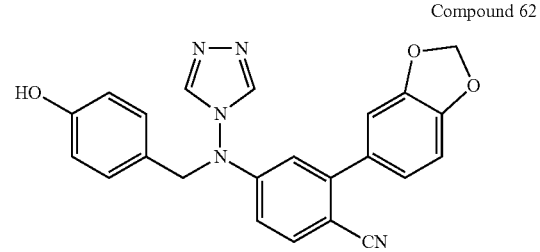
Compound 63
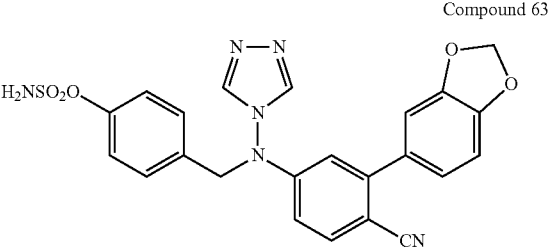
Compound 64
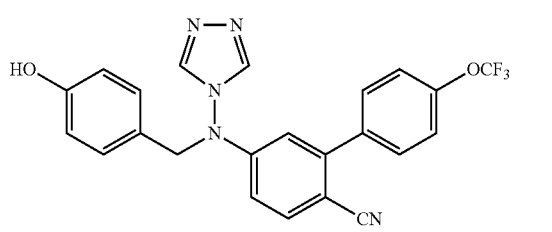

Compound 65

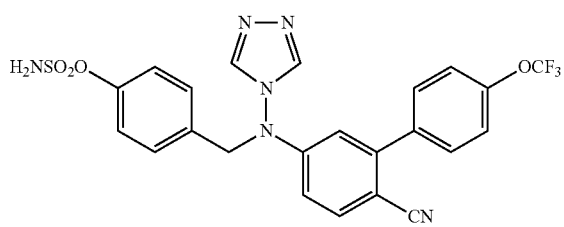

Biological Data

Aromatase inhibition was measured in accordance with Protocol 6.

Sterioid sulphatase inhibition was measured in accordance with Protocol 1

| Compound | JEG3 cells Aromatase $IC_{50}$ (nM) | JEG3 cells STS $IC_{50}$ (nM) |
|---|---|---|
| CAB06022 | 0.39 ± 0.09 | nd |
| CAB06021 | <0.1 | nd |
| CAB06025 | 0.14 ± 0.01 | 17 ± 2 |
| CAB06026 | 3.6 ± 0.4 | nd |
| CAB06043 | 1.6 ± 0.6 | nd |
| CAB06044 | 0.15 ± 0.03 | 2.3 ± 0.9 |
| CAB06045 | 0.018 ± 0.01 | 0.13 ± 0.01 |
| CAB06046 | 0.26 ± 0.12 | nd |
| CAB06049 | 0.015 ± 0.005 | 0.83 ± 0.15 |
| CAB06052 | 0.33 ± 0.01 | nd |
| CAB06054 | 0.1 ± 0.02 | 2900 ± 180 |
| CAB06059 | 0.05 ± 0.01 | 2900 ± 100 |
| CAB06077 | 0.015 ± 0.001 | 22 ± 6 |
| CAB06078 | 0.47 ± 0.18 | 55 ± 6 |
| CAB06088 | 0.75 ± 0.18 | 240 ± 60 |
| PMW04153 | <0.1 | 0.12 ± 0.02 |
| Compound 1 | <0.1 | nd |
| Compound 2 | 960 ± 53 | nd |
| Compound 3 | 0.25 ± 0.03 | 3 ± 0.5 |
| Compound 9 | 2.6 ± 0.2 | 3.9 ± 0.8 |
| Compound 11 | 850 ± 104 | 1300 ± 265 |
| Compound 12 | <0.1 | nd |
| Compound 13 | <0.1 | 41 ± 3 |
| Compound 15 | <0.1 | 60 ± 7 |
| Compound 17 | 3.4 ± 0.2 | 43 ± 6 |
| Compound 19 | 3.2 ± 0.1 | 181 ± 8 |
| Compound 21 | 44 ± 5 | nd |
| Compound 22 | 13.77 ± 4.51 | nd |
| Compound 23 | 89.0 ± 10.15 | 2800 ± 984.9 |
| Compound 24 | 0.14 ± 0.03 | Nd |
| Compound 25 | 3.97 ± 0.72 | 485 ± 50.7 |
| Compound 27 | 200 ± 5 | 5700 ±/− 1307 |
| Compound 29 | <0.1 | 1150 ± 50 |
| Compound 30 | 0.35 ± 0.06 | nd |
| Compound 31 | 1.43 ± 0.55 | 0.15 ± 0.03 |
| Compound 32 | <0.1 | 9.7 ± 4.2 |
| Compound 33 | 1.0 ± 0.3 | nd |
| Compound 34 | 0.8 ± 0.3 | 2.8 ± 0.9 |
| Compound 35 | <0.1 | nd |
| Compound 36 | <0.1 | 0.1 |
| Compound 37 | 0.23 ± 0.04 | nd |
| Compound 40 | 8 ± 1.7 | nd |
| Compound 41 | 97 ± 2.7 | 4363 ± 554 |
| Compound 44 | 3.1 ± 0.4 | nd |
| Compound 45 | 40.7 ± 4.5 | 292 ± 80 |
| Compound 46 | 4.1 ± 0.2 | nd |
| Compound 47 | 5.60 ± 0.10 | 14.0 ± 0.87 |
| Compound 50 | 4.03 ± 0.29 | nd |
| Compound 51 | 36 ± 1.7 | 198 ± 37 |
| Compound 56 | 1.82 ± 0.03 | nd |
| Compound 57 | 12.5 ± 2.3 | 62 ± 13 |
| Compound 66 | 0.77 ± 0.21 | 6350 ± 650 | n.d. = not determined

All publications and patents and patent applications mentioned in the above specification are herein incorporated by reference Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biology or related fields are intended to be within the scope of the following claims.

The invention claimed is:

1. A compound of formula V

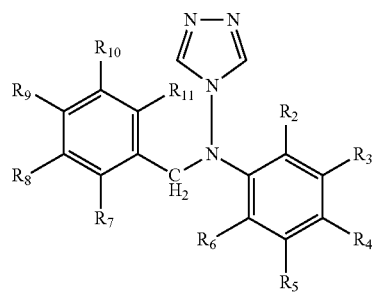

Formula V wherein each of $R_2$, $R_3$, $R_5$ and $R_6$ is independently selected from —H, $NO_2$, halo, —CN, —$NR_{12}R_{13}$, and —$(CH_2)_{0-1}R_{14}$;

wherein at least one of $R_2$, $R_3$, $R_5$ and $R_6$ is —$(CH_2)_{0-1}R_{14}$;

wherein $R_{12}$ and $R_{13}$ are independently selected from H, linear or branched hydrocarbon groups having a carbon chain of from 1 to 10 carbon atoms;

wherein $R_{14}$ is an unsubstituted or substituted phenyl group;

wherein $R_4$ is —CN;

wherein $R_9$ is —$OSO_2NR_{15}R_{16}$;

wherein each of $R_7$, $R_8$, $R_{10}$ and $R_{11}$ is independently selected from —H, $(C_1$-$C_6)$alkyl, —OH, —$OSO_2NR_{15}R_{16}$, and halo; and wherein $R_{15}$ and $R_{16}$ are independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups.

2. A compound according to claim 1 wherein each of $R_2$, $R_3$, $R_5$ and $R_6$ is independently selected from —H, —CN and —$(CH_2)_{0-1}R_{14}$.

3. A compound according to claim 1 wherein $R_2$ and $R_5$ are H.

4. A compound according to claim 1 wherein $R_2$, $R_5$, and $R_6$ are H.

5. A compound according to claim 1 wherein $R_3$ is —$(CH_2)_{0-1}R_{14}$.

6. A compound according to claim 1 wherein $R_{14}$ is

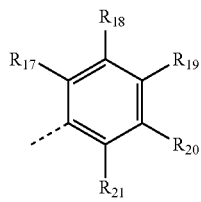

wherein each of $R_{17}$ to $R_{21}$ is independently selected from —H, $NO_2$, halo, —O—$(C_1-C_6)$haloalkyl, $(C_1-C_6)$haloalkyl, $(C_1-C_6)$alkyl, —CN, —OH, —OPh, —OBn, -Ph, —$OSO_2NR_{15}R_{16}$, —$SO_2R_{26}$, —$SO_2NR_{27}R_{28}$, —O—$(C_1-C_6)$alkyl, —$(C=O)_{0-1}NR_{29}R_{30}$ and —CO$(O)_{0-1}R_{31}$;

wherein $R_{15}$ and $R_{16}$ are independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups wherein each of $R_{26}$ to $R_{31}$ is independently selected from H, alkyl, cycloalkyl, alkenyl, acyl and aryl, or combinations thereof, or together represent alkylene, wherein the or each alkyl or cycloalkyl or alkenyl optionally contain one or more hetero atoms or groups.

7. A compound according to claim 1 wherein $R_3$ is

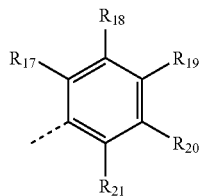

wherein each of $R_{17}$ to $R_{21}$ is independently selected from —H, $NO_2$, halo, $(C_1-C_6)$haloalkyl, $(C_1-C_6)$alkyl, CN, —OH, —$OSO_2NR_{15}R_{16}$, —$SO_2R_{26}$, —$SO_2NR_{27}R_{28}$, and —O—$(C_1-C_6)$alkyl;

wherein $R_{26}$, $R_{27}$ and $R_{28}$ are independently selected from H, alkyl, cycloalkyl, alkenyl, acyl and aryl.

8. A compound according to claim 1 wherein $R_3$ is

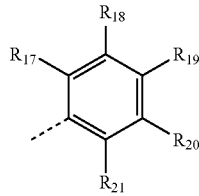

wherein each of $R_{17}$ to $R_{21}$ is independently selected from —H, halo, $(C_1-C_6)$haloalkyl, —$OSO_2NH_2$ and —O—$(C_1-C_6)$alkyl.

9. A compound according to claim 1 wherein $R_3$ is

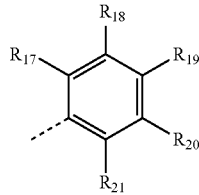

wherein each of $R_{17}$ to $R_{21}$ is —H.

10. A compound according to claim 1 wherein at least one of $R_7$, $R_8$, $R_{10}$ and $R_{11}$ is halo.

11. A compound according to claim 1 wherein at least one of $R_7$, $R_8$, $R_{10}$ and $R_{11}$ is —$OSO_2NR_{15}R_{16}$.

12. A compound according to claim 1 wherein at least one of $R_7$, $R_8$, $R_{10}$ and $R_{11}$ is halo and at least one of $R_7$, $R_8$, $R_{10}$ and $R_{11}$ is —$OSO_2NR_{15}R_{16}$.

13. A compound according to claim 1 wherein $R_8$ is halo.

14. A compound according to claim 1 wherein at least one of $R_{15}$ and $R_{16}$ is H.

15. A compound according to claim 1 wherein $R_{15}$ is H and $R_{16}$ is H.

16. A compound according to claim 1 wherein the group —$(CH_2)_{0-1}R_{14}$ is —$R_{14}$.

17. A pharmaceutical composition comprising the compound according to claim 1 optionally admixed with a pharmaceutically acceptable carrier, diluent, excipient or adjuvant.

18. A method for treating cancer comprising administering the compound of claim 1, wherein the cancer is selected from breast and ovarian cancer.

* * * * *